(12) United States Patent
Wilcox et al.

(10) Patent No.: US 12,007,397 B2
(45) Date of Patent: Jun. 11, 2024

(54) ENHANCED DETECTION AND QUANTITATION OF BIOMOLECULES

(71) Applicant: PrognomiQ, Inc., San Mateo, CA (US)

(72) Inventors: Bruce Wilcox, Keezletown, VA (US); Kavya Swaminathan, Mountain View, CA (US); Preston B. Williams, San Mateo, WA (US); Jared Deyarmin, San Bruno, MA (US); Mi Yang, Belmont, CA (US)

(73) Assignee: PrognomiQ, Inc., San Mateo, CA (US)

( * ) Notice: Subject to any disclaimer, the term of this patent is extended or adjusted under 35 U.S.C. 154(b) by 0 days.

(21) Appl. No.: 17/931,469

(22) Filed: Sep. 12, 2022

(65) Prior Publication Data
US 2023/0089033 A1 Mar. 23, 2023

Related U.S. Application Data

(60) Provisional application No. 63/243,645, filed on Sep. 13, 2021.

(51) Int. Cl.
*G01N 33/68* (2006.01)

(52) U.S. Cl.
CPC ..... *G01N 33/6848* (2013.01); *G01N 33/6896* (2013.01); *G01N 2458/15* (2013.01); *G01N 2570/00* (2013.01)

(58) Field of Classification Search
CPC ........... G01N 33/6848; G01N 2458/15; G01N 2570/00
See application file for complete search history.

(56) References Cited

U.S. PATENT DOCUMENTS

| | | |
|---|---|---|
| 7,632,686 B2 | 12/2009 | Anderson |
| 7,749,299 B2 | 7/2010 | Vanheusden et al. |
| 7,906,758 B2 | 3/2011 | Stults et al. |
| 9,002,652 B1 | 4/2015 | Hood et al. |
| 9,005,994 B2 | 4/2015 | Huo |
| 9,234,895 B2 | 1/2016 | Hood et al. |
| 9,394,332 B2 | 7/2016 | Markert-Hahn et al. |
| 9,445,994 B2 | 9/2016 | Irvine et al. |
| 9,549,901 B2 | 1/2017 | Shi et al. |

(Continued)

FOREIGN PATENT DOCUMENTS

| | | |
|---|---|---|
| CA | 2787201 A1 | 7/2011 |
| CN | 109470859 A | 3/2019 |

(Continued)

OTHER PUBLICATIONS

Acharjee et al. Integration of metabolomics, lipidomics and clinical data using a machine learning method. BMC Bioinformatics. 2016; 17(Suppl 15): 37-49.

(Continued)

*Primary Examiner* — Changhwa J Cheu
(74) *Attorney, Agent, or Firm* — Wilson Sonsini Goodrich & Rosati

(57) ABSTRACT

Described herein are methods for screening for a disease state. The method may include obtaining multiple data sets, and identifying the disease state based on a combination of the data sets. The data sets may include biomolecule measurements obtained by multiple methods, such as through the use of particles and reference biomolecules.

24 Claims, 16 Drawing Sheets

(56) References Cited

U.S. PATENT DOCUMENTS

| | | | |
|---|---|---|---|
| 9,589,374 | B1 | 3/2017 | Gao et al. |
| 9,868,756 | B2 | 1/2018 | Markert-Hahn et al. |
| 9,984,201 | B2 | 5/2018 | Zhang et al. |
| 10,466,230 | B2 | 11/2019 | Stults et al. |
| 10,829,816 | B2 | 11/2020 | Staker et al. |
| 10,866,242 | B2 | 12/2020 | Farokhzad et al. |
| 11,085,931 | B2 * | 8/2021 | Warthoe ............ G01N 33/54393 |
| 2004/0213446 | A1 | 10/2004 | Shams et al. |
| 2005/0048489 | A1 | 3/2005 | Thompson et al. |
| 2005/0221314 | A1 | 10/2005 | Berlin et al. |
| 2006/0008618 | A1 | 1/2006 | Wang et al. |
| 2007/0259363 | A1 | 11/2007 | Amri et al. |
| 2008/0187207 | A1 | 8/2008 | Bhanot et al. |
| 2008/0291122 | A1 | 11/2008 | Smith et al. |
| 2009/0090855 | A1 | 4/2009 | Kobold et al. |
| 2009/0176228 | A1 | 7/2009 | Birse et al. |
| 2010/0042329 | A1 | 2/2010 | Hood et al. |
| 2010/0188075 | A1 | 7/2010 | Litvinov et al. |
| 2011/0117582 | A1 | 5/2011 | Malima et al. |
| 2011/0171323 | A1 | 7/2011 | Weiss |
| 2011/0215237 | A1 | 9/2011 | Bateman |
| 2012/0046184 | A1 | 2/2012 | Dawson et al. |
| 2013/0080073 | A1 | 3/2013 | De Corral |
| 2013/0217057 | A1 | 8/2013 | Kearney et al. |
| 2014/0063009 | A1 | 3/2014 | Buehler et al. |
| 2014/0106976 | A1 | 4/2014 | Sachs et al. |
| 2015/0105276 | A1 | 4/2015 | Hofmann et al. |
| 2015/0253341 | A1 * | 9/2015 | McAvoy ............ G01N 33/6848 435/7.1 |
| 2016/0032395 | A1 | 2/2016 | Davicioni et al. |
| 2016/0047820 | A1 | 2/2016 | Kearney et al. |
| 2016/0054300 | A1 | 2/2016 | Winther et al. |
| 2016/0154006 | A1 | 6/2016 | Hermanson et al. |
| 2016/0260594 | A1 * | 9/2016 | Hendricks ............ H01J 49/24 |
| 2017/0024641 | A1 | 1/2017 | Wierzynski |
| 2017/0051073 | A1 | 2/2017 | Hynes et al. |
| 2017/0076195 | A1 | 3/2017 | Yang et al. |
| 2017/0220734 | A1 | 8/2017 | Colavin et al. |
| 2017/0277844 | A1 | 9/2017 | Apte et al. |
| 2018/0067119 | A1 | 3/2018 | Kearney et al. |
| 2018/0086713 | A1 * | 3/2018 | Elkon .................. C07D 403/12 |
| 2018/0172694 | A1 | 6/2018 | Farokhzad et al. |
| 2018/0274039 | A1 | 9/2018 | Zhang et al. |
| 2018/0275143 | A1 | 9/2018 | Wilcox et al. |
| 2019/0018019 | A1 | 1/2019 | Shan et al. |
| 2019/0147983 | A1 | 5/2019 | Shan et al. |
| 2019/0256924 | A1 | 8/2019 | Vogelstein et al. |
| 2019/0328837 | A1 | 10/2019 | Kim et al. |
| 2020/0002375 | A1 | 1/2020 | Chowdhury |
| 2020/0025765 | A1 | 1/2020 | Agorreta Arrazubi et al. |
| 2020/0025766 | A1 | 1/2020 | Hanash et al. |
| 2020/0381083 | A1 | 12/2020 | Chen |
| 2021/0000965 | A1 | 1/2021 | Wang et al. |
| 2021/0005327 | A1 | 1/2021 | Anwar et al. |
| 2021/0017598 | A1 | 1/2021 | Jain et al. |
| 2021/0031166 | A1 | 2/2021 | Porter et al. |
| 2021/0072255 | A1 | 3/2021 | Farokhzad et al. |
| 2021/0098083 | A1 | 4/2021 | Ma et al. |
| 2021/0104321 | A1 | 4/2021 | Lipsky et al. |
| 2021/0132071 | A1 | 5/2021 | Kostarelos et al. |
| 2021/0174958 | A1 | 6/2021 | Drake et al. |
| 2021/0302416 | A1 | 9/2021 | Soldo et al. |
| 2021/0375604 | A1 * | 12/2021 | Gajadhar ............ H01J 49/0036 |
| 2022/0148680 | A1 | 5/2022 | Blume et al. |
| 2022/0259202 | A1 * | 8/2022 | Meimetis ............ A61P 35/00 |
| 2022/0260559 | A1 | 8/2022 | Blume et al. |
| 2022/0299527 | A1 * | 9/2022 | Bateman ............ G01N 33/6896 |
| 2022/0317014 | A1 * | 10/2022 | Peterman ............ G01N 21/274 |
| 2022/0328129 | A1 | 10/2022 | Ma et al. |
| 2022/0328134 | A1 | 10/2022 | Ma et al. |
| 2022/0334118 | A1 | 10/2022 | Blume et al. |
| 2023/0266328 | A1 * | 8/2023 | Hadjidemetriou ............ G01N 33/6848 435/6.11 |

FOREIGN PATENT DOCUMENTS

| | | | | |
|---|---|---|---|---|
| EP | 1342794 | B1 | 12/2005 | |
| EP | 1394173 | B1 | 10/2007 | |
| EP | 2124051 | A1 * | 11/2009 | ......... G01N 33/6842 |
| EP | 2524219 | A2 | 11/2012 | |
| EP | 3510402 | A1 | 7/2019 | |
| EP | 3554681 | A1 | 10/2019 | |
| EP | 4096694 | A1 | 12/2022 | |
| GB | 2603051 | A | 7/2022 | |
| WO | WO-2005019477 | A2 | 3/2005 | |
| WO | WO-2008114917 | A1 | 9/2008 | |
| WO | WO-2010097785 | A1 | 9/2010 | |
| WO | WO-2013025759 | A1 | 2/2013 | |
| WO | WO-2013152989 | A2 | 10/2013 | |
| WO | WO-2014078855 | A1 | 5/2014 | |
| WO | WO-2015116837 | A1 | 8/2015 | |
| WO | WO-2015159293 | A2 | 10/2015 | |
| WO | WO-2016008451 | A1 | 1/2016 | |
| WO | WO-2016207391 | A1 | 12/2016 | |
| WO | WO-2017106481 | A1 | 6/2017 | |
| WO | WO-2017192965 | A2 | 11/2017 | |
| WO | WO-2017212428 | A1 | 12/2017 | |
| WO | WO-2018046542 | A1 | 3/2018 | |
| WO | WO-2018112460 | A1 | 6/2018 | |
| WO | WO-2018119216 | A1 | 6/2018 | |
| WO | WO-2018161031 | A1 | 9/2018 | |
| WO | WO-2018170518 | A1 | 9/2018 | |
| WO | WO-2019050966 | A2 | 3/2019 | |
| WO | WO-2019067092 | A1 | 4/2019 | |
| WO | WO-2019182885 | A1 | 9/2019 | |
| WO | WO-2019200410 | A1 | 10/2019 | |
| WO | WO-2019209888 | A1 | 10/2019 | |
| WO | WO-2020096631 | A2 | 5/2020 | |
| WO | WO-2020198209 | A1 | 10/2020 | |
| WO | WO-2021026172 | A1 | 2/2021 | |
| WO | WO-2021087407 | A1 | 5/2021 | |
| WO | WO-2021154893 | A1 * | 8/2021 | .............. A61P 35/00 |
| WO | WO-2022020272 | A1 | 1/2022 | |
| WO | WO-2022072471 | A1 | 4/2022 | |
| WO | WO-2022182989 | A1 | 9/2022 | |
| WO | WO-2022212583 | A1 | 10/2022 | |
| WO | WO-2023039479 | | 3/2023 | |
| WO | WO-2023039579 | | 3/2023 | |
| WO | WO-2023164697 | | 8/2023 | |
| WO | WO-2023240046 | A2 | 12/2023 | |

OTHER PUBLICATIONS

"Adalsteinsson, V.A., Ha, G., Freeman, S.S. et al. Scalable whole-exome sequencing of cell-free DNA reveals high concordance with metastatic tumors. Nat Commun 8, 1324 (2017). https://doi.org/10.1038/s41467-017-00965-y".

Albers, et al., Dating genomic variants and shared ancestry in population-scale sequencing data. PLOS Biology, Jan. 2020, 18(1): 19 Pages. https://doi.org/10.1371/journal.pbio.3000586.

Alcalá et al. The Anthrax Toxin receptor 1 (ANTXR1) Is enriched in pancreatic cancer stem cells derived from primary tumor cultures. Stem Cells International, 2019, Article ID:1378639, 1-13 pages.

Altobelli et al. HtrA1: Its future potential as a novel biomarker for cancer. Oncology Reports, 2015, 34:555-566.

Andreeva, A.V., and Kutuzov, M.A. Cadherin 13 in cancer. Genes Chromosomes Cancer, 2010, 49(9):775-90.

Armagan, et al., Generalized Beta Mixtures of Gaussians. Advances in neutral information processing systems. Mar. 13, 2012; 1-9 Pages.

Arroyo et al. Expression-based, consistent biomarkers for prognosis and diagnosis in lung cancerClin Transl Oncol, 2020; 22(10):1867-1874.

Bakry et al. Protein profiling for cancer biomarker discovery using matrix-assisted laser desorption/ionization time-of-flight mass spectrometry and infrared imaging: A review. Analytica Chimica Acta 2011, vol. 690, pp. 26-34 (Year: 2011).

Bell et al. A HUPO test sample study reveals common problems in mass spectrometry-based proteomics. Nat Methods. Jun. 2009; 6(6): 423-430.

(56) References Cited

OTHER PUBLICATIONS

Benjamini e al. Controlling the false discovery rate: a practical and powerful approach to multiple testing. Journal of the Royal Statistical Society. Series B (Methodological). pp. 289-300 (1995).
Bludau, I., Aebersold, R. Proteomic and interactomic insights into the molecular basis of cell functional diversity. Nat Rev Mol Cell Biol 2020;21: 327-340. https://doi.org/10.1038/s41580-020-0231-2.
Blume, et al., Rapid, deep and precise profiling of the plasma proteome with multi-nanoparticle protein corona. Nature Communications, 2020; 11(3662): 1-14.
Bresnick et al. S100 proteins in cancer. Nature Reviews Cancer, 2015, 15:96-109.
Bronsema, K. J. et al; "Internal standards in the quantitative determination of protein biopharmaceuticals using liquidchromatography coupled to mass spectrometry", Journal of Chromatography B, vols. 893-894, 2012, pp. 1-14. (Year: 2012).
"Butler et al., Lipids and Cancer: Emerging roles in pathogenesis, diagnosis and therapeutic intervention. Advanced Drug Delivery Review. 2020; 159:245-293".
Capriotti et al.: Analytical methods for characterizing the nanoparticle-protein corona. Chromatographia 77(11-12):755-769 DOI:10.1007/s10337-014-2677-x (2014).
Caracciolo, et al., Disease-specific protein corona sensor arrays may have disease detection capacity, 2019, Nanoscale Horiz., 4, p. 1063-1076. (Year:2019).
Carbone et al. Angiopoietin-Like proteins in Angiogenesis, Inflammation and cancer. Int J Mol Sci. Feb. 2018; 19(2): 431 (1-22).
"Chantada-Vazquez, et al., Identification of a Profile of Neutrophil-Derived Granule Proteins in the Surface of Gold Nanoparticles after Their Interaction with Human Breast Cancer Sera. Nanomaterials (Basel, Switzerland), 2020; 10(1223): 1-18. https://doi.org/10.3390/nano10061223".
Chantada-Vazquez, et al., Proteomic analysis of the bio-corona formed on the surface of (Au, Ag, Pt)-nanoparticles in human serum. Colloids Surf B Biointerfaces. May 1, 2019;177:141-148. doi: 10.1016/j.colsurfb.2019.01.056. Epub Jan. 29, 2019. PMID: 30721790.
Chantada-Vazquez et al., Proteomic investigation on bio-corona of Au, Ag and Fe nanoparticles for the discovery of triple negative breast cancer serum protein biomarkers. J Proteomics. Feb. 10, 2020;212:103581; 1-19 Pages. doi: 10.1016/j.jprot.2019.103581. Epub Nov. 12, 2019. PMID: 31731051.
Chen, et al., Glycoproteomics analysis of human liver tissue by combination of multiple enzyme digestion and hydrazide chemistry. J Proteome Res. Feb. 2009;8(2):651-61. doi: 10.1021/pr8008012.
Chen et al. Network analysis of differentially expressed smoking-associated mRNAs, lncRNAs and miRNAs reveals key regulators in smoking-associated lung cancer. Exp. Ther. Med., 2018;16: 4991-5002.
Chen, T., Kornblith, S., Norouzi, M et al. A Simple Framework for Contrastive Learning of Visual Representations. Proceedings of the 37 th International Conference on Machine Learning, Vienna, Austria, PMLR 119, 2020; 11 Pages.
Cho et al. Serum amyloid A is elevated in the serum of lung cancer patients with poor prognosis. Br J Cancer. 2010, 102(12): 1731-1735.
"Choi, et al., DUX4 recruits p300/CBP through its C-terminus and induces global H3K27 acetylation changes. Nucleic Acids Research, 2016. vol. 44m No. 11, 5161-5173."
"Schwenk, et al., The Human plasma proteome draft of 2017: Building on the human plasma peptideatlas from mass spectrometry and complementary assays. Journal Proteome Research, Dec. 2017; 16(12): 4299-4310."
Cohen, et al., Combined circulating tumor DNA and protein biomarker-based liquid biopsy for the earlier detection of pancreatic cancers. PNAS, Sep. 5, 2017; 114 (38) 10202-10207, https://doi.org/10.1073/pnas.1704961114.
Cohen, et al., Detection and localization of surgically resectable cancers with a multi-analyte blood test. Science Feb. 23, 2018: vol. 359, Issue 6378, pp. 926-930. DOI: 10.1126/science.aar3247.
Co-pending U.S. Appl. No. 17/930,663, inventors Liu; Manway et al., filed Sep. 8, 2022.
Co-pending U.S. Appl. No. 18/150,390, inventors Ma; Philip et al., filed Jan. 5, 2023.
Corbo, et al., Analysis of the Human Plasma Proteome Using Multi-Nanoparticle Protein Corona for Detection of Alzheimer's Disease. Adv. Healthcare Mater. 2021, 10, 2000948; 1-10 Pages. https://doi.org/10.1002/adhm.202000948.
"Corley, et al., Adenoma Detection Rate and Risk of Colorectal Cancer and Death. New Engl J Med Apr. 2014; 370:1298-1306."
Cox et al. MaxQuant enables high peptide identification rates, individualized p.p.b.-range mass accuracies and proteome-wide protein quantification. Nat Biotechnol 26:1367-1372 (2008).
Datta, S. et al., Statistical Analysis of Proteomics, Metabolomics, and Lipidomics Data Using Mass Spectrometry. Springer Cham, 2017; 295 Pages.
Demichev et al.: DIA-NN: neural networks and interference correction enable deep proteome coverage in high throughput. Nature Methods 17(1):41-44 DOI:10.1038/s41592-019-0638 (2020).
Domenico, et al., Nanoparticle-biomolecular corona: A new approach for the early detection of non-small-cell lung cancer, 2019, J Cell Physiol., 234, p. 9378-9386. (Year:2019).
Dougan et al. Proteomics-Metabolomics Combined Approach Identifies Peroxidasin as a Protector against Metabolic and Oxidative Stress in Prostate Cancer. Int. J. Mol. Sci., 2019, 20(12):3046.
Epelbaum et al. Haptoglobin-related protein as a Serum marker in Malignant Lymphoma. Pathology Oncology Research, 1998, 4(4):271-276.
Falahati et al., A health concern regarding the protein corona, aggregation and disaggregation, 2019, BBA—General Subjects, 1863, p. 971-991 (Year:2019).
Fan et al. Intelligence Algorithms for Protein Classification by Mass Spectrometry. BioMed Research International, vol. 2018, Article ID 2862458, 11 pages, 2018.
"Fredolini, et al., Shotgun proteomics coupled tonanoparticle-based biomarker enrichment reveals a novel panel of extracellular matrix proteins as candidate serum protein biomarkers for early-stage breast cancer detection. Breast Cancer Research (2020) 22:135https://doi.org/10.1186/s13058-020-01373-9".
Gao, et al., "A latent factor model with a mixture of sparse and dense factors to model gene expression data with confounding effects." arXiv preprint arXiv:1310.4792 (Oct. 17, 2013) 1-28 Pages.
"Gao, et al., Evaluation of Serum Cea, CA19-9, CA72-4, CA125 and Ferritin as Diagnostic markers and factors of clinical parameters for colorectal cancer. Science Reports, 2018; 8:2732."
GB2205544.6 Examination Report dated Jun. 14, 2022.
Geary et al. Identification of a Biomarker Panel for Early Detection of Lung Cancer patients. J. Proteome Res. 2019, 18, 9, 3369-3382.
Gould et al. Recent trends in the identification of incidental pulmonary nodules. Am J Respir Crit Care Med. Nov. 15, 2015;192(10):1208-14.
Graham et al. ST6GAL1: A key player in Cancer (Review). Oncol Lett. Aug. 2019; 18(2): 983-989.
Grossi et al. Prognostic role of the VeriStrate test in first line patients with non-small cell lung cancer treated with platinum-based chemotherapy. Lung Cancer 2018, vol. 117, pp. 64-69 (Year: 2018).
"Guinney, et al., The Consensus Molecular subtypes of colorectal cancer. Nat. Med. Nov. 2015; 21(11): 1350-1356."
Guler et al. Detection of Early Stage Pancreatic Cancer Using 5-Hydroxymethylcytosine Signatures in Circulating Cell Free DNA. Nature Communications 11(1):5270 (Dec. 2020).
Gunther, O.P. et al. A computational pipeline for the development of multi-marker bio-signature panels and ensemble classifiers. BMC Bioinformatics 13,326 (2012), p. 1-17. (Year: 2012).
Guo et al. Deep multiple instance learning classifies subtissue locations in mass spectrometry images from tissue-level annotations. Bioinformatics, vol. 36, Issue Supplement_1, Jul. 2020, pp. i300-i308.

(56) References Cited

OTHER PUBLICATIONS

"Gupta, et al., Recommendations for follow-up after colonoscopy and polypectomy: a consensus update by the US multi-society task force on colorectal cancer. Gastrointest Endosc. Mar. 2020; 91(3): 463-485."

Hadjidemetriou, et al., A novel scavenging tool for cancer biomarker discovery based on the blood-circulating nanoparticle protein corona. Biomaterials. Jan. 2019; vol. 188: pp. 118-129.

Hadjidemetriou, Liposome protein corona in vivo: from fundamental principles to a tool for cancer biomarker discovery, 2017,University of Manchester, p. 1-233 (Year: 2017).

Hamm et al. Frequent expression loss of Inter-alpha-trypsin inhibitor heavy chain (ITIH) genes in multiple human solid tumors: A systematic expression analysis. BMC Cancer, Jan. 28, 2008, 8:25; 1-15 Pages.

Hammerschmidt et al., Lung Cancer: Current Diagnosis and Treatment, 2009, Dtsch Arztebl, 106(49), p. 809-820 (Year: 2009).

Hanahan et al. Hallmarks of cancer: the next generation. Cell 144:646-674 (2011).

Haque, IS et al., Challenges in using ctDNA to achieve early detection of cancer. bioRxiv; Dec. 2017. 20 Pages; DOI: 10.1101/237578.

"Hasan, et al., Advances in pancreatic cancer biomarkers. Oncol Rev. Jan. 2019; 13(410): 69-76."

Hasin, Yehudit, Marcus Seldin, and Aldons Lusis. "Multi-omics approaches to disease." Genome biology 18.1 (2017): 1-15. (Year:2017).

Haug U, Knudsen AB, Lansdorp-Vogelaar I, Kuntz KM. Development of new non-invasive tests for colorectal cancer screening: the relevance of information on adenoma detection. Int J Cancer. Jun. 15, 2015;136(12):2864-74. doi: 10.1002/ijc.29343. Epub Dec. 3, 2014. PMID: 25403937; PMCID: PMC4397119.

Havel et al. The evolving landscape of biomarkers for checkpoint inhibitor immunotherapy. Nat Rev Cancer 19(3):133-150 (2019).

Havlis, Jan, and Andrej Shevchenko. "Absolute quantification of proteins in solutions and in polyacrylamide gels by massspectrometry." Analytical chemistry 76.11 (2004): 3029-3036. (Year: 2004).

"Haynes, et al., Empowering multi-cohort gene expression analysis to increase reproducibility. Pac Symp Biocomput. 2016; 22: 144-153."

Heitzer, E. et al., Current and future perspectives of liquid biopsies in genomics-driven oncology. Nat Rev Genet 20, 71-88 (2019). https://doi.org/10.1038/s41576-018-0071-5.

"Huang, et al., Emerging trends and research foci in gastrointestinal microbiome. J Transl. Med. 2019; 17(67): 1-11."

"Siegel, et al., Cancer Statistics, 2021. CA: A Cancer Journal for Clinicians. Jan. 2021; vol. 71 Issue 1: 7-33."

"Silvestri GA, Tanner NT, Kearney P, Vachani A, Massion PP, Porter A, Springmeyer SC, Fang KC, Midthun D, Mazzone PJ; PANOPTIC Trial Team. Assessment of Plasma Proteomics Biomarker's Ability to Distinguish Benign From Malignant Lung Nodules: Results of the PANOPTIC (Pulmonary Nodule Plasma Proteomic Classifier) Trial. Chest. Sep. 2018;154(3):491-500. doi: 10.1016/j.chest.2018.02.012. Epub Mar. 1, 2018. PMID: 29496499; PMCID: PMC6689113."

"Imperiale, et al., Multitarget stool DNA testing for colorectal-cancer screening. N Engl J Med. Apr. 2014; 370:1287-1297."

Jensen, M., and Berthold, F. Targeting the neural cell adhesion molecule in cancer. Cancer Lett., Dec. 2007., 258(1):9-21.

Jiang et al. "Surface-Enhanced Raman Nanoprobes with Embedded Standards for Quantitative Cholesterol Detection" small methods, vol. 2 Issue 11 (Nov. 13, 2018): pp. 1-14; entire document.

John, et al., "Predicting gene expression from plasma cell-free DNA using both the fragment length and fragment position." AACR Annual Meeting; Mar. 29-Apr. 3, 2019; 1 Page.

Jong et al. Selecting a classification function for class prediction with gene expression data. Bioinformatics, vol. 32, Issue 12, Jun. 15, 2016, pp. 1814-1822.

"Kampf C et al., The human liver-specific proteome defined by transcriptomics and antibody-based profiling. FASEB J. (2014) PubMed: 24648543 DOI: 10.1096/fj.14-250555".

Keshishian, et al., Multiplexed, Quantitative Workflow for Sensitive Biomarker Discovery in Plasma Yields Novel Candidates for Early Myocardial Injury. Mol Cell Proteomics. Sep. 2015;14(9):2375-93. doi: 10.1074/mcp.M114.046813. Epub Feb. 27, 2015.

Keshishian, et al., Quantitative, multiplexed workflow for deep analysis of human blood plasma and biomarker discovery by mass spectrometry. Nat Protoc. Aug. 2017;12(8):1683-1701. doi:10.1038/nprot.2017.054. Epub Jul. 27, 2017.

Khlebtsov et al. "Gap-enhanced Raman tags: fabrication, optical properties, and theranostic applications" Theranostics, vol. 10 Issue 5 (2020): pp. 2067-2094; entire document.

Kim, et al., A chemical with proven clinical safety rescues down-syndrome-related phenotypes in through DYRK1A inhibition. Disease Models & Mechanisms (2016) 9, 839-848.

"Klein, et al., Clinical validation of a targeted methylation-based multi-cancer early detection test using an independent validation set. Annals of Oncology, 2021; vol. 32 Issue 9: 1167-1177."

Koh, H.M., et al., Prognostic Role of S100A8 and S100A9 Protein expressions in non-small cell carcinoma of the lung. Journal of pathology and translational medicine, 2019; 53:13-22.

"Koizumi, et al., Salivary cytokine panel indicative of non-small cell lung cancer. J Int Med Res. 2018; vol. 46(9): 3570-3582."

Lamjabbar-Alaoui et al. Lung Cancer: Biology and Treatment options. Biochimica et Biophysica Acta 2015, 1856, pp. 189-210 (Year: 2015).

Leal et al. Prognostic performance of proteomic testing in advanced non-small cell lung cancer: a systematic literature review and meta-analysis. Current Medical Research and Opinion 2020, vol. 36, No. 9, pp. 1497-1505 (Year: 2020).

Lee et al. The clinical role of VeriStrat testing in patients with advanced non-small cell lung cancer considered unfit for first-line platinum-based chemotherapy. European Journal of Cancer 2019, vol. 120, pp. 86-96 (Year: 2019).

"Li et al., PGAM1, regulated by miR-3614-5p, functions as an oncogene by activating transforming growth factor-B (TGF-B) signaling in the progression of non-small cell lung carcinoma. Cell death and Disease, 2011; 11(710): 1-16."

Li, L. et al; "Data mining techniques for cancer detection using serum proteomic profiling", Artificial Intelligence in Medicine, vol. 32, Issue 2, 2004, pp. 71-83 (Year: 2004).

Lin, E., Lane, HY. "Machine learning and systems genomics approaches for multi-omics data." Biomark Res 5, 2 (2017), p. 1-6 (Year: 2017).

Liu et al. High expression of NFAT2 contributes to carboplatin resistance in lung cancer. Experimental and Molecular Pathology, 2019; 110:104290.

Liu, et al., Human plasma N-glycoproteome analysis by immunoaffinity subtraction, hydrazide chemistry, and mass spectrometry. J Proteome Res. Nov.-Dec. 2005;4(6):2070-80. doi: 10.1021/pr0502065.

"Liu, et al., Sensitive and specific multi-cancer detection and localization using methylation signatures in cell-free DNA. Ann Oncol. Jun. 2020; 31(6): 745-759."

Liu et al., Spatial co-fragmentation pattern of cell-free DNA recapitulates in vivo chromatin organization and identifies tissues-of-origin. AACR. 2019; 1 Page.

"Lock, et al., Joint and individual variation explained (JIVE) for integrated analysis of multiple data types. Ann Appl Stat. Mar. 1, 2013;7(1):523-542. doi: 10.1214/12-AOAS597."

Lu, et al., The crucial role of multiomic approach in cancer research and clinically relevant outcomes. EPMA Journal (2018) 9; 77-102: https://doi.org/10.1007/s13167-018-0128-8.

Lu, J., and Gu, J. Significance of β-Galactoside α2,6 Sialyltranferase 1 in Cancers. Molecules, 2015, 20, 7509-7527.

Ludwig C, Gillet L, Rosenberger G, Amon S, Collins BC, Aebersold R. Data-independent acquisition-based SWATH-MS for quantitative proteomics: a tutorial. Mol Syst Biol. Aug. 13, 2018;14(8):e8126; 1-23 Pages. doi: 10.15252/msb.20178126. PMID: 30104418; PMCID: PMC6088389.

"Luz-Crawford et al., Mesenchymal Stem Cell-Derived Interleukin 1 Receptor Antagonist Promotes Macrophage Polarization and Inhibits B Cell Differentiation. Stem Cells. Feb. 2016;34(2):483-92. doi: 10.1002/stem.2254. Epub Dec. 31, 2015. PMID: 26661518."

(56) References Cited

OTHER PUBLICATIONS

Maples, et al., A highly accurate noninvasive multi-omics diagnostic test for nash. DiscernDx, Inc. Nash-Tag conference Abstract Book, Mar. 2021, p. 14.
"Massion P.P. and Walker R.C. Indeterminate pulmonary nodules: Risk for having or for developing lung cancer. Cancer Prev. Res. 2014; 7(12): 1173-1178."
"Mathios, D., Johansen, J.S., Cristiano, S. et al. Detection and characterization of lung cancer using cell-free DNA fragmentomes. Nat Commun 12, 5060 (2021). https://doi.org/10.1038/s41467-021-24994-w".
Mazzaschi G, Facchinetti F, Missale G, Canetti D, Madeddu D, Zecca A, Veneziani M, Gelsomino F, Goldoni M, Buti S, Bordi P, Aversa F, Ardizzoni A, Quaini F, Tiseo M. The circulating pool of functionally competent NK and CD8+ cells predicts the outcome of anti-PD1 treatment in advanced NSCLC. Lung Cancer. Jan. 2019;127:153-163. doi: 10.1016/j.lungcan.2018.11.038. Epub Nov. 29, 2018. PMID: 30642544.
McDonald et al. Suspected cancer symptoms and blood test results in primary care before a diagnosis of lung cancer: a case-control study. Future Oncol. (2019) 15(33), 3755-3762.
"McGuigan A, Kelly P, Turkington RC, Jones C, Coleman HG, McCain RS. Pancreatic cancer: A review of clinical diagnosis, epidemiology, treatment and outcomes. World J Gastroenterol. Nov. 21, 2018;24(43):4846-4861. doi: 10.3748/wjg.v24.i43.4846. PMID: 30487695; PMCID: PMC6250924."
"Meester RG, Doubeni CA, Lansdorp-Vogelaar I, Goede SL, Levin TR, Quinn VP, Ballegooijen Mv, Corley DA, Zauber AG. Colorectal cancer deaths attributable to nonuse of screening in the United States. Ann Epidemiol. Mar. 2015;25(3):208-213.e1. doi: 10.1016/j.annepidem.2014.11.011. Epub Dec. 5, 2014. PMID: 25721748; PMCID: PMC4554530."
Muller et al. Community-integrated omics links dominance of a microbial generalist to fine-tuned resource usage. Nature Communications vol. 5, Article No. 5603 (2014); 1-10 Pages.
"Murakami M, Naraba H, Tanioka T, Semmyo N, Nakatani Y, Kojima F, Ikeda T, Fueki M, Ueno A, Oh S, Kudo I. Regulation of prostaglandin E2 biosynthesis by inducible membrane-associated prostaglandin E2 synthase that acts in concert with cyclooxygenase-2. J Biol Chem. Oct. 20, 2000;275(42):32783-92. doi: 10.1074/jbc. M003505200. PMID: 10869354."
"Nakao, et al., Oncological problems in pancreatic cancer surgery. World J Gastroenterol 2006; 12(28): 4466-4472 [PMID: 16874856 DOI: 10.3748/wjg.v12.i28.4466]".
Ocana, A., Pandiella, A. "Personalized therapies in the cancer omics era", Mol Cancer 9, 202 (2010), p. 1-12. (Year: 2010).
"Song, et al., Diagnostic and prognostic significance of serum apolipoprotein C—I in triple-negative breast cancer based on mass spectrometry. Cancer Biology & Therapy, 2016; 17(6): 635-647."
Parimon et al. Syndecan-1 Controls Lung Tumorigenesis by Regulating miRNAs Packaged in Exosomes. Am J Pathol. 2018; 188(4): 1094-1103.
PCT/US2021/015339 International Search Report and Written Opinion dated Apr. 13, 2021.
PCT/US2022/022654 International Search Report and Written Opinion dated Aug. 15, 2022.
PCT/US2022/076297 International Search Report and Written Opinion dated Nov. 30, 2022.
"Pereira, S. P., Oldfield, L., Ney, A., Hart, P. A., Keane, M. G., Pandol, S. J., Li, D., Greenhalf, W., Jeon, C. Y., Koay, E. J., Almario, C. V., Halloran, C., Lennon, A. M., & Costello, E. (2020). Early detection of pancreatic cancer. The lancet. Gastroenterology & hepatology, 5(7), 698-710. https://doi.org/10.1016/S2468-1253(19)30416-9".
Pirinen et al. Versican in nonsmall cell lung cancer: Relation to hyaluronan, clinicopathologic factors, and prognosis. Human Pathlogy, 2004; 36(1):44-50.
Polasky, et al., Fast and comprehensive N- and O-glycoproteomics analysis with MSFragger-Glyco. Nat Methods. Nov. 2020;17(11):1125-1132. doi: 10.1038/s41592-020-0967-9. Epub Oct. 5, 2020.
Ponzi, et al., Integrative, multi-omics, analysis of blood samples improves model predictions: applications to cance. BMC Bioinformatics, 2021; 22:395; 1-17 Pages. https://doi.org/10.1186/s12859-021-04296-0.
Putcha, et al., Blood-based detection of early-stage colorectal cancer using multiomics and machine learning. Journal of clinical oncology, 2020; 38(4): 66, 3 Pages.
Qian et al. Screening for early stage lung cancer and its correlation with lung nodule detection. J Thorac Dis 2018, 1 0(Suppl 7): S846-859 (Year: 2018).
"Qu WQ, Liu L, Yu Z. Clinical value of microRNA-23a upregulation in non-small cell lung cancer. Int J Clin Exp Med. Aug. 15, 2015;8(8):13598-603. PMID: 26550300; PMCID: PMC4612985."
Ramos-Esquivel et al., Anti-PD-1/anti-PD-L1 immunotherapy versus docetaxel for previously treated advanced non-small cell lung cancer: a systematic review and meta-analysis of randomised clinical trials. ESMO Open 2017;2:e000236; 1-11 Pages. doi:10.1136/esmoopen-2017-000236.
Reel PS, Reel S, Pearson E, Trucco E, Jefferson E. Using machine learning approaches for multi-omics data analysis: A review. Biotechnol Adv. Jul.-Aug. 2021;49:107739; 24 Pages. doi: 10.1016/j.biotechadv. 2021.107739. Epub Mar. 29, 2021. PMID: 33794304.
"Robinson, et al., A Systematic Investigation of the Malignant Functions and Diagnostic Potential of the Cancer Secretome. Cell Rep. Mar. 5, 2019; 26(10):2622-2635.e5. doi: 10.1016/j.celrep.2019. 02.025."
Roushan, et al., Peak Filtering, Peak Annotation, and Wildcard Search for Glycoproteomics. Mol Cell Proteomics. 2021;20:100011. doi: 10.1074/mcp.RA120.002260. Epub Dec. 8, 2020.
Roy et al. Multiomics data collection visualization and utilization for guiding metabolic engineering. Frontiers in bioengineering and biotechnology, 2021, 9, Article 612983; 1-13 Pages.
"Ruan H., Hu S., Zhang H., Du G., Li X., Li X., Li X. Upregulated SOX9 expression indicates worse prognosis in solid tumors: a systematic review and meta-analysis. Oncotarget. 2017; 8: 113163-113173. Retrieved from https://www.oncotarget.com/article/22635/text/".
Rubio, et al., Multi-omic analysis unveils biological pathways in peripheral immune system associated to minimal hepatic encephalopathy appearance in cirrhotic patients. Scientific Reports, 2021; 11:1907; 14 Pages. https://doi.org/10.1038/s41598-020-80941-7.
Skyarysz, A., Alkhalifah, Y., Darnley, K., Eddleston, M., McLaren, D., Nailon, W. H., Salman, D., Sykora, M., Thomas, P., & Soltoggio, A., Convolutional neural networks for automated targeted analysis of raw gas chromatography-mass spectrometry data. In Proceedings of the International Joint Conference on Neural Networks (IJCNN 2018) At: Rio de Janeiro, Brazil; 2018: 9 Pages. https://doi.org/10. 1109/IJCNN.2018.8489539.
Song, M. et al; "A Review of Integrative Imputation for Multi-Omics Datasets" Front. Genet. vol. 11, article 570255, Oct. 15, 2020, p. 1-15 (Year: 2020).
St. John et al., Predicting gene expression from plasma cell-free DNA using both the fragment length and fragment position. AACR. 2019; 1 Page.
Stelzer, et al., The GeneCards Suite: From Gene Data Mining to Disease Genome Sequence Analyses. Curr Protoc Bioinformatics. Jun. 20, 2016;54:1.30.1-1.30.33. doi: 10.1002/cpbi.5.
Telenti, A. et al. Deep sequencing of 10,000 human genomes. Proc. Natl. Acad. Sci. USA 113(42):11901-11906 (Oct. 18, 2016).
Tenzer, S., et al. Nanoparticle size is a critical physicochemical determinant of the human blood plasma corona: a comprehensive quantitative proteomic analysis. ACS Nano 5, 7155-7167 (2011).
"The 1000 Genomes Project Consortium. A global reference for human genetic variation. Nature 526, 68-74 (2015). https://doi.org/10.1038/nature15393".
"Uhlen, M. et al., A Pathology atlas of the human cancer transcriptome. Science. 2017. PubMed: 28818916 DOI: 10.1126/science. aan2507".
Ulz, et al., Inference of transcription factor binding from cellfree DNA enables tumor subtype prediction and early detection. Nature Communications, (2019) 10:4666;1-11 Pages. https://doi.org/10. 1038/s41467-019-12714-4, https://doi.org/10.1038/s41467-019-12714-4.

(56) References Cited

OTHER PUBLICATIONS

Unger, Klaus K., et al. "Liquid chromatography-its development and key role in life science applications." Angewandte ChemieInternational Edition 49.13 (2010): 2300-2312 (Year: 2010).
U.S. Appl. No. 17/585,303 Office Action dated Apr. 25, 2022.
U.S. Appl. No. 17/585,303 Office Action dated Jul. 18, 2022.
U.S. Appl. No. 17/709,185 Office Action dated Dec. 7, 2022.
U.S. Appl. No. 17/709,185 Office Action dated Sep. 15, 2022.
U.S. Appl. No. 17/709,202 Office Action dated Nov. 23, 2022.
U.S. Appl. No. 17/720,197 Office Action dated Jan. 5, 2023.
U.S. Appl. No. 17/720,197 Office Action dated Oct. 14, 2022.
"Voronov, Elena et al. "Unique Versus Redundant Functions of IL-1α and IL-1β in the Tumor Microenvironment." Frontiers in immunology vol. 4 177. Jul. 8, 2013, doi:10.3389/fimmu.2013.00177".
Wainberg, et al., Multiomic blood correlates of genetic risk identify presymptomatic disease alterations. PNAS, Sep. 2020; vol. 117, No. 35: 21813-21820.
Wan, et al., Machine learning enables detection of early-stage colorectal cancer by whole-genome sequencing of plasma cell-free DNA. BMC Cancer (2019) 19:832; 1-10 Pages. https://doi.org/10.1186/s12885-019-6003-8.
Wang et al. MOGONET integrates multi-omics data using graph convolutional networks allowing patient classification and biomarker identification. Nature Communications, 2021; 12:3445.
Weinstein, et al. The cancer genome atlas pan-cancer analysis project. Nature genetics 45.10 (2013): 1113-1120.
"White A, Thompson TD, White MC, et al. Cancer Screening Test Use—United States, 2015. MMWR Morb Mortal Wkly Rep Mar. 2017;66(8):201-206. DOI: http://dx.doi.org/10.15585/mmwr.mm6608a1".
Xu et al. Calpain-2 Enhances non-small cell lung cancer progresion and Chemoresistance to paclitaxel via EGFR-pAKT pathway. Int J Biol Sci. 2019; 15(1): 127-137.
"Yigit M, Değirmencioğlu S, Ugurlu E, Yaren A. Effect of serum interleukin-1 receptor antagonist level on survival of patients with non-small cell lung cancer. Mol Clin Oncol. May 2017;6(5):708-712. doi: 10.3892/mco.2017.1195. Epub Mar. 15, 2017. PMID: 28515924; PMCID: PMC5431311."
Yoon et al. NOTUM Is Involved in the Progression of Colorectal Cancer Cancer Genomics & Proteomics, 2018; 15:485-497.
Yu et al. Prognostic and clinicopathological significance of Cacna2d1 expression in epithelial ovarian cancers: a retrospective study. Am J Cancer Res 2016;6(9):2088-2097.
Yuan et al. "Antimicrobial peptide based magnetic recognition elements and Au@Ag-GO SERS tags with stable internal standards: a three in one biosensor for isolation, discrimination andkilling of multiple bacteria in whole blood" Chemical Science, vol. 9 (Nov. 2, 2018): pp. 8781-8795; entire document.
Yuan et al. Modification of α2, 6-sialylation mediates the invasiveness and tumorigenicity of non-small cell lung cancer cells in vitro and in vivo via Notch 1/Hes1/MMPs pathway. Int J Cancer. 2018; 143(9):2319-2330.
Zhang et al., Deep Learning-Based Multi-Omics Data Integration Reveals Two Prognostic Subtypes in High-Risk Neuroblastoma. Front. Genet., Oct. 18, 2018: vol. 9, Article 477; 1-9 Pages. https://doi.org/10.3389/fgene.2018.00477.
Zhang et al. Identification of Apolipoprotein C—I as a Potential Wilms' Tumor Marker after Excluding inflammatory factors. Int. J. Mol. Sci. 2014, 15(9), 16186-16195.
Zhang, et al., Phenotype Prediction using a Tensor Representation and Deep Learning from Data Independent Acquisition Mass Spectrometry. bioRxiv 2020.03.05.978635;1-11 Pages. doi: https://doi.org/10.1101/2020.03.05.978635.
Zhang et al. SMC4, which is essentially involved in lung development, is associated with lung adenocarcinoma progression. Scientific Reports, 2016, 6:34508.
"Zhang L, Zheng J, Ahmed R, Huang G, Reid J, Mandal R, Maksymuik A, Sitar DS, Tappia PS, Ramjiawan B, Joubert P, Russo A, Rolfo CD, Wishart DS. A High-Performing Plasma Metabolite Panel for Early-Stage Lung Cancer Detection. Cancers (Basel). Mar. 7, 2020;12(3):622. doi: 10.3390/cancers12030622. PMID: 32156060; PMCID: PMC7139410."
"Zhang S., Che D., Yang F., Chi C., Meng H., Shen J., Qi L., Liu F., Lv L., Li Y., Meng Q., Liu J., Shang L., et al Tumor-associated macrophages promote tumor metastasis via the TGF-β/SOX9 axis in non-small cell lung cancer. Oncotarget. 2017; 8: 99801-99815. Retrieved from https://www.oncotarget.com/article/21068/text/".
Zhu et al., Apolipoprotein M promotes proliferation and invasion in non-small cell lung cancers via upregulating S1PR1 and activating the ERK1/2 and PI3K/AKT signaling pathways. Biochemical and Biophysical Research Communications, 2018, 501(2):520-526.
Agajanian, et al., Integration of Random forest classifiers and deep convolutional neural networks for classification and Biomolecular modeling of cancer driver mutations. Frontiers in molecular biosciences 6 (2019): 44. Jun. 11, 2019, Retrieved on Oct. 30, 2022. From https://www.frontiersin.org/articles/10.3389/fmolb.2019.00044/full entire document.
Co-pending U.S. Appl. No. 18/164,446, inventors Ma; Philip et al., filed Feb. 3, 2023.
Correia, et al., Machine learning modeling of blood lipid biomarkers in familial hypercholesterolaemia versus polygenic/environmental dyslipidaemia. Nature portfolio, Scientific Reports (2021) 11:3801; 9 Pages.
Katzke, et al., Blood lipids and lipoproteins in relation to incidence and mortality risks for CVD and cancer in the prospective EPIC-Heidelberg cohort, BMC Medicine (2017) 15:218; 13 Pages.
Liu, et al., Machine Learning Protocols in Early Cancer Detection Based on Liquid Biopsy: A Survey. Life 2021, 11, 638,39 Pages. https://doi.org/ 10.3390/life11070638.
Nguyen, et al., Protein corona: a new approach for nanomedicine design, International Journal of Nanomedicine 2017:12; 3137-3151.
PCT/US2022/076125 International Search Report and Written Opinion dated Jan. 12, 2023.
Ritz, et al.,, Protein Corona of Nanoparticles: Distinct Proteins Regulate the Cellular Uptake, Biomacromolecules 2015:16(4); 1311-1321 DOI: 10.1021/acs.biomac.5b00108.
Trivedi et al. Risk assessment for indeterminate pulmonary nodules using a novel, plasma-protein based biomarker assay. Biomed Res Clin Pract 2018, 3(4), pp. 1-17 (Year: 2018).
U.S. Appl. No. 17/709,202 Office Action dated Jan. 26, 2023.
Zhang et al., Phenotype Classification using Proteome Data in a Data-Independent Acquisition Tensor Format. J Am Soc Mass Spectrom. Nov. 4, 2020;31(11):2296-2304. doi: 10.1021/jasms.0c00254. Epub Oct. 26, 2020. PMID: 33104352.
Co-pending U.S. Appl. No. 18/095,422, inventors Wilcox; Bruce et al., filed Jan. 10, 2023.
Co-pending U.S. Appl. No. 18/165,264, inventor Manway; Liu, filed Feb. 6, 2023.
"SEER, Inc. Form 10-Q for Quarterly period ended Jun. 30, 2021." EDGAR. Securities and Exchange Commission, 2021, https://www.sec.gov/ix?doc=/Archives/edgar/data/0001726445/000162828021016865/seer-20210630.htm.
Kuang, M. et al., Proteomic analysis of plasma exosomes to differentiate malignant from benign pulmonary nodules. Clin Proteom 16, 5 (2019). https://doi.org/10.1186/s12014-019-9225-5.
Li, Xiao-jun et al., A Blood-Based Proteomic Classifier for the Molecular Characterization of Pulmonary Nodules. Sci Transl Med. Oct. 16, 2013; 5(207): 207ra142. doi:10.1126/scitranslmed.3007013.
Pearson, Ryan M., Vanessa V. Juettner, and Seungpyo Hong. "Biomolecular corona on nanoparticles: a survey of recent literature and its implications in targeted drug delivery." Frontiers in chemistry 2 (2014): 108.
Shriwash et al., Identification of differentially expressed genes in small and non-small cell lung cancer based on meta-analysis of mRNA, 2019, Heliyon, 5, p. 1-9 (Year: 2019).
U.S. Appl. No. 17/585,303 Office Action dated Mar. 6, 2023.
U.S. Appl. No. 17/709,185 Office Action dated Mar. 16, 2023.
U.S. Appl. No. 18/095,422 Office Action dated Apr. 14, 2023.
Walkey et al. ("Protein Corona Fingerprinting Predicts the Cellular Interaction of Gold and Silver Nanoparticles," ACS Nano, vol. 8, No. 3, pp. 2439-2455, published 2014) (Year: 2014).

(56) References Cited

OTHER PUBLICATIONS

Wan et al. ("Highly Specific Electrochemical Analysis of Cancer Cells using Multi-Nanoparticle Labeling," Angew. Chem. Int. Ed. 2014, vol. 53, pp. 13145-13149) (Year: 2014).
Brinkmann et al., Oral squamous cell carcinoma detection by salivary biomarkers in a Serbian population, Oral Oncology, vol. 47(1), 2011: pp. 51-55.
Cruz et al., Applications of Machine learning in cancer prediction and prognosis (Cancer Informatics, 2006, vol. 2, pp. 59-77).
GB2205374.8 Examination Report dated Apr. 19, 2023.
Kopac. Protein corona, understanding the nanoparticle-protein interactions and future perspectives. International Journal of Biological Macromolecules 2021, vol. 169, pp. 290-301, published online Dec. 21, 2020 (Year: 2020).
Melone. Seer debuts with proprietary proteomics platform to enable early detection of cancer and neurological diseases. Businesswire 2018, pp. 1-5 (Year: 2018).
Mishra et al. Biological effects of formation of protein corona onto nanoparticles. International Journal of Biological Macromolecules 2021, vol. 175, pp. 1-18, published on line Jan. 21, 2021 (Year: 2021).
PCT/US2023/063358 International Search Report and Written Opinion dated Aug. 1, 2023.
Tanigawa et al. Upregulation of ANGPTL6 in mouse keratinocytes enhances susceptibility to psoriasis. Sci Rep. Oct. 4, 2016;6:34690. doi: 10.1038/srep34690. PMID.
U.S. Appl. No. 17/585,303 Notice of Allowance dated Apr. 26, 2023.
U.S. Appl. No. 17/709,185 Office Action dated Jun. 15, 2023.
U.S. Appl. No. 17/709,202 Office Action dated May 10, 2023.
U.S. Appl. No. 17/720,197 Office Action dated Aug. 11, 2023.
U.S. Appl. No. 18/095,422 Office Action dated Jun. 13, 2023.
U.S. Appl. No. 18/150,390 Office Action dated Jul. 5, 2023.
U.S. Appl. No. 18/164,446 Office Action dated Jul. 19, 2023.
U.S. Appl. No. 18/165,264 Office Action dated Aug. 11, 2023.
U.S. Appl. No. 17/585,303 Notice of Allowance dated Apr. 14, 2023.
Zeng et al., Integrative Models of Histopathological Image Features and Omics Data Predict Survival inHead and Neck Squamous Cell Carcinoma, Frontiers in Cell and Development Biology, 2020; vol. 8: p. 55309, Available online at: https://www.frontiersin.org/articles/10.3389/fcell.2020.553099/full [accessed Apr. 14, 2023].
Hsu, T. et al., Plasma-based detection of pancreatic cancer: A multiomics approach. Poster presented at the 2021 AACR virtual special conference: Pancreatic cancer, Sep. 29-30, 2021; 10 Pages.
Lennon, A. M. et al., Feasibility of blood testing combined with PET-CT to screen for cancer and guide intervention. Science 369, eabb9601 (2020). DOI: 10.1126/science. abb9601.
Lin, C. J. et al., Evaluation of a sensitive blood test for the detection of colorectal advanced adenomas in a prospective cohort using a multiomics approach. Poster Presented at the 2021 Gastrointestinal Cancers Symposium. 1 Page.
Putcha, G. et al., Blood-based detection of early-stage colorectal cancer using multiomics and machine learning. Poster presented at American Society of Clinical Oncology. 2020, 1 Page.
Husi, H. et al., Identification of diagnostic upper gastrointestinal cancer tissue type-specific urinary biomarkers, Biomedical Reports 10:165-174 (2019).
Jin, Y. et al., Alpha-1-antichymotrypsin as a novel biomarker for diagnosis, prognosis, and therapy prediction in human diseases, Cancer Cell International 22(156), 12 pages (2022).
Nie, S. et al. Glycoprotein biomarker panel for pancreatic cancer discovered by quantitative proteomics analysis. Journal of proteome research 13, 1873-1884 (2014).
Nie, S. et al., Quantitative Analysis of Single Amino Acid Variant Peptides Associated with Pancreatic Cancer in Serum by an Isobaric Labeling Quantitative Method, Journal of Proteome Research 13:6058-6066 (2014).
PCT/US2023/067945 International Search Report and Written Opinion dated Dec. 20, 2023.
PCT/US2023/073688 International Search Report and Written Opinion dated Dec. 15, 2023.
PubChem CID 155887589. Create Date: Apr. 22, 2021, https://pubchem.ncbi.nlm.nih.gov/compound/155887589 Date Accessed: Nov. 28, 2022 (Nov. 28, 2022), p. 2.
Roberts, A.S. et al., Identification of Potential Prognostic Biomarkers in Patients With Untreated, Advanced Pancreatic Cancer From a Phase 3 Trial (Cancer and Leukemia Group B 80303), Cancer 118:571-578 (2012).
U.S. Appl. No. 17/709,185 Office Action dated Oct. 5, 2023.
Wu, W. et al., Solid Serous Cystadenoma of the Pancreas: A Case Report of 2 Patients Revealing Vimentin, beta-Catenin, alpha-1 Antitrypsin, and alpha-1 Antichymotrypsin as New Immunohistochemistry Staining Markers, Medicine 94(12):1-4 (Mar. 2015).
Yang et al. Cleavable Trifunctional Biotin Reagents for Protein Labelling, Capture and Release. Chemical Communications. vol. 49 (2013): 3 pages.
Zacharias L .G et al.,"HILIC and ERLIC Enrichment of Glycopeptides Derived from Breast and Brain Cancer Cells",Journal of proteome research, vol. 15(10), 2016, pp. 3624-3634.
Blume, J.E. et al., Validated Pancreatic Ductal Adeno Carcinoma Classifier Based on a Panel of Proteins Measured in Plasma with a Targeted Mass Spectrometry Assay in a Case-Control Study of 182 Subjects, Patent Application Disclosure Memo, PrognomiQ, Inc., 33 pages (Aug. 31, 2022).
Haan, T.J. et al., A repeat pattern of founder events for SARS-CoV-2 variants in Alaska, medRxiv, The Preprint Server for Health Sciences, 5 pages (2022).
Hua, S. et al., Site-specific protein glycosylation analysis with glycan isomer differentiation, Anal Bioanal Chem 403:1291-1302 (2012).
Zhu, H. et al., A LC-MS All-in-One Workflow for Site-Specific Location, Identification and Quantification of N-/O-Glycosylation in Human Chorionic Gonadotropin Drug Products, The AAPS Journal, 10 pages (2017).

\* cited by examiner

All features

Proteograph
AUC=0.83±0.11
Lipid
AUC=0.76±0.12
Proteograph+lipid
AUC=0.82±0.10
ProteinQuant
AUC=0.88±0.09
Proteograph+ProteinQuant
AUC=0.90±0.08
Proteograph+lipid+
ProteinQuant
AUC=0.87±0.09

Top 20 features

Proteograph
AUC=0.78±0.12
Lipid
AUC=0.76±0.12
Proteograph+lipid
AUC=0.82±0.11
ProteinQuant
AUC=0.82±0.11
Proteograph+ProteinQuant
AUC=0.86±0.10
Proteograph+lipid+
ProteinQuant
AUC=0.86±0.10

All features

Proteograph
AUC=0.83±0.11
Lipid
AUC=0.76±0.12
Proteograph+lipid
AUC=0.82±0.10
ProteinQuant
AUC=0.88±0.09
Proteograph+ProteinQuant
AUC=0.90±0.08
Proteograph+lipid+
ProteinQuant
AUC=0.87±0.09

Top 20 features

Proteograph
AUC=0.78±0.12
Lipid
AUC=0.76±0.12
Proteograph+lipid
AUC=0.82±0.11
ProteinQuant
AUC=0.82±0.11
Proteograph+ProteinQuant
AUC=0.86±0.10
Proteograph+lipid+
ProteinQuant
AUC=0.86±0.10

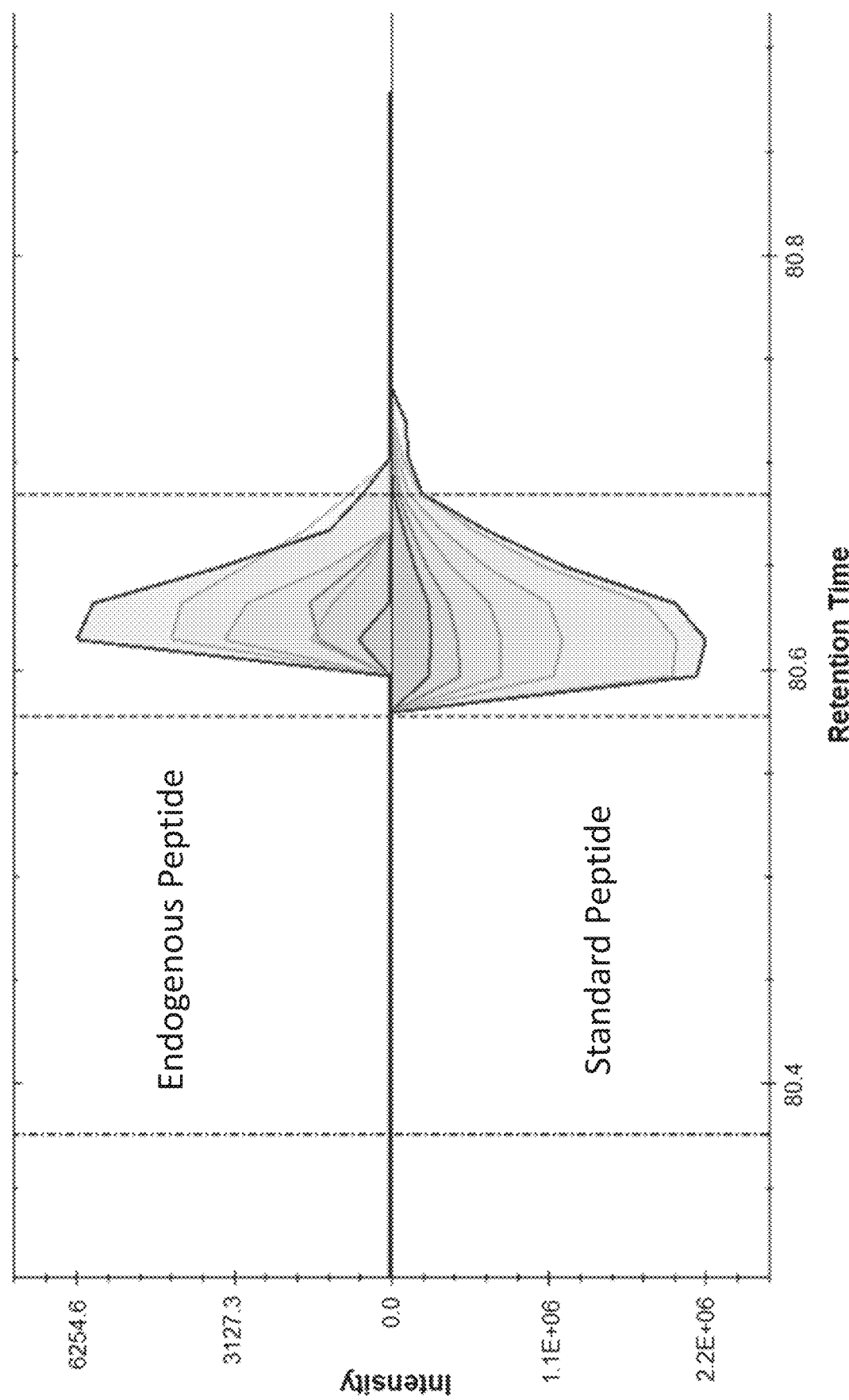

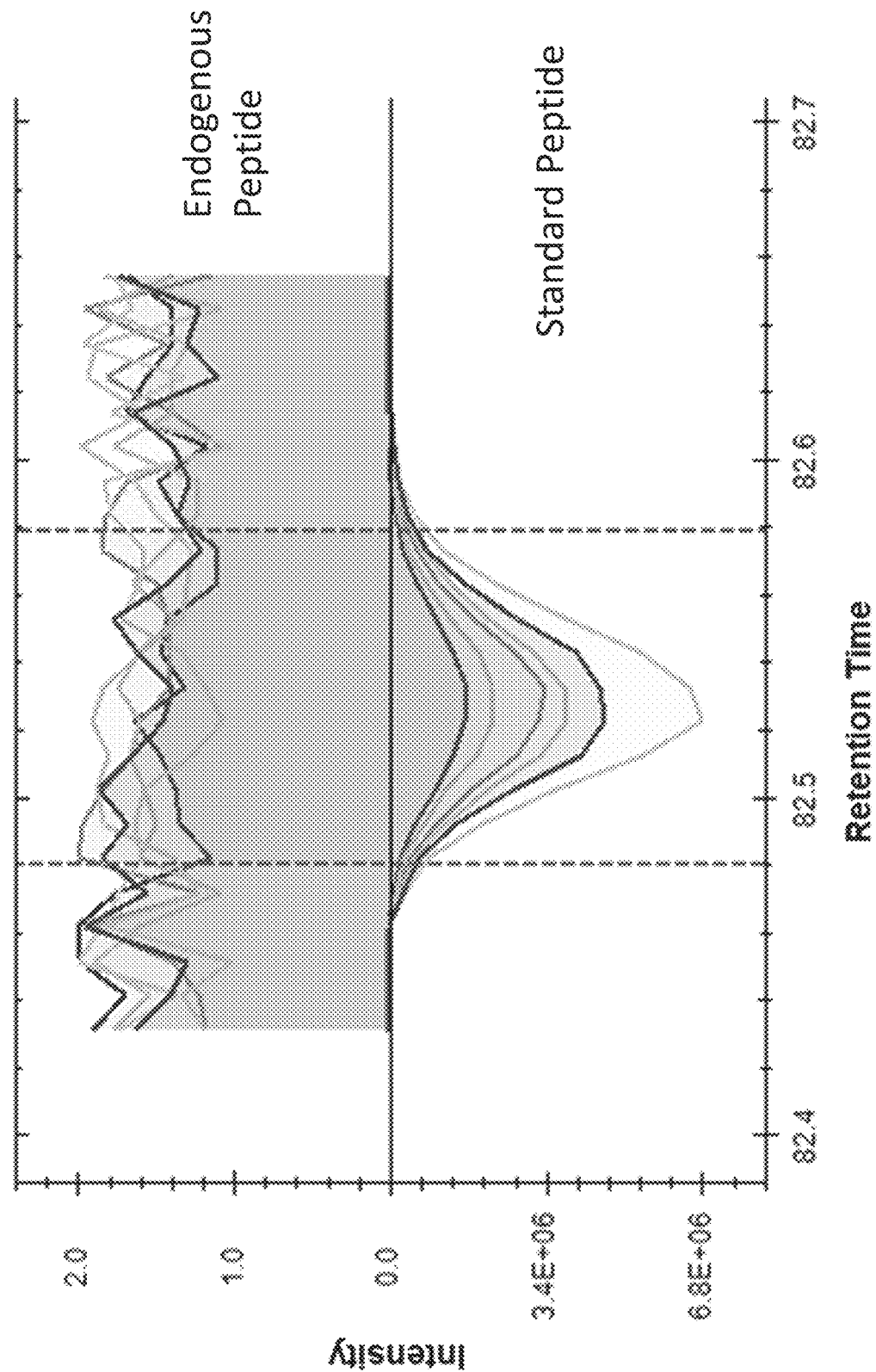

ENHANCED DETECTION AND QUANTITATION OF BIOMOLECULES

CROSS-REFERENCE

This application claims priority to U.S. Provisional Application No. 63/243,645 filed on Sep. 13, 2021, the content of which is incorporated herein in its entirety.

BACKGROUND

There is a need for methods of accurately detecting a disease or condition, such as at an early stage of the disease or condition. Accurately detecting a disease or condition can be used in effective treatments and improved prognosis of a subject.

SUMMARY

Disclosed herein, in some aspects, are methods comprising: contacting a biological sample of a subject with particles, thereby adsorbing endogenous biomolecules of the biological sample to the particles; and combining the biological sample or the adsorbed endogenous biomolecules with internal standards of the biomolecules. The internal standards may comprise a label. Some aspects include comprising measuring the endogenous biomolecules and the internal standards to obtain endogenous biomolecule measurements and internal standard measurements. Some aspects include identifying concentrations of the endogenous biomolecules based on the internal standard measurements. Some aspects include determining a quality control aspect of the endogenous biomolecule measurements based on measurements of the internal standard measurements. In some aspects, the biological sample comprises a group of biological samples, measuring the endogenous biomolecules comprises measuring the endogenous biomolecules of the group of biological samples, and the quality control aspect is in relation to the endogenous biomolecules of the group of biological samples. In some aspects, the quality control aspect comprises a mass accuracy, quantitative precision, quantitative accuracy, correlation with a standard sample, chromatographic performance, corona formation quality, digestion quality, or a contaminant biomolecule measurement. In some aspects, the measurements are obtained by a mass spectrometer. Some aspects include performing real-time control of the mass spectrometer based on the internal standard measurements, or based on the quality control aspect. In some aspects, performing real-time control of the mass spectrometer comprises adjusting internal voltages to provide a change in specificity, adjusting a sample volume, adjusting a technical condition to improve measurement quality, pausing or stopping data collection, rescheduling a measurement, or notifying a user of a quality control issue. Some aspects include normalizing or adjusting the endogenous biomolecule measurements based on the internal standard measurements. In some aspects, the endogenous biomolecule measurements comprise an amount of the endogenous biomolecules in the biological sample. Some aspects include determining an amount of the endogenous biomolecules adsorbed to the particles relative to the amount of the endogenous biomolecules in the biological sample. Some aspects include identifying a source of variability in the endogenous biomolecule measurements based on the internal standard measurements. Some aspects include using the internal standard measurements to identify or obtain additional endogenous biomolecule measurements. Some aspects include identifying a biological state of the subject based on the endogenous biomolecule measurements. Some aspects include outputting or transmitting a report comprising information on the identified biological state. Some aspects include transmitting or outputting a recommendation of a treatment of the subject based on the identified biological state. In some aspects, the subject is suspected of having the biological state. In some aspects, the biological state comprises a disease state. In some aspects, the disease state comprises cancer. In some aspects, the cancer comprises stage 1 or stage 2 cancer. In some aspects, the cancer comprises lung cancer. In some aspects, the lung cancer comprises non-small cell lung cancer. In some aspects, the biomolecules comprise proteins, lipids, metabolites, sugars, or nucleic acids. In some aspects, the biomolecules comprise proteins. In some aspects, the internal standards comprise an isotopic label, a mass tag, a barcode, a post-translation modification, or a biomolecule from a species different than a species of the subject. In some aspects, the particles comprise nanoparticles. In some aspects, the particles comprise a metal, polymer, or lipid. In some aspects, the particles comprise physiochemically distinct groups of particles. In some aspects, the first biological sample or the second biological sample comprises a biofluid. In some aspects, the biofluid comprises blood, serum, or plasma. In some aspects, the subject is an animal. In some aspects, the subject is a vertebrate. In some aspects, the subject is a mammal. In some aspects, the subject is a human.

Disclosed herein, in some aspects, are classification methods, comprising: obtaining a first data set comprising first measurements of biomolecules adsorbed to particles from a first biological sample of a subject; obtaining a second data set comprising second measurements of the biomolecules of the first biological sample or of a second biological sample of the subject, wherein the second measurements comprise measurements of individual endogenous biomolecules normalized or adjusted based on measurements of labeled reference biomolecules combined with the first biological sample or combined with the second biological sample; applying a first classifier to assign a first label corresponding to a biological state to the first data set; applying a second classifier to assign a second label corresponding to the biological state to the second data set; and combining the first label and the second label to obtain a combined label corresponding to the biological state. Disclosed herein, in some aspects, are methods, comprising: obtaining measurements of endogenous biomolecules adsorbed to particles from a biological sample of a subject; obtaining measurements of labeled reference biomolecules combined with the biological sample, or combined with the endogenous biomolecules adsorbed to the particles, wherein the labeled reference biomolecules are the same as the endogenous biomolecules but also comprise a label; and normalizing or adjusting the measurements of the endogenous biomolecules based on the measurements of the labeled reference biomolecules. Some aspects include applying a classifier to the normalized or adjusted measurements to assign a label corresponding to a biological state to the normalized or adjusted measurements. Disclosed herein, in some aspects, are methods, comprising contacting a biological sample of a subject with particles, thereby adsorbing endogenous biomolecules of the biological sample to the particles; and combining the biological sample or the adsorbed endogenous biomolecules with labeled reference biomolecules, wherein the labeled reference biomolecules are the same as the endogenous biomolecules but further comprise a label. Some aspects include measuring the endogenous biomolecules and the labeled reference biomolecules. Some aspects include obtaining a first data set comprising first measurements of biomolecules adsorbed to particles from a first biological sample of a subject. Some aspects include obtaining a second data set comprising second measurements of biomolecules of the first sample or a second biological sample of the subject. In some aspects, labeled reference biomolecules are combined with the first or second sample, measured together with the biomolecules, and used to obtain the second measurements. Some aspects include using a first classifier to assign a first label corresponding to a presence, absence, or likelihood of a disease state or biological state to the first data set. Some aspects include using a second classifier to assign a second label corresponding to a presence, absence, or likelihood of the disease state or biological state to the second data set. Some aspects include identifying the data sets as indicative or as not indicative of the disease state or biological state based on a combination of the first and second labels. In some aspects, the biomolecules comprise proteins, lipids, metabolites, sugars, or nucleic acids. In some aspects, the biomolecules comprise proteins. In some aspects, the first or second measurements comprise measurements of at least about 500 biomolecules. In some aspects, the first or second measurements are obtained using mass spectrometry, chromatography, a lateral flow assay, an immunoassay, or a combination thereof. In some aspects, the first or second measurements are obtained using mass spectrometry. In some aspects, the first or second measurements are obtained by measuring a readout indicative of the presence, absence or amount of the biomolecules. In some aspects, the method comprises contacting the first sample with the particles to adsorb the biomolecules to the particles, and measuring the adsorbed biomolecules. In some aspects, the adsorbed biomolecules are separated from the particles before the first measurements are obtained. In some aspects, the particles comprise nanoparticles. In some aspects, the particles comprise a metal, polymer, or lipid. In some aspects, the particles comprise physiochemically distinct groups of particles. In some aspects, the method comprises combining the first or second sample with the reference biomolecules, measuring the reference biomolecules with the biomolecules, and using the reference biomolecules to obtain the second measurements. In some aspects, the reference biomolecules are isotopically labeled. In some aspects, the reference biomolecules are combined in a predetermined amount with the first or second sample In some aspects, the reference biomolecules are used to identify mass spectra of biomolecules, and to obtain the second measurements from the mass spectra of the biomolecules. In some aspects, the reference biomolecules are used to normalize or adjust measurements of the biomolecules, to obtain the second measurements. In some aspects, the second measurements are obtained from the first sample. In some aspects, the reference biomolecules are combined with the first sample and the second measurements are obtained after the first sample has been contacted with the particles to adsorb biomolecules to the particles and the first measurements have been obtained. In some aspects, the reference biomolecules are combined with the first sample and the second measurements are obtained before the first sample has been contacted with the particles to adsorb biomolecules to the particles and the first measurements have been obtained. In some aspects, the second measurements are obtained separately from the first measurements, in an aliquot or aliquant of the first sample. In some aspects, the second measurements are obtained from the second sample. Some aspects include contacting the biomolecules with an affinity reagent to enrich the biomolecules. In some aspects, the affinity reagent comprises an antibody. In some aspects, the first and second labels comprise likelihoods of the disease state. Some aspects include averaging the likelihoods. In some aspects, identifying the data sets as indicative or as not indicative of the disease state comprises generating a majority voting score based on the first and second labels. Some aspects include identifying the data sets as indicative or as not indicative of the disease state comprises generating a weighted average of the first and second labels. Some aspects include assigning weights to the first and second classifiers, thereby obtaining the weighted average. In some aspects, the weights are assigned based on area under a ROC curve, area under a precision-recall curve, accuracy, precision, recall, sensitivity, F1-score, specificity, or a combination thereof. In some aspects, the first and second classifiers err independently of one another with regard to the disease state. In some aspects, the combination of the first and second labels identifies the data sets as indicative or as not indicative of the disease state with greater accuracy than the first or second label alone. Some aspects include outputting or transmitting a report comprising information on the identification. Some aspects include transmitting or outputting a recommendation of a treatment of the subject based on the disease state. Some aspects include comprising providing a treatment for the disease state to the subject when the data sets are identified as indicative of the disease state. Some aspects include observing the subject without providing the treatment when the data sets are identified as not indicative of the disease state. Some aspects include obtaining a third data set comprising measurements of a different type of biomolecules than the biomolecules of the first and second measurements. Some aspects include using a third classifier to assign a third label corresponding to a presence, absence, or likelihood of a disease state to the third data set. In some aspects, the method comprises identifying the first, second, and third data sets as indicative or as not indicative of the disease state based on a combination of the first and second labels. In some aspects, the disease state comprises cancer. In some aspects, the cancer comprises stage 1 or stage 2 cancer. In some aspects, the cancer comprises lung cancer. In some aspects, the lung cancer comprises non-small cell lung cancer. In some aspects, the sample comprises a biofluid. In some aspects, the biofluid comprises blood, serum, or plasma. In some aspects, the subject is an animal. In some aspects, the subject is a vertebrate. In some aspects, the subject is a mammal. In some aspects, the subject is a human.

BRIEF DESCRIPTION OF THE DRAWINGS

FIG. 9A is a plot illustrating an example of a protein identified using an isotopically labeled heavy internal standard that was not identified by a discovery mass spectrometry experiment without the internal standard.

FIG. 9B is a plot illustrating an example of a protein not identified using an isotopically labeled heavy internal standards or by a discovery mass spectrometry experiment without the internal standard, and where the presence of the peak by the internal standard was used to confirm that the protein was absent in the sample.

DETAILED DESCRIPTION a. Introduction

Figure 1:
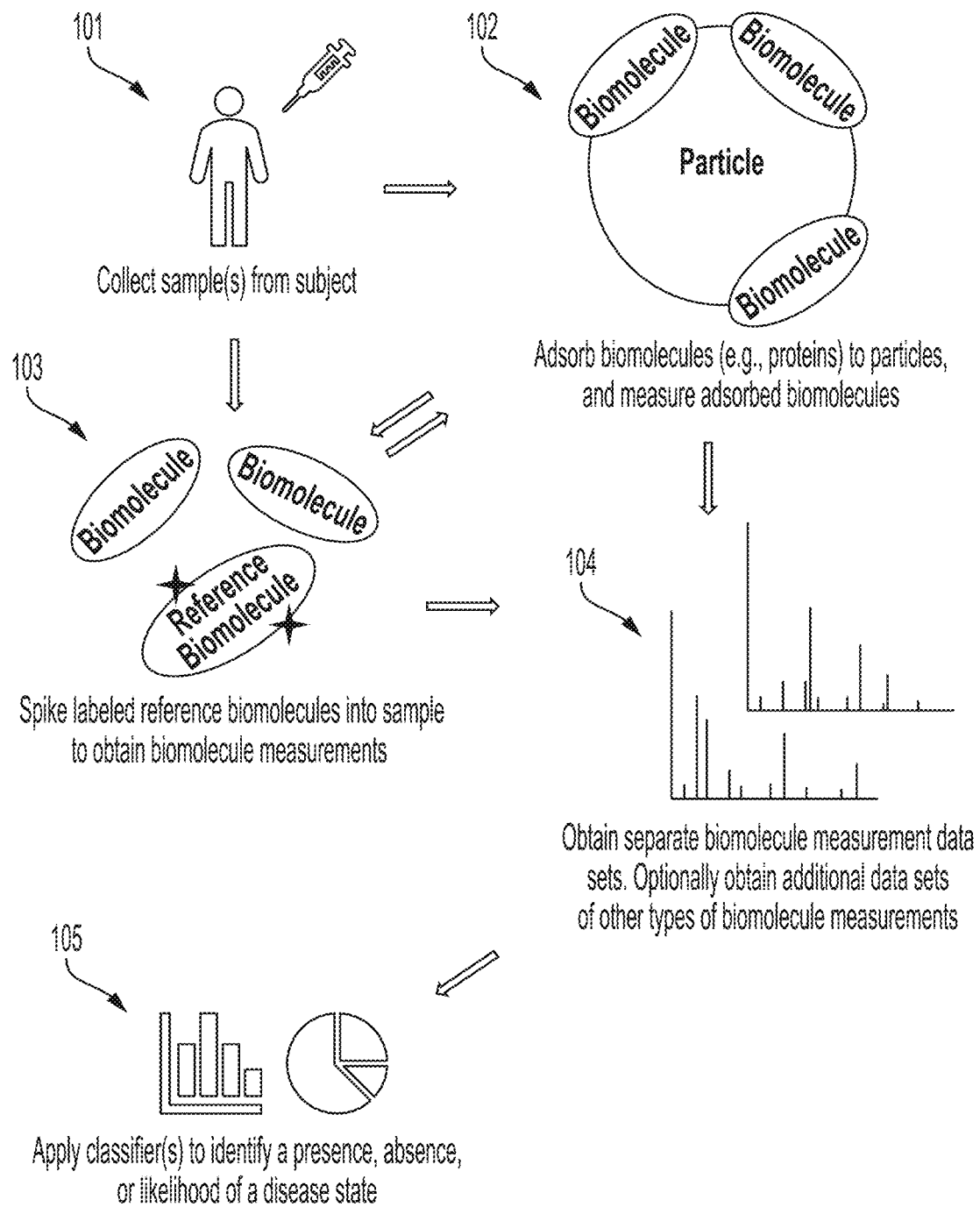
FIG. 1 is a flowchart depicting an example of a method disclosed herein.

The disclosure provided herein describes methods, systems, and compositions for improved detection and quantification of biomolecules in a biological sample. Despite advances in measurement of biomolecules, misclassification of samples occurs, and more advanced methods are needed. Combining separate sets of measurements of a given type of biomolecule may result in a reduced signal to noise ratio, and overall improved data quality. Spiking labeled internal standard biomolecules into a sample improves identification and measurement of endogenous biomolecules. Use of particles in assaying biomolecules also improves biomolecule measurement, for example, measurement of low abundance biomolecules when high abundance biomolecules would normally interfere with an accurate measurement of the low abundance biomolecules. The combined use of measurements obtained using labeled internal standards and measurements obtained using particles that may be determination of levels improves classification of biological samples (e.g., with respect to biological state).

There is no currently available method for determination of (1) the variability in sample mass (e.g. μg) and quality prior to nanoparticle enrichment of biomolecules when adsorbing biomolecules to nanoparticles, (2) direct measurement of the recovery of total sample and individual biomolecules following nanoparticle enrichment (3) validation of biomolecules detected after nano-particle enrichment, (4) data driven real-time decision on improving data quality within a measurement, (5) data driven decision to collect additional data based on detection of biological differences (e.g. PTM, SNP, or quantitation), or 5) assessment of health status(s) by comparison of quantitative data against a database of quantitative values and classifiers. This disclosure solves this need through the incorporation of internal controls into samples prior to or after enrichment of biomolecules with nanoparticles. For example, a method of this disclosure may include addition of internal standards at known concentrations into biological and control samples for the quantitation of known peptides/proteins, utilization of internal standards for determination of sample quality, or utilization of differences in quantitative peptide/protein concentrations to collect additional biological data from a single sample either in real time or through serial data collections.

This disclosure includes methods for proteomic and multi-omic biomarker discovery from a biological sample, which may include interrogating the biological sample (e.g. plasma) with nanoparticles and then re-interrogating the same biological sample with a set of reagents that are specifically designed to detect and quantify levels of specific peptides of various proteins that may be in the biological sample. Thus, the method may include complementary proteomic sampling of the same biological sample. This method was performed with lung cancer samples, and improved classification was obtained when using the two types of proteomic sampling versus only one alone. Moreover, when data from other analytes such as lipidomics was further included, the combined classification method was improved compared to one of the proteomic samples alone plus the other analyte. The method may include using the specialty reagents to measure some of the proteins that are adsorbed to nanoparticles. This may improve the detection, quantification, and reproducibility of measurement of proteins adsorbed to the nanoparticles.

Useful aspects of the methods disclosed herein may include the ability to remove uncertainty of what molecules are detected after processing with particles or nanoparticles, improvement in quantitative measurement (e.g. precision or accuracy) of biomolecules processed with nanoparticles, increasing a number of unique biomolecules measured after processing with nanoparticles, improved assessment of the quality (e.g. reproducibility or recovery) of nanoparticle enrichment of biomolecules, or the ability to provide real-time detection of additional biological information in a single sample as a function of diverse, unique, quantitative peptide/protein measurements.

This disclosure includes non-invasive methods for determining a presence or absence of a disease state. Identifying the disease state in a subject at an early-stage can prevent further development of the disease if treatment is provided. The methods described may be used non-invasively, and can thereby be used to rule out the presence of the disease state, and save the subject from having to undergo a biopsy.

Accordingly, described herein are methods that include generating multiple data sets from one or more biological samples of a subject. The data sets may include measurements of different types of biomolecules (e.g. different omic data sets), or different measurements of the same type of biomolecule. For example, one data set may include measurements of proteins or another biomolecule type using particles or nanoparticles, and a second data set may include measurements of the same type of biomolecule (e.g. proteins) generated upon inclusion of a reference biomolecule in a sample. The reference biomolecule may include an internal standard biomolecule, and may be labeled. One or more classifiers may then be used to determine the presence of the disease state using the data sets.

Non-invasively obtained samples can be used for disease classification by generating multiple data sets from one or more samples, and the accuracy of disease identification or prediction may be improved by combining multiple data sets. The methods described herein can be used for improved measurement of proteomic, metabolomic, or lipidomic data, and improved sample classification. Sample classification may be provided in the form of a biomedical report. The biomedical report can provide an indication of whether the subject from which the sample is obtained has cancer or other disease.

FIG. 1 illustrates a non-limiting example for data classification. The method may be used to predict whether a subject has or is at risk of developing a disease based on assaying and analyzing a biological sample obtained from the subject. The method may include collecting one or more biological samples from the subject (101). The samples may be used to obtain biomolecule measurements. One set of biomolecule measurements may be obtained through the use of particles (102), and another set of biomolecule measurements may be obtained through the use of reference biomolecules (103). 102 and 103 may be performed in sequence to the same biological sample, or may be performed separately with separate biological samples. A reference biomolecule can be added to the biological sample before or after biomolecules are adsorbed to the particles, or may be added to a separate biological sample of the subject. The measurements may be used to generate data sets (104). Additional types of biomolecule measurements may be included among the data sets. For example, 102 and 103 may be used to generate proteomic data, and additional data sets may include transcriptomic data, genomic data, metabolomic data, or lipidomic data. The method may include receiving the measurements or data sets. The data sets are then analyzed by applying one or more classifiers to identify the data as indicative of a presence, absence, or likelihood of a disease state of the subject or sample (105). The data may be combined and one classifier may classify the data, or multiple classifiers may be used to separately classify each data set followed by an integration of the outputs of the classifiers.

The method may include adding a set of peptide or protein internal standards to samples processed utilizing nanoparticles. The peptides or proteins may be a subset of proteins or proteoforms that are otherwise endogenous to the sample. The set of peptides or proteins may include exogenous proteins and peptides. Use of this set of peptides or proteins is further described below with regard to use of reference biomolecules. In some aspects, the peptide or protein internal standard can be heavy-labeled (e.g., labeled with isotope). In some aspects, the peptide or protein internal standard can be protein or peptide with at least one tag (e.g., for barcoding or for mass spectrometry). In some aspects, the peptide or protein internal standard can be protein or peptide with at least one tag, where the at least one tag comprises a post-translation modification (PTM), a chemical modification, a barcode, or a combination thereof. In some aspects, the peptide or protein internal standard is from non-human species. In some aspects, the peptide or protein internal standard can establish concentrations of the individual peptides and proteins in the sample. In some aspects, the peptide or protein internal standards can be added at a predetermined or known concentration to all, or a sub-set of, samples processed utilizing nano-particles are used to calculate the concentration of each endogenous protein. In some aspects, either all, or a sub-set of, the internal standards can be added either prior or after processing samples by nano-particles to be used to determine a variety of quality control metrics. mass accuracy; quantitative precision; quantitative accuracy; correlation with known standard samples or standards (i.e. Pearson correlation, Demming regression, etc); chromatographic performance (i.e. Retention Time, Peak Width, FWHM, Peak Asymmetry, Peak Capacity, etc); coronal formation quality; digestion quality (i.e. missed cleavages, oxidation rate, etc); or measurement and control of known "contaminant" proteins that are routinely encountered in proteomic sample preparation workflows. FIGS. 5A-5D illustrate various measurements with the internal standards described herein.

In some aspects, the method comprises rescheduling of individual samples and control samples to collect additional data either after instrument adjustments (i.e. voltages, etc.) or instrument maintenance (i.e. cleaning). Additional data collection could be additional quantitative data, biological data, or technical data (i.e. adjustment of fragmentation energy). In some aspects, the method comprises automated notification messages sent directly to users by various means as a warning that any QC performance threshold limits are being approached or surpassed. In some aspects, the method comprises normalization of 2 or more samples through the use of either measured quantitative values of the internal standards. In some aspects, the method comprises adding internal standards to each sample either prior to after the processing by nano-particles. In some aspects, the method comprises adding internal standards to control samples (technical or biological) to provide known reference values. A variety of techniques (i.e. median, LOESS, etc.) can be used to normalize differences in response as a function of processing by nano-particles and/or measurement by mass spectrometry.

In some aspects, the method comprises determining the recovery of each protein for understanding of protein losses on each nano-particle as a function of corona formation or PPI and available individual protein concentration after processing by nano-particles for increased accuracy for quantitation. In some aspects, the method comprises establishing the biological concentrations of proteins and proteoforms in individual patient samples. If a protein is detected, or detected above a desired threshold, then the mass spectrometer can be directed to collect additional MS/MS data on predicted PTM and genetically modified version of the same peptide/protein. The concentration of all unique peptides for a given protein can be either up or down regulated in the same direction vs a reference concentration (i.e. control samples). When a discordant peptide is detected, then the instrument can be controlled in real time to collect data on the genetically modified version of the peptide (pre-calculated in a database). The discordant peptide could be due to either genetic modification (i.e. SNP) or PTM (e.g. glycosylation or phosphorylation). The additional data collected can be based on a database of predicted mass, retention times, CCS, Kendrick Mass Defect and predicted energy required to sequence the desired peptide (e.g., fragmentation modality and energy). The mode and energy of fragmentation can be determined based on the predicted modification one is attempting to detect (i.e. EAD/ETD for glycosylated proteins vs CID for SNP modified peptides).

In some aspects, the method comprises data driven detection of individual genetic fingerprints based on confirmed detection of unique peptides/proteins with and without genetic modification utilizing internal standards in an individual sample. For every confirmed protein detection, the mass spectrometer can be controlled to collect data from predicted genetically modified peptide sequences from either an individual, or panel of, peptide(s)/protein(s) detected with internal standards.

In some aspects, the method comprises data driven detection of an individual's response to a given therapy. In some aspects, the method comprises confirmed detection with internal standards and nano-particles of unique set of peptides/proteins associated with response/non-response to a particular treatment for either a known, or determined, health status (e.g., NSCLC). In some aspects, the method comprises determination of one or multiple health status(s) through the quantitative peptide and protein measurements, comparison to known pattern of peptide and protein concentrations, and assessment. Health status call can be based on the concentrations of multiple peptides/proteins in a single sample.

In some aspects, the combination of: enrichment of the biomolecule by utilizing nanoparticles; and the use of internal standard allows detection of the biomolecule present in the biological sample at a low abundance. In some aspects, the heavy-labeled internal standard can be added to the biological sample before the biological sample is contacted with a nanoparticle (e.g. for enriching and adsorbing the biomolecule by the nanoparticle). In some aspects, the heavy-labeled internal standard can be added to the biological sample after the biological sample is contacted with a nanoparticle (e.g. for enriching and adsorbing the biomolecule by the nanoparticle).

The method may include addition of isotopically labelled biomolecules to facilitate targeted biomolecule measurement to improve depth of nanoparticle enriched samples measured. The method may include a quality control (QC) pipeline for the real-time or post analysis data quality assessment involving multiple QC molecules added at various steps along the processing process. The method may include a QC procedure for samples process by nanoparticle enrichment. Protein controls may be added before sample processing, and may include non-human proteins, isotopically labeled proteins, or synthetic non-native proteins (proteins found not in nature). The isotopically labeled proteins may include non-modified proteins, post-translationally modified proteins, or other modified proteins. Post-processing controls such as synthetic peptides may be included. The synthetic peptides may include non-modified proteins, post-translationally modified proteins, other modified proteins, or mass reporter modified proteins.

The method may include quantifying an amount of at least a first peptide, or a first peptide and a second peptide, in a biological sample. The method may include contacting the sample with particles that adsorb the first peptide. The method may include contacting the sample with a known quantity of a labeled version of said first peptide. The method may include contacting the sample with a second particle that adsorbs said second peptide. The second particle may be different from the first particle. The method may include contacting the sample with a known quantity of a labeled version of said second peptide. The method may include separating peptides adsorbed to said first or said second particle from non-adsorbed peptides. The method may include eluting said peptides adsorbed to said first or second particles from said first or second particles. The method may include measuring the amount of said first peptide eluted from said first particle using a mass spectrometer. The method may include measuring the amount of said labeled version of said first peptide eluted from said first particle using a mass spectrometer. The method may include calculating the amount of the first peptide in the biological sample. The method may include measuring the amount of said second peptide eluted from said second particle using a mass spectrometer. The method may include measuring the amount of the labeled version of the second peptide eluted from said second particle using a mass spectrometer. The method may include calculating the amount of the second peptide in the biological sample. The biological sample may include a proteolytic digest of a bodily fluid sample.

A surprising aspect of some of the methods described herein is that each of the quality control (QC) standards introduced or used in the workflow may be multifunctional within the QC platform being deployed. For example, a full-length isotopically heavy-labeled QC protein added into a biological sample prior to any processing may fulfill at least 5+ QC metrics: (a) it may ensure proper protein digestion; (b) it may be used to assess liquid chromatography (LC) condition/operational state (e.g. proper gradient or mixing); (c) it may be used to assess LC plumbing (e.g. leaks or clogs); (d) it may be used to assess MS metrics (e.g. sensitivity or mass accuracy); (e) it may assist the instrument in reaching higher sensitivity; or (f) it may assist in final data normalization in the data analysis platform (e.g. post data acquisition). Another surprising aspect of some of the methods described herein is versatility of the QC pipeline for the application to multiple processing protocols. This method can be expanded and applied broadly for sample quality assurance from many different processing procedures.

Without the present disclosure, one may have difficulty achieving similar results to this disclosure. To do so, one may need to create a system to monitor measurement quality without internal standards (endogenous or exogenous) and make decisions; determine the unique internal standards for each protein detected by nano-particle enrichment, purchase or manufacturer the standards, determine the concentration of each internal standard to add into each sample; determine which proteoforms are typically part of the nano-particle corona formation so one would know which proteoforms (e.g. proteins with particular PTMs) to attempt collecting data on; determine which proteins are not part of a nanoparticle corona formation and develop alternative assays for these proteins; or create an algorithm, software, or database to control a mass spectrometer and collect additional biological information on each sample in either real time or through serial injections.

Disclosed herein, in some aspects, are methods comprising: contacting a biological sample of a subject with particles, thereby adsorbing endogenous biomolecules of the biological sample to the particles; and combining the biological sample or the adsorbed endogenous biomolecules with internal standards of the biomolecules. The internal standards may comprise a label. Some aspects include comprising measuring the endogenous biomolecules and the internal standards to obtain endogenous biomolecule measurements and internal standard measurements. Some aspects include identifying concentrations of the endogenous biomolecules based on the internal standard measurements.

b. Samples

Data sets may be generated from one or more samples. The samples may be of a subject. The sample may be a biological sample. Examples of biological sample include blood, serum, or plasma. Other examples of biological include urine, tears, semen, milk, vaginal fluid, mucus, saliva, or sweat. A biological may include a tissue or cell homogenate.

A biological sample may be obtained from a subject. For example, a blood, serum, or plasma sample may be obtained from a subject by a blood draw. Other ways of obtaining biological samples include aspiration or swabbing. Where multiple samples are used, the samples may be obtained from the subject at the same time, such as on the same day or during the same hour, or at separate times such as on separate days.

The biological sample may be cell-free or substantially cell-free. To obtain a cell-free or substantially cell-free biological sample, a biological sample may undergo a sample preparation method such as centrifugation and pellet removal.

A non-biofluid sample may be used or obtained. A non-biofluid sample may be obtained from a subject. For example, a sample may include a tissue sample. The sample may be identified by a physician as at a high risk or low risk of being cancerous. The sample may include a cell sample. The sample may include a homogenate of a cell or tissue. The sample may include a supernatant of a centrifuged homogenate of a cell or tissue.

The biological sample can be obtained from the subject during any phase of a screening procedure or during treatment of a subject. For example, the biological sample can be obtained before or during a stage where the subject is a candidate for a biopsy, for early detection of a disease. Or the biological sample may be obtained during a treatment protocol to assess the efficacy of treatment, or to monitor the subject.

Data may be generated from a single sample, or from multiple samples. Data from multiple samples may be obtained from the same subject. In some cases, different data types are obtained from samples collected differently or in separate containers. A sample may be collected in a container that includes one or more reagents such as a preservation reagent or a biomolecule isolation reagent. Some examples of reagents include heparin, ethylenediaminetetraacetic acid (EDTA), citrate, an anti-lysis agent, or a combination of reagents. Samples from a subject may be collected in multiple containers that include different reagents, such as for preserving or isolating separate types of biomolecules. A sample may be collected in a container that does not include any reagent in the container. The samples may be collected at the same time (e.g. same hour or day), or at different times. A sample may be frozen, refrigerated, heated, or kept at room temperature.

c. Data Generation

The methods described herein may include generating, obtaining, or using data sets. A data set may include omic data. Omic data may include information or data (such as measurements) on many or all of a certain type of biomolecule in a sample. For example, a data set may include measurements of proteins, transcripts, genetic material, metabolites, or lipids, and may include data on 500 or more, 750 or more, 1000 or more, 2500 or more, 5000 or more, 10,000 or more, 25,000 or more, biomolecules of a certain type. The data may relate to a presence, absence, or amount of a given biomolecule. A data set may include measurements.

The methods disclosed herein may include obtaining data such as a data set generated from one or more biological samples collected from a subject. The data may include biomolecule measurements such as protein measurements, transcript measurements, genetic material measurements, or metabolite measurements. A data set may include any of the following: proteomic data, genomic data, transcriptomic data, or metabolomic data. This section includes some ways of generating each of these types of data sets. Other types of data sets may also be generated. The data may be labeled or identified as indicative of a disease or as not indicative of a disease.

i. Use of Particles

Biological samples may be contacted with particles, for example prior to generating data. The data described herein may generated using particles. For example, a method may include contacting a sample with particles such that the particles adsorb biomolecules. The particles may attract different sets of biomolecules than would normally be difficult to measure accurately by performing omic measurements directly on the sample. For example a dominant biomolecule may make up a large percentage of certain type of biomolecules (e.g. proteins, transcripts, genetic material, lipids, or metabolites) in a sample. By adsorbing biomolecules to particles prior to analyzing them, a subset of biomolecules may be obtained that does not include the dominant biomolecule. Removing dominant biomolecules (e.g. biomolecules that make up a majority of a biological sample) in this way may increase the accuracy of biomolecule measurements and sensitivity of an analysis using those measurements.

The particles may useful in a method that include contacting a biological sample with particles, thereby adsorbing endogenous biomolecules of the biological sample to the particles; and combining the biological sample or the adsorbed endogenous biomolecules with reference biomolecules (e.g. internal standards) of the biomolecules.

Examples of biomolecules that may be adsorbed to particles include proteins, transcripts, genetic material, or metabolites. The adsorbed biomolecules may make up a biomolecule corona around the particle. The adsorbed metabolites may be measured or identified in generating a data set.

Particles can be made from various materials. Such materials may include metals, magnetic particles, polymers, or lipids. A particle may be made from a combination of materials. A particle may comprise layers of different materials. The different materials may have different properties. A particle may include a core comprising one material, and be coated with another material. The core and the coating may have different properties.

A particle may include a metal. For example, a particle may include gold, silver, copper, nickel, cobalt, palladium, platinum, iridium, osmium, rhodium, ruthenium, rhenium, vanadium, chromium, manganese, niobium, molybdenum, tungsten, tantalum, iron, or cadmium, or a combination thereof.

A particle may be magnetic (e.g., ferromagnetic or ferrimagnetic). A particle comprising iron oxide may be magnetic. A particle may include a superparamagnetic iron oxide nanoparticle (SPION).

A particle may include a polymer. Examples of polymers include polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, or polyamines, a polyalkylene glycol (e.g., polyethylene glycol (PEG)), a polyester (e.g., poly(lactide-co-glycolide) (PLGA), polylactic acid, or polycaprolactone), or a copolymer of two or more polymers, such as a copolymer of a polyalkylene glycol (e.g., PEG) and a polyester (e.g., PLGA). A particle may be made from a combination of polymers.

A particle may include a lipid. Examples of lipids include dioleoylphosphatidylglycerol (DOPG), diacylphosphatidylcholine, diacylphosphatidylethanolamine, ceramide, sphingomyelin, cephalin, cholesterol, cerebrosides and diacylglycerols, dioleoylphosphatidylcholine (DOPC), dimyristoylphosphatidylcholine (DMPC), and dioleoylphosphatidylserine (DOPS), phosphatidylglycerol, cardiolipin, diacylphosphatidylserine, diacylphosphatidic acid, N-dodecanoyl phosphatidylethanolamines, N-succinyl phosphatidylethanolamines, N-glutarylphosphatidylethanolamines, lysylphosphatidylglycerols, palmitoyloleyolphosphatidylglycerol (POPG), lecithin, lysolecithin, phosphatidylethanolamine, lysophosphatidylethanolamine, dioleoylphosphatidylethanolamine (DOPE), dipalmitoyl phosphatidyl ethanolamine (DPPE), dimyristoylphosphoethanolamine (DMPE), distearoyl-phosphatidyl-ethanolamine (DSPE), palmitoyloleoyl-phosphatidylethanolamine (POPE) palmitoyloleoylphosphatidylcholine (POPC), egg phosphatidylcholine (EPC), di stearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), palmitoyloleyolphosphatidylglycerol (POPG), 16-O-monomethyl PE, 16-O-dimethyl PE, 18-1-trans PE, palmitoyloleoyl-phosphatidylethanolamine (POPE), 1-stearoyl-2-oleoyl-phosphatidyethanolamine (SOPE), phosphatidylserine, phosphatidylinositol, sphingomyelin, cephalin, cardiolipin, phosphatidic acid, cerebrosides, dicetylphosphate, or cholesterol. A particle may be made from a combination of lipids.

Further examples of materials include silica, carbon, carboxylate, polyacrylic acid, carbohydrates, dextran, polystyrene, dimethylamine, amines, or silanes. Some examples of particles include a carboxylate SPION, a phenol-formaldehyde coated SPION, a silica-coated SPION, a polystyrene coated SPION, a carboxylated Poly(styrene-co-methacrylic acid), P(St-co-MAA) coated SPION, a N-(3-Trimethoxysilylpropyl)diethylenetriamine coated SPION, a poly(N-(3-(dimethylamino)propyl) methacrylamide) (PDMAPMA)-coated SPION, a 1,2,4,5-Benzenetetracarboxylic acid coated SPION, a poly(vinylbenzyltrimethylammonium chloride) (PVBTMAC) coated SPION, caboxylate coated with peracetic acid, a poly(oligo(ethylene glycol) methyl ether methacrylate) (POEGMA)-coated SPION, a polystyrene carboxyl functionalized particle, a carboxylic acid particle, a particle with an amino surface, a silica amino functionalized particle, a particle with a Jeffamine surface, or a silica silanol coated particle.

Some examples of nanoparticles include the following: P-033 (carboxylate microparticle, surfactant free), P-039 (polystyrene carboxyl functionalized), P-047 (silica), P-053 (amino surface microparticle, 0.4-0.6 μm), P-065 (silica), P-073 (dextran based coating, 0.13 μm), S-003 (silica-coated (SPION), S-006 (N-(3-trimethoxysilylpropyl)diethylenetriamine coated SPION), S-007 (poly(N-(3-(dimethylamino) propyl) methacrylamide) (PDMAPMA)-coated SPION), or S-010 (carboxylate, polyacrylic acid coated SPION).

Particles of various sizes may be used. The particles may include nanoparticles. Nanoparticles may be from about 10 nm to about 1000 nm in diameter. For example, the nanoparticles can be at least 10 nm, at least 100 nm, at least 200 nm, at least 300 nm, at least 400 nm, at least 500 nm, at least 600 nm, at least 700 nm, at least 800 nm, at least 900 nm, from 10 nm to 50 nm, from 50 nm to 100 nm, from 100 nm to 150 nm, from 150 nm to 200 nm, from 200 nm to 250 nm, from 250 nm to 300 nm, from 300 nm to 350 nm, from 350 nm to 400 nm, from 400 nm to 450 nm, from 450 nm to 500 nm, from 500 nm to 550 nm, from 550 nm to 600 nm, from 600 nm to 650 nm, from 650 nm to 700 nm, from 700 nm to 750 nm, from 750 nm to 800 nm, from 800 nm to 850 nm, from 850 nm to 900 nm, from 100 nm to 300 nm, from 150 nm to 350 nm, from 200 nm to 400 nm, from 250 nm to 450 nm, from 300 nm to 500 nm, from 350 nm to 550 nm, from 400 nm to 600 nm, from 450 nm to 650 nm, from 500 nm to 700 nm, from 550 nm to 750 nm, from 600 nm to 800 nm, from 650 nm to 850 nm, from 700 nm to 900 nm, or from 10 nm to 900 nm in diameter. A nanoparticle may be less than 1000 nm in diameter. Some examples include diameters of about 50 nm, about 130 nm, about 150 nm, 400-600 nm, or 100-390 nm.

The particles may include microparticles. A microparticle may be a particle that is from about 1 μm to about 1000 μm in diameter. For example, the microparticles can be at least 1 μm, at least 10 μm, at least 100 μm, at least 200 μm, at least 300 μm, at least 400 μm, at least 500 μm, at least 600 μm, at least 700 μm, at least 800 μm, at least 900 μm, from 10 μm to 50 μm, from 50 μm to 100 μm, from 100 μm to 150 μm, from 150 μm to 200 μm, from 200 μm to 250 μm, from 250 μm to 300 μm, from 300 μm to 350 μm, from 350 μm to 400 μm, from 400 μm to 450 μm, from 450 μm to 500 μm, from 500 μm to 550 μm, from 550 μm to 600 μm, from 600 μm to 650 μm, from 650 μm to 700 μm, from 700 μm to 750 μm, from 750 μm to 800 μm, from 800 μm to 850 μm, from 850 μm to 900 μm, from 100 μm to 300 μm, from 150 μm to 350 μm, from 200 μm to 400 μm, from 250 μm to 450 μm, from 300 μm to 500 μm, from 350 μm to 550 μm, from 400 μm to 600 μm, from 450 μm to 650 μm, from 500 μm to 700 μm, from 550 μm to 750 μm, from 600 μm to 800 μm, from 650 μm to 850 μm, from 700 μm to 900 μm, or from 10 μm to 900 μm in diameter. A microparticle may be less than 1000 μm in diameter. Some examples include diameters of 2.0-2.9 μm.

The particles may include physiochemically distinct sets of particles (for example, 2 or more sets of physiochemically particles where 1 set of particles is physiochemically distinct from another set of particles. Examples of physiochemical properties include charge (e.g., positive, negative, or neutral) or hydrophobicity (e.g. hydrophobic or hydrophilic). The particles may include 2, 3, 4, 5, 6, 7, 8, 9, 10, 11, 12, 13, 14, 15, 16, 17, 18, 19, 20, or more sets of particles, or a range of sets of particles including any of said numbers of sets of particles.

A sample may be contacted with particles and internal standard biomolecules. The combination of nanoparticles with internal standards may include a combination of the internal standards and sample with one nanoparticle at a time, or with multiple nanoparticles in the same sample.

ii. Use of Reference Biomolecules

In some aspects, obtaining proteomic data can include the use of a reference biomolecule, which may be labeled. The reference biomolecule may comprise an internal standard. For example, the reference biomolecule may be added at a predetermined amount to the biological sample to serve as an internal standard, and to aid in identification of similar biomolecules that are endogenous to the sample. For example, isotopically labeled reference proteins may be spiked into a sample, measured along with endogenous proteins using mass spectrometry, used to identify the endogenous proteins on mass spectra, and also used to help determine an accurate amount of the endogenous proteins. An internal standard may include a biomolecule that is added in a constant or known amount to the biological sample. Internal standards may comprise a non-endogenous labeled version of the endogenous biomolecules.

The reference biomolecules may useful in a method that include contacting a biological sample with particles, thereby adsorbing endogenous biomolecules of the biological sample to the particles; and combining the biological sample or the adsorbed endogenous biomolecules with reference biomolecules (e.g. internal standards) of the biomolecules.

The reference biomolecules may include an isotopic label, a mass tag, a barcode, a post-translation modification (PTM), or a biomolecule from a species different than a species of the subject. The reference biomolecules may include a label. The label may be isotopic. The reference biomolecules may include a mass tag. The reference biomolecules may include a barcode. The reference biomolecules may include a PTM. The reference biomolecules may include a biomolecule from a species different than a species of the subject. The reference biomolecules may include multiple labels such as isotopic labels, mass tags, barcodes, PTMs, or biomolecules from a species different than a species of the subject.

Of the labeled and endogenous biomolecules, individual labeled biomolecules may correspond to the individual endogenous biomolecules. For example, the biomolecules may comprise proteins, and the endogenous proteins may comprise 100-1500 different proteins and the labeled biomolecules may comprise the same 100-1500 proteins but each labeled biomolecule may comprise a label.

The reference biomolecules may include at least 5, at least 10, at least 50, at least 100, at least 250, at least 500, at least 750, at least 1000, at least 1500, at least 2000, at least 2500, at least 5000, at least 7500, at least 10,000, at least 15,000, at least 20,000, or at least 25,000 individual or distinct biomolecules. In some instances, the reference biomolecules include less than 5, less than 10, less than 50, less than 100, less than 250, less than 500, less than 750, less than 1000, less than 1500, less than 2000, less than 2500, less than 5000, less than 7500, less than 10,000, less than 15,000, less than 20,000, or less than 25,000 individual or distinct biomolecules.

As an example, a sample comprises endogenous protein A, endogenous protein B, and endogenous protein C. Endogenous proteins A, B and C are difficult to measure because of their low abundance. Upon spiking predetermined amounts of isotopically labeled versions of proteins A, B and C into the sample, endogenous proteins A, B, and C, and the isotopically labeled versions of proteins A, B and C are analyzed together using mass spectrometry. Because the isotopically labeled versions are heavier, their mass spectra are shifted, and are distinguishable from mass spectra for the endogenous proteins. The isotopically labeled versions are more readily identifiable on a mass spectrometry readout thereby facilitating the identification of mass spectra for endogenous proteins A, B and C on the mass spectrometry readout. Because a predetermined amount of isotopically labeled proteins A, B, and C was added to spiked into the sample, their concentration is known, and the mass spectra for isotopically labeled proteins A, B, and C are used to accurately measure the amounts of endogenous proteins A, B, and C from the mass spectrometry readout. The accurate measurements of the endogenous proteins A, B, and C may be obtained by comparing the relative intensities of the mass spectrometry readouts for endogenous proteins A, B, and C relative to the intensities of the mass spectrometry readouts for the known concentrations or amounts of isotopically labeled proteins A, B, and C.

The reference biomolecule may include a reference protein, reference transcript, reference nucleic acid, reference metabolite, or reference lipid. The reference biomolecule may be labeled. The label may include isotopic labeling or fluorescent labeling. The reference biomolecule can be labeled (e.g., with a tag) or unlabeled but with known property. For example, the reference biomolecule can be a plurality of polypeptides with known molar ratio and mass, which can yield reference measurements (e.g., functioning as internal standards in mass spectrometry measurements).

The reference biomolecule may be added to the biological sample for generating the measurements described herein. The method may include combining the first or second sample with the reference biomolecules, measuring the reference biomolecules with the biomolecules, and using the reference biomolecules to obtain the second measurements. The reference biomolecule may be detected by mass spectrometry or another method for measuring biomolecules described herein. In some aspects, the reference biomolecule is added to the biological sample before or after the biological sample is contacted with a particle or particles.

To further aid in identifying and measuring the endogenous biomolecules, and affinity reagent such as an antibody may be used to enrich (e.g. immunoprecipitate) the endogenous biomolecules. The enrichment may be performed before spiking the sample with the reference biomolecule, and may include adhering biomolecules to the affinity reagent, centrifuging or concentrating the affinity reagents adhered to the biomolecules, removing or separating excess sample or other biomolecules not to be measured from the affinity reagents adhered to the biomolecules, and eluting the biomolecules from the affinity reagents. Use of affinity reagents in this way may be used to enrich for specific types of biomolecules or pathways. For example, proteins with a particular post-translational modification (PTM), or proteins of a particular molecular pathway may be enriched through the use of one or more affinity reagents specific for that post-translational modification or molecular pathway.

A method may include obtaining a first data set comprising first measurements of biomolecules adsorbed to particles from a first biological sample of a subject; and obtaining a second data set comprising second measurements of the biomolecules of the first biological sample or of a second biological sample of the subject. The second measurements may include measurements of endogenous biomolecules normalized or adjusted based on measurements of labeled reference biomolecules combined with the first biological sample or combined with the second biological sample. The labeled reference biomolecules are the same as the endogenous biomolecules but each comprise a label. A method may include applying a first classifier to assign a first label corresponding to a biological state to the first data set; applying a second classifier to assign a second label corresponding to the biological state to the second data set; and combining the first label and the second label to obtain a combined label corresponding to the biological state.

A method may include obtaining measurements of endogenous biomolecules adsorbed to particles (e.g. nanoparticles) from a biological sample of a subject, and obtaining measurements of labeled reference biomolecules combined with the biological sample, or combined with the endogenous biomolecules adsorbed to the particles. The labeled reference biomolecules may be the same as the endogenous biomolecules but also comprise a label. A method may include normalizing or adjusting the measurements of the endogenous biomolecules based on the measurements of the labeled reference biomolecules. A method may include applying a classifier to the normalized or adjusted measurements to assign a label corresponding to a biological state to the normalized or adjusted measurements.

A method may include contacting a biological sample of a subject with particles, thereby adsorbing endogenous biomolecules of the biological sample to the particles. A method may include combining the biological sample or the adsorbed endogenous biomolecules with internal standards of the biomolecules (which may comprise a label). A method may include combining the biological sample with internal standards of the biomolecules (which may comprise a label). A method may include combining the adsorbed endogenous biomolecules with internal standards of the biomolecules comprising a label. A method may include measuring the endogenous biomolecules and the internal standards to obtain endogenous biomolecule measurements and internal standard measurements.

Some aspects include determining a quality control aspect of the endogenous biomolecule measurements based on measurements of the internal standard measurements. In some aspects, the biological sample comprises a group of biological samples, measuring the endogenous biomolecules comprises measuring the endogenous biomolecules of the group of biological samples, and the quality control aspect is in relation to the endogenous biomolecules of the group of biological samples. In some aspects, the quality control aspect comprises a mass accuracy, quantitative precision, quantitative accuracy, correlation with a standard sample, chromatographic performance, corona formation quality, digestion quality, or a contaminant biomolecule measurement. The quality control aspect may include mass accuracy. The quality control aspect may include quantitative precision. The quality control aspect may include quantitative accuracy. The quality control aspect may include correlation with a standard sample. The quality control aspect may include chromatographic performance. The quality control aspect may include corona formation quality. The quality control aspect may include digestion quality. The quality control aspect may include a contaminant biomolecule measurement.

In some aspects, the measurements are obtained by a mass spectrometer. Some aspects include performing real-time control of the mass spectrometer based on the internal standard measurements, or based on the quality control aspect. In some aspects, performing real-time control of the mass spectrometer comprises adjusting internal voltages to provide a change in specificity, adjusting a sample volume, adjusting a technical condition to improve measurement quality, pausing or stopping data collection, rescheduling a measurement, or notifying a user of a quality control issue. Performing real-time control of the mass spectrometer may include adjusting an internal voltage. The internal voltage adjustment may provide a change in specificity. Performing real-time control of the mass spectrometer may include adjusting a sample volume. Performing real-time control of the mass spectrometer may include adjusting a technical condition. Adjusting the technical condition may improve measurement quality. Performing real-time control of the mass spectrometer may include pausing data collection. Performing real-time control of the mass spectrometer may include stopping data collection. Performing real-time control of the mass spectrometer may include scheduling a measurement. Performing real-time control of the mass spectrometer may include rescheduling a measurement. Performing real-time control of the mass spectrometer may include notifying a user of a quality control issue.

Some aspects include normalizing or adjusting the endogenous biomolecule measurements based on the internal standard measurements. Some aspects include normalizing an endogenous biomolecule measurement based on an internal standard measurement. Some aspects include adjusting an endogenous biomolecule measurement based on an internal standard measurement. In some aspects, the endogenous biomolecule measurements comprise an amount of the endogenous biomolecules in the biological sample. Some aspects include determining an amount of the endogenous biomolecules adsorbed to the particles relative to the amount of the endogenous biomolecules in the biological sample. Some aspects include identifying a source of variability in the endogenous biomolecule measurements based on the internal standard measurements. Some aspects include using the internal standard measurements to identify or obtain additional endogenous biomolecule measurements.

In some cases, the reference biomolecule is useful in recovering a false negative measurement. For example, an endogenous biomolecule such as a peptide may be present in a sample that is contacted with a particle such as a nanoparticle, and in some instances the endogenous biomolecule is measured or identified through the use of the reference biomolecule. For example, a mass spectrum of the endogenous biomolecule may be identified upon identification of and comparison to a mass spectrum of the reference biomolecule. The endogenous biomolecule may then be measured. In some instances, an endogenous biomolecule would not have been measured or identified without use of the reference biomolecule.

In some cases, the reference biomolecule is useful in confirming a true negative measurement. may help recover false negative. For example, an endogenous biomolecule such as a peptide may not be present in a sample that is contacted with a particle such as a nanoparticle, and in some instances the endogenous biomolecule is falsely measured or identified through the use of the reference biomolecule. For example, a peak on a mass spectrum not associated with an endogenous biomolecule may be identified as associated with the endogenous biomolecule, and this may be corrected through comparison to a mass spectrum of the reference biomolecule. The false measurement of the endogenous biomolecule may then be omitted from the data set or measurements. In some instances, an endogenous biomolecule would have been measured or identified falsely or inaccurately without use of the reference biomolecule.

In some cases, the reference biomolecule is useful in recovering or confirming a false positive measurement or a true positive measurement.

Figure 5A:
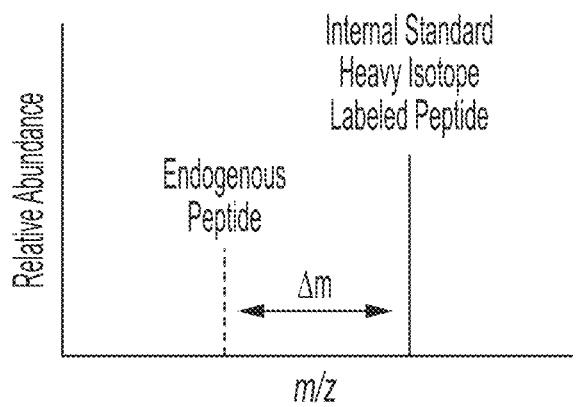
FIG. 5A illustrates an example of mass spectrometry measurements of an endogenous biomolecule and a labeled version of the biomolecule.

FIG. 5A-5D illustrate scenarios of internal standard signal enhancement. FIG. 5A illustrates an example of use of an internal heavy standard biomolecule. FIG. 5A includes two mass spectrometry peaks of peptides having the same sequence, but having different m/z ratios due to introduction of a heavy isotope in the internal standard.

Figure 5B:
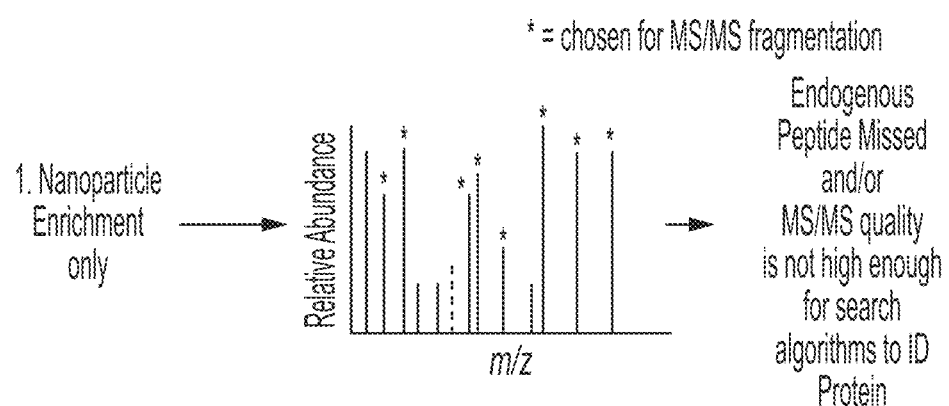
FIG. 5B illustrates an example of mass spectrometry data which may be unable to identify certain biomolecules without the use of a reference biomolecule.

FIG. 5B illustrates mass spectrometry measurements made with nanoparticle enrichment only. Certain endogenous protein identifications may be missed in acquisition or discarded from search results due to low abundance or low-quality MS/MS spectra.

Figure 5C:
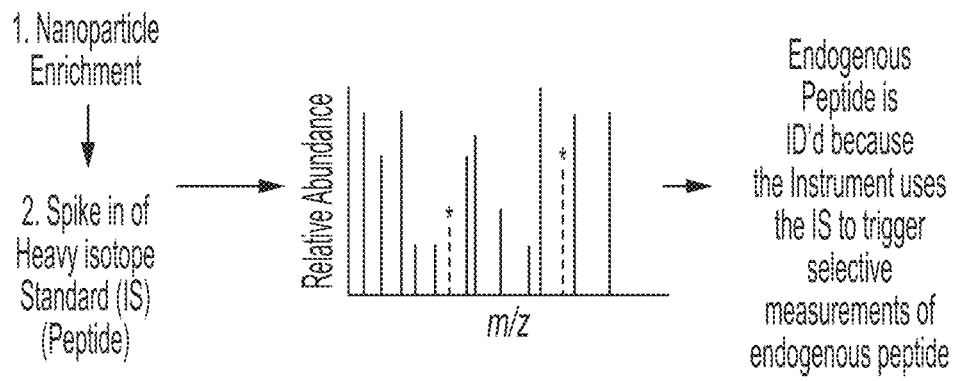
FIG. 5C illustrates an example of mass spectrometry data obtained upon: combining reference biomolecules with endogenous biomolecules, after the endogenous biomolecules are adsorbed to particles.

FIG. 5C illustrates an example in which internal standards were spiked into a sample containing nanoparticle-enriched biomolecules. In the example in FIG. 5C, signal from low abundance protein species enriched with nanoparticles selectively fragment with the assistance of heavy-labeled internal standards. This method allows high quality (e.g. accurate and precise) quantification of these low abundant proteins that were present in nanoparticle enriched samples, but which were previously missed in measurements with no internal standard. This process also allows monitoring and quality control (QC) of the LC and MS operational performance and data analysis procedures.

Figure 5D:
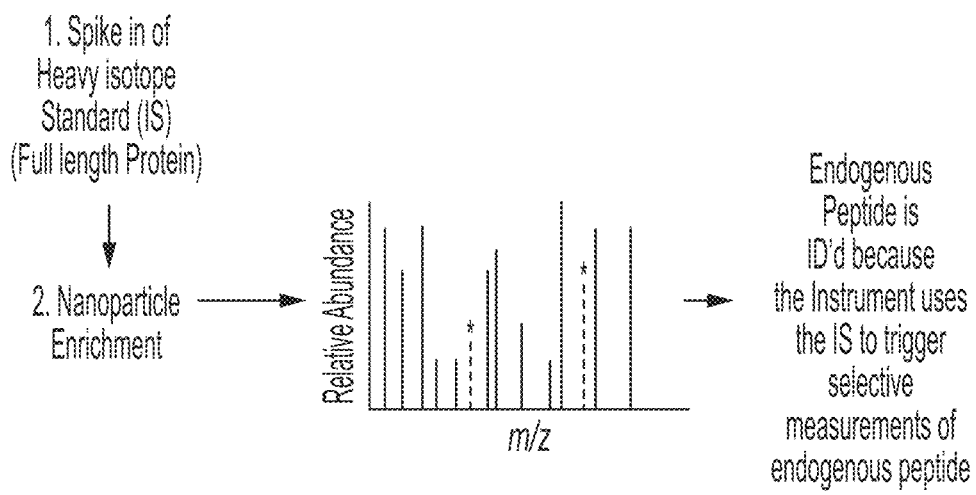
FIG. 5D illustrates an example of mass spectrometry data obtained upon: combining reference biomolecules with endogenous biomolecules before the endogenous biomolecules and reference biomolecules are adsorbed to particles.

Another scenario is shown in FIG. 5D, which illustrates signal from low abundance protein species enriched with nanoparticles, selectively fragmented with the assistance of heavy-labeled internal standards (e.g. full length proteins). The full length heavy-labeled proteins may be enriched by nanoparticles along with their low abundant endogenous non-labeled proteins. The proteins (internal standard or IS and endogenous) may be digested and analyzed by LC-MS/MS. The heavy labeled internal standard may assist the instrument to enhance the signal of the endogenous protein. This enables high quality (e.g. accurate and precise) quantification of these low abundant proteins that are present in some nanoparticle enriched samples but previously missed in measurements with no internal standard. This process also allowed monitoring and quality control (QC) of the digestion efficiency, nanoparticle enrichment efficiency, LC and MS operational performance and data analysis procedures.

The reference biomolecules may be or include a set of peptide or protein internal standards. The peptide or protein internal standards may include isotopically labeled proteins, isotopically labeled peptides, proteins with an additional tag (e.g. mass or barcode), peptides with an additional tag (e.g. post-translational modification [PTM], chemical, or barcode), or peptides or proteins from a non-human species.

The peptide or protein internal standards may be used in establishing concentrations of individual endogenous peptides and proteins. The internal standards may be added at a predetermined and known concentration to all, or a sub-set of, samples processed utilizing nanoparticles, and may be used to calculate the concentration of each endogenous protein through any of a variety of methods.

The peptide or protein internal standards may be used in establishing a measurement quality of a sample. All, or a sub-set of, the internal standards added to a sample prior or after processing the sample by nanoparticles may be used to determine a variety of quality control metrics. Examples of such quality control metrics, or of indices of measurement quality, include: mass accuracy, quantitative precision, quantitative accuracy, correlation with known standard samples or standards (e.g. Pearson correlation or Demming regression), chromatographic performance (e.g. retention time, peak width, FWHM, peak asymmetry, or peak capacity), coronal formation quality, digestion quality (e.g. missed cleavages or oxidation rate), or measurement or control of contaminants such as contaminant proteins that are routinely encountered in proteomic sample preparation workflows. The peptide or protein internal standards may similarly be used in establishing the measurement quality of a group of samples (e.g. a batch of samples).

The peptide or protein internal standards may be used in real-time control of a mass spectrometer based on measurement quality assessed as described herein to perform an adjustment, pause or stop data collection, rescheduling of sample or data collection, or provide automated notifications. For example, the peptide or protein internal standards may be used in real-time to adjust of internal voltages to provide a change in sensitivity (e.g. detector gain). The peptide or protein internal standards may be used in real-time to adjust a sample volume used for analysis of individual subjects. The peptide or protein internal standards may be used in real-time to adjust technical conditions to provide superior data quality. An example is real time evaluation of MS/MS spectra to determine if additional or reduced fragmentation energy is needed to create a MS/MS spectra above a defined threshold. The peptide or protein internal standards may be used in real-time to pause or stop data collection if instrument performance is below one, or several, defined performance thresholds. The peptide or protein internal standards may be used in real-time to reschedule individual samples or control samples to collect additional data either after instrument adjustments (e.g. voltages) or instrument maintenance (e.g. cleaning). Additional data collection may include additional quantitative data, biological data (e.g. collection of additional biologically relevant data based on detection of expected or unexpected biological changes via data driven control of a mass spectrometer), or technical data (e.g. adjustment of fragmentation energy). The peptide or protein internal standards may be used in real-time to automate a notification message sent directly to a user as a warning that a quality control (QC) performance threshold limit is approached or surpassed.

Real-time control of a mass spectrometer may include real-time control of mass spectrometry measurements. While being measured by the mass spectrometer, biomolecules in a sample may be mixed with internal control biomolecules, and may have been adsorbed or contacted with particles. The biomolecules measured using a mass spectrometer may include biomolecules adsorbed in a sample to a single type of particle, or may include biomolecules adsorbed in a sample to multiple types of particles. The adsorption of biomolecules to multiple types of particles may include contact of the sample with multiple types of particles together, or may include contact of aliquots of the sample separately with one or more particle types per aliquot and then the aliquots may be pooled for measuring the adsorbed biomolecules. The biomolecules in the sample may have contacted with particles and internal standard biomolecules. The combination of nanoparticles with internal standards may include a combination of the internal standards and sample with one nanoparticle at a time, or with multiple nanoparticles in the same sample. Some aspects may include multiple injections/sample/particle, and different decisions may be made in real-time during the measurement of each separate injection. Such an analysis may be repeated and a decision process may be made across all nanoparticles. In some aspects, multiple particles are pooled together, and then a mass spectrometry analysis is performed.

The peptide or protein internal standards may be used in normalization of 2 or more samples through the use of either measured quantitative values of the internal standards. Internal standards may be added to each sample either prior to after the processing by nanoparticles. Internal standards may be added to control samples (technical or biological) to provide known reference values. A variety of techniques (e.g. median or local regression such as LOESS) can be used to normalize differences in response as a function of processing by nanoparticles and/or measurement by mass spectrometry.

The peptide or protein internal standards may be used in establishing or determining the recovery of each protein processed utilizing nanoparticles. Determining the recovery of each protein may be useful for providing understanding of protein losses on a nanoparticle as a function of corona formation or PPI and available individual protein concentration after processing by nanoparticles. This information can be used to derive a far more accurate quantitation of endogenous biomolecules such as endogenous biomolecules adsorbed to nanoparticles.

The peptide or protein internal standards may be used in establishing or determining biological concentrations of proteins, and proteoforms, in individual patient samples. Internal standards added prior to processing of samples by nanoparticles may be useful for providing a measurement of the sample concentration of endogenous proteins or protoeforms.

The peptide or protein internal standards may be used in establishing or identifying sources of variability of processing samples by nanoparticles and mass spectrometry. Addition of internal standards after processing samples may provide a measurement of the technical variability associated with the measurement. Addition of internal standards prior to processing of samples may provide a direct measurement of technical variability for an entire sample processing process.

The peptide or protein internal standards may be used in collection of additional biologically relevant data (e.g. proteoforms) based the detection of expected or unexpected biological changes via data driven control of a mass spectrometer. Dependent on the data collected and analyzed in real time (e.g. MS/MS, Database search results, quantitation, or CCS value) a mass spectrometer may be controlled to generate additional data. When a protein is detected, or detected above a desired threshold, then the mass spectrometer can be directed to collect additional MS/MS data on predicted PTM or genetically modified version of the same peptide/protein.

Detection of discordant peptides may trigger additional data generation. The concentration of several unique peptides for a given protein may be either up or down regulated in the same direction relative to a reference concentration (e.g. a control sample concentration). When a discordant peptide is detected, then the instrument can be controlled in real time to collect data on the genetically modified version of the peptide (e.g. pre-calculated in a database). A discordant peptide may be due to either genetic modification (e.g. a mutation or single nucleotide polymorphism [SNP]) or a post-translational modification (PTM; e.g. glycosylation or phosphorylation). The additional data collected may be based on a database of predicted mass, retention times, CCS, Kendrick mass defect or predicted energy required to sequence the desired peptide (e.g. fragmentation modality and energy). The mode and energy of fragmentation may be determined based on the predicted modification one is attempting to detect (e.g. EAD/ETD for glycosylated proteins vs CID for SNP modified peptides).

Data driven detection of individual genetic fingerprints may be based on a confirmed detection of unique peptides/proteins with and without genetic modification utilizing internal standards in an individual sample. For a confirmed protein detection, the mass spectrometer may be controlled to collect data from predicted genetically modified peptide sequences from an individual, or panel of, peptide(s)/protein (s) detected with internal standards. Data driven detection of individual genetic fingerprints may be based on a known or determined phenotypic status.

Data driven detection of an individual's response to a given therapy may be determined. Detection may be confirmed or performed with internal standards and nanoparticles of a unique set of peptides/proteins associated with response/non-response to a particular treatment for either a known, or determined, health status (e.g. NSCLC).

The peptide or protein internal standards may be used in determination of one or multiple health status(s) through the quantitative peptide and protein measurements, comparison to known pattern of peptide and protein concentrations, and assessment.

The peptide or protein internal standards may be used in health status call based on the concentrations of multiple peptides/proteins in a single sample (e.g. CRC based on detected concentration of certain proteins (modified or unmodified). A database of signatures/classifiers may be used.

iii. Proteomic Data

A data set may include proteomic data or protein data (such as protein measurements). Proteomic data may involve data about proteins, peptides, or proteoforms. This data may include measurements of just peptides or proteins, or a combination of both. An example of a peptide is an amino acid chain. An example of a protein is a peptide or a combination of peptides. For example, a protein may include one, two or more peptides bound together. A protein may also include any post-translational modifications (PTMs). Proteomic data may include data about various proteoforms. Proteoforms can include different forms of a protein produced from a genome with any variety of sequence variations, splice isoforms, or post-translational modifications. The proteomic data may be generated using an unbiased, non-targeted approach, or may include a specific set of proteins.

Proteomic data may include information on the presence, absence, or amount of various proteins, peptides. For example, proteomic data may include amounts of proteins. A protein amount may be indicated as a concentration or quantity of proteins, for example a concentration of a protein in a biological sample. A protein amount may be relative to another protein or to another biomolecule. Proteomic data may include information on the presence of proteins or peptides. Proteomic data may include information on the absence of proteins or peptides. Proteomic data may be distinguished by type, where each type includes a different type of protein, peptide, or proteoform.

Proteomic data generally includes data on a number of proteins or peptides. For example, proteomic data may include information on the presence, absence, or amount of 1000 or more proteins or peptides. In some cases, proteomic data may include information on the presence, absence, or amount of 5000, 10,000, 20,000, or more peptides, proteins, or proteoforms. Proteomic data may even include up to about 1 million proteoforms. Proteomic data may include a range of proteins, peptides, or proteoforms defined by any of the aforementioned numbers of proteins, peptides, or proteoforms.

Proteomic data may be generated by any of a variety of methods. Generating proteomic data may include using a detection reagent that binds to a peptide or protein and yields a detectable signal. After use of a detection reagent that binds to a peptide or protein and yields a detectable signal, a readout may be obtained that is indicative of the presence, absence or amount of the protein or peptide. Generating proteomic data may include concentrating, filtering, or centrifuging a sample.

Proteomic data may be generated using mass spectrometry, chromatography, liquid chromatography, high-performance liquid chromatography, solid-phase chromatography, a lateral flow assay, an immunoassay, an enzyme-linked immunosorbent assay, a western blot, a dot blot, or immunostaining, or a combination thereof. Some examples of methods for generating proteomic data include using mass spectrometry, a protein chip, or a reverse-phased protein microarray. Proteomic data may also be generated using a immunoassays such as enzyme-linked immunosorbent assays, western blots, dot blots, or immunohistochemistry. Generating proteomic data may involve use of an immunoassay panel.

One way of obtaining proteomic data includes use of mass spectrometry. An example of a mass spectrometry method includes use of high resolution, two-dimensional electrophoresis to separate proteins from different samples in parallel, followed by selection or staining of differentially expressed proteins to be identified by mass spectrometry. Another method uses stable isotope tags to differentially label proteins from two different complex mixtures. The proteins within a complex mixture may be labeled isotopically and then digested to yield labeled peptides. Then the labeled mixtures may be combined, and the peptides may be separated by multidimensional liquid chromatography and analyzed by tandem mass spectrometry. A mass spectrometry method may include use of liquid chromatography—mass spectrometry (LC-MS), a technique that may combine physical separation capabilities of liquid chromatography (e.g., HPLC) with mass spectrometry.

In addition to any of the above methods, generating proteomic data may include contacting a sample with particles such that the particles adsorb biomolecules comprising proteins. The adsorbed proteins may be part of a biomolecule corona. The adsorbed proteins may be measured or identified in generating the proteomic data.

iv. Transcriptomic Data

A data set may include transcriptomic data or transcript data (such as transcript measurements). Transcriptomic data may involve data about nucleotide transcripts such as RNA. Examples of RNA include messenger RNA (mRNA), ribosomal RNA (rRNA), signal recognition particle (SRP) RNA, transfer RNA (tRNA), small nuclear RNA (snRNA), small nucleoar RNA (snoRNA), long noncoding RNA (lncRNA), microRNA (miRNA), noncoding RNA (ncRNA), or piwi-interacting RNA (piRNA), or a combination thereof. The RNA may include mRNA. The RNA may include miRNA. Transcriptomic data may be distinguished by type, where each type includes a different type of RNA or transcript. For example, mRNA data may be included in one type, and data for one or more types of small non-coding RNAs such as miRNAs or piRNAs may be included in another type. A miRNA may include a 5p miRNA or a 3p miRNA.

Transcriptomic data may include information on the presence, absence, or amount of various RNAs. For example, transcriptomic data may include amounts of RNAs. An RNA amount may be indicated as a concentration or number or RNA molecules, for example a concentration of an RNA in a biological sample. An RNA amount may be relative to another RNA or to another biomolecule. Transcriptomic data may include information on the presence of RNAs. Transcriptomic data may include information on the absence of RNA.

Transcriptomic data generally includes data on a number of RNAs. For example, transcriptomic data may include information on the presence, absence, or amount of 1000 or more RNAs. In some cases, transcriptomic data may include information on the presence, absence, or amount of 5000, 10,000, 20,000, or more RNAs. Transcriptomic data may even include up to about 200,000 transcripts. Transcriptomic data may include a range of transcripts defined by any of the aforementioned numbers of RNAs or transcripts.

Transcriptomic data may be generated by any of a variety of methods. Generating transcriptomic data may include using a detection reagent that binds to an RNA and yields a detectable signal. After use of a detection reagent that binds to an RNA and yields a detectable signal, a readout may be obtained that is indicative of the presence, absence or amount of the RNA. Generating transcriptomic data may include concentrating, filtering, or centrifuging a sample.

Transcriptomic data may include RNA sequence data. Some examples of methods for generating RNA sequence data include use of sequencing, microarray analysis, hybridization, polymerase chain reaction (PCR), or electrophoresis, or a combination thereof. A microarray may be used for generating transcriptomic data. PCR may be used for generating transcriptomic data. PCR may include quantitative PCR (qPCR). Such methods may include use of a detectable probe (e.g. a fluorescent probe) that intercalates with double-stranded nucleotides, or that binds to a target nucleotide sequence. PCR may include reverse transcriptase quantitative PCR (RT-qPCR). Generating transcriptomic data may involve use of a PCR panel.

RNA sequence data may be generated by sequencing a subject's RNA or by converting the subject's RNA into DNA (e.g. complementary DNA (cDNA)) first and sequencing the DNA. Sequencing may include massive parallel sequencing. Examples of massive parallel sequencing techniques include pyrosequencing, sequencing by reversible terminator chemistry, sequencing-by-ligation mediated by ligase enzymes, or phospholinked fluorescent nucleotides or real-time sequencing. Generating transcriptomic data may include preparing a sample or template for sequencing. A reverse transcriptase may be used to convert RNA into cDNA. Some template preparation methods include use of amplified templates originating from single RNA or cDNA molecules, or single RNA or cDNA molecule templates. Examples of amplification methods include emulsion PCR, rolling circle, or solid-phase amplification In addition to any of the above methods, generating transcriptomic data may include contacting a sample with particles such that the particles adsorb biomolecules comprising RNA. The adsorbed RNA may be part of a biomolecule corona. The adsorbed RNA may be measured or identified in generating the transcriptomic data.

v. Genomic Data

A data set may include genomic data or data on genetic material (such as genetic material measurements). Genomic data may include data about genetic material such as nucleic acids or histones. The nucleic acids may include DNA. Genomic data may include information on the presence, absence, or amount of the genetic material. An amount of genetic material may be indicated as a concentration, absolute number, or may be relative.

Genomic data may include DNA sequence data. The sequence data may include gene sequences. For example, the genomic data may include sequence data for up to about 20,000 genes. The genomic data may also include sequence data for non-coding DNA regions. DNA sequence data may include information on the presence, absence, or amount of DNA sequences. The DNA sequence data may include information on the presence or absence of a mutation such as a single nucleotide polymorphism. The DNA sequence data may include DNA measurement of an amount of mutated DNA, for example a measurement of mutated DNA from cancer cells.

Genomic data may include epigenetic data. Examples of epigenetic data include DNA methylation data, DNA hydroxymethylation data, or histone modification data. Epigenetic data may include DNA methylation or hydroxymethylation. DNA methylation or hydroxymethylation may be measured in whole or at regions within the DNA. Methylated DNA may include methylated cytosine (e.g. 5-methylcytosine). Cytosine is often methylated at CpG sites and may be indicative of gene activation.

Epigenetic data may include histone modification data. Histone modification data may include the presence, absence, or amount of a histone modification. Examples of histone modifications include serotonylation, methylation, citrullination, acetylation, or phosphorylation. Some specific examples of histone modifications may include lysine methylation, glutamine serotonylation, arginine methylation, arginine citrullination, lysine acetylation, serine phosphorylation, threonine phosphorylation, or tyrosine phosphorylation. Histone modifications may be indicative of gene activation.

Genomic data may be distinguished by type, where each type includes a different type of genomic data. For example, DNA sequence data may be included in another type, and epigenetic data may be included in one type, or different types of epigenetic data may be included in different types.

Genomic data may be generated by any of a variety of methods. Generating genomic data may include using a detection reagent that binds to a genetic material such as DNA or histones and yields a detectable signal. After use of a detection reagent that binds to genetic material and yields a detectable signal, a readout may be obtained that is indicative of the presence, absence or amount of the genetic material. Generating genomic data may include concentrating, filtering, or centrifuging a sample.

Some examples of methods for generating DNA sequence data include use of sequencing, microarray analysis (e.g. a SNP microarray), hybridization, polymerase chain reaction, or electrophoresis, or a combination thereof. DNA sequence data may be generated by sequencing a subject's DNA. Sequencing may include massive parallel sequencing. Examples of massive parallel sequencing techniques include pyrosequencing, sequencing by reversible terminator chemistry, sequencing-by-ligation mediated by ligase enzymes, or phospholinked fluorescent nucleotides or real-time sequencing. Generating genomic data may include preparing a sample or template for sequencing. Some template preparation methods include use of amplified templates originating from single DNA molecules, or single DNA molecule templates. Examples of amplification methods include emulsion PCR, rolling circle, or solid-phase amplification DNA methylation can be detected by use of mass spectrometry, methylation-specific PCR, bisulfite sequencing, a HpaII tiny fragment enrichment by ligation-mediated PCR assay, a GlaI hydrolysis and ligation adapter dependent PCR assay, a chromatin immunoprecipitation (ChIP) assay combined with a DNA microarray (a ChIP-on-chip assay), restriction landmark genomic scanning, methylated DNA immunoprecipitation, pyrosequencing of bisulfite treated DNA, a molecular break light assay for DNA adenine methyltransferase activity, methyl sensitive Southern blotting, methylCpG binding proteins, high resolution melt analysis, a methylation sensitive single nucleotide primer extension assay, another methylation assay, or a combination thereof.

Histone modifications may be detected by using mass spectrometry or an immunoassay, an enzyme-linked immunosorbent assay, a western blot, a dot blot, or immunostaining, or a combination thereof.

In addition to any of the above methods, generating genomic data may include contacting a sample with particles such that the particles adsorb biomolecules comprising genetic material. The adsorbed genetic material may be part of a biomolecule corona. The adsorbed genetic material may be measured or identified in generating the genomic data.

vi. Metabolomic Data

A data set may include metabolomic data or metabolite data (such as metabolite measurements). Metabolomic data may include information on small-molecule (e.g., less than kDa) metabolites (such as metabolic intermediates, hormones or other signaling molecules, or secondary metabolites). Metabolomic data may involve data about metabolites. Metabolites may include are substrates, intermediates or products of metabolism. A metabolite may be any molecule less than 1.5 kDa in size. Examples of metabolites may include sugars, lipids, amino acids, fatty acids, phenolic compounds, or alkaloids. Metabolomic data may be distinguished by type, where each type includes a different type of metabolite. Metabolomic data may include lipidomic data.

Metabolomic data or metabolite data may include lipidomic data or lipid data. Lipids may be an integral component in the development of cancer. For example, lipids may be key players in cancer biology, as they may affect or be involved in feeding membrane and cell proliferation, lipotoxicity (where lipid content balance may aid in protection from lipotoxicity), empowering cellular processes, membrane biophysics, oncogenic signaling and metastasis, protection from oxidative stress, signaling in the microenvironment, or immune-modulation. Some lipid classes may be relevant to cancers, such as glycerophospholipids in hepatocellular carcinomas, glycerophospholipids and acylcarnitines in prostate cancer, choline containing lipids and phospholipids increase during metastasis, or sphingolipid regulation of cancer cell survival and death.

Metabolomic data may include information on the presence, absence, or amount of various metabolites. For example, metabolomic data may include amounts of metabolites. A metabolite amount may be indicated as a concentration or quantity of metabolites, for example a concentration of a metabolite in a biological sample. A metabolite amount may be relative to another metabolite or to another biomolecule. Metabolomic data may include information on the presence of metabolites. Metabolomic data may include information on the absence of metabolites.

Metabolomic data generally includes data on a number of metabolites. For example, metabolomic data may include information on the presence, absence, or amount of 1000 or more metabolites. In some cases, metabolomic data may include information on the presence, absence, or amount of 5000, 10,000, 20,000, 50,000, 100,000, 500,000, 1 million, 1.5 million, 2 million, or more metabolites, or a range of metabolites defined by any two of the aforementioned numbers of metabolites.

Metabolomic data may be generated by any of a variety of methods. Generating metabolomic data may include using a detection reagent that binds to a metabolite and yields a detectable signal. After use of a detection reagent that binds to a metabolite and yields a detectable signal, a readout may be obtained that is indicative of the presence, absence or amount of the metabolite. Generating metabolomic data may include concentrating, filtering, or centrifuging a sample.

Metabolomic data may be generated using mass spectrometry, chromatography, liquid chromatography, high-performance liquid chromatography, solid-phase chromatography, a lateral flow assay, an immunoassay, an enzyme-linked immunosorbent assay, a western blot, a dot blot, or immunostaining, or a combination thereof. An example of a method for generating metabolomic data includes using mass spectrometry. Mass spectrometry may include a separation method step such as liquid chromatography (e.g., HPLC). Mass spectrometry may include an ionization method such as electron ionization, atmospheric-pressure chemical ionization, electrospray ionization, or secondary electrospray ionization. Mass spectrometry may include surface-based mass spectrometry or secondary ion mass spectrometry. Another example of a method for generating metabolomic data includes nuclear magnetic resonance (NMR). Other examples of methods for generating metabolomic data include Fourier-transform ion cyclotron resonance, ion-mobility spectrometry, electrochemical detection (e.g. coupled to HPLC), or Raman spectroscopy and radiolabel (e.g. when combined with thin-layer chromatography). Some mass spectrometry methods described for generating metabolomic data may be used for generating proteomic data, or vice versa. Metabolomic data may also be generated using a immunoassays such as enzyme-linked immunosorbent assays, western blots, dot blots, or immunohistochemistry. Generating metabolomic data may involve use of a lipid panel.

In addition to any of the above methods, generating metabolomic data may include contacting a sample with particles such that the particles adsorb biomolecules comprising metabolites. The adsorbed metabolites may be part of a biomolecule corona. The adsorbed metabolites may be measured or identified in generating the metabolomic data.

d. Computer Systems

Certain aspects of the methods described herein may be carried out using a computer system. For example, analysis of a data set may be carried out using a computer system. Likewise, a data set may be obtained through the use of a computer system. A readout indicative of the presence, absence or amount of a biomolecule (e.g. protein, transcript, genetic material, or metabolite) may be obtained at least in part using a computer system. The computer system may be used to carry out a method of using a classifier to assign a label corresponding to a presence, absence, or likelihood of a disease state to a data set, or to identify the data set as indicative or as not indicative of the disease state. The computer system may generate a report identifying a likelihood of the subject having a disease state. The computer system may transmit the report. For example, a laboratory may transmit a report regarding the disease state identification to a medical practitioner. A computer system may receive a report.

Figure 4:
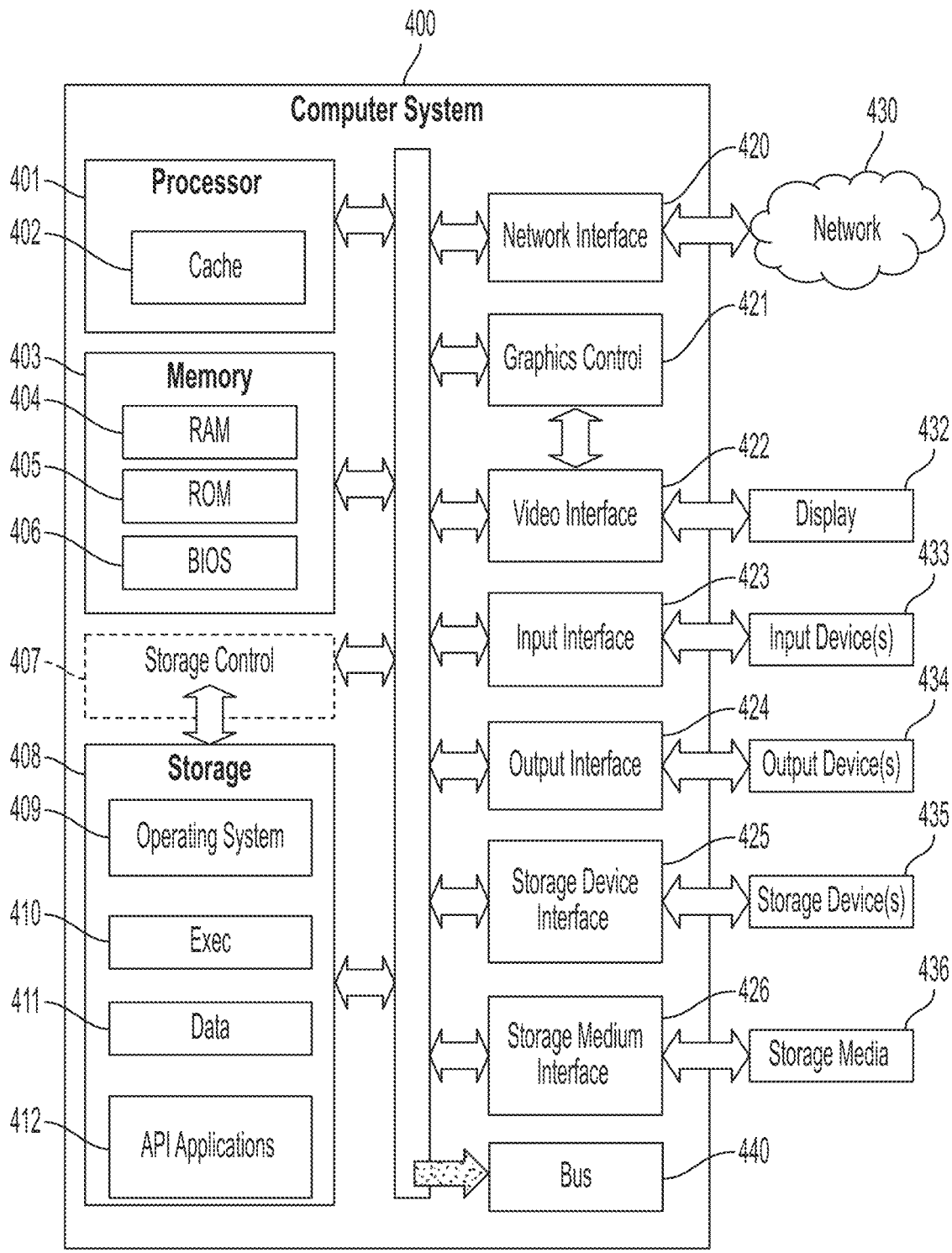
FIG. 4 shows a non-limiting example of a computing device that may include a processor, memory, storage, or network interface.

A computer system that carries out a method described herein may include some or all of the components shown in FIG. 4. Referring to FIG. 4, a block diagram is shown depicting an example of a machine that includes a computer system 400 (e.g., a processing or computing system) within which a set of instructions can execute for causing a device to perform or execute any one or more of the aspects and/or methodologies for static code scheduling of the present disclosure. The components in FIG. 4 are examples, and do not limit the scope of use or functionality of any hardware, software, embedded logic component, or a combination of two or more such components implementing particular aspects.

Computer system 400 may include one or more processors 401, a memory 403, and a storage 408 that communicate with each other, and with other components, via a bus 440. The bus 440 may also link a display 432, one or more input devices 433 (which may, for example, include a keypad, a keyboard, a mouse, a stylus, etc.), one or more output devices 434, one or more storage devices 435, and various tangible storage media 436. All of these elements may interface directly or via one or more interfaces or adaptors to the bus 440. For instance, the various tangible storage media 436 can interface with the bus 440 via storage medium interface 426. Computer system 400 may have any suitable physical form, including but not limited to one or more integrated circuits (ICs), printed circuit boards (PCBs), mobile handheld devices (such as mobile telephones or PDAs), laptop or notebook computers, distributed computer systems, computing grids, or servers.

Computer system 400 includes one or more processor(s) 401 (e.g., central processing units (CPUs) or general purpose graphics processing units (GPGPUs)) that carry out functions. Processor(s) 401 optionally contains a cache memory unit 402 for temporary local storage of instructions, data, or computer addresses. Processor(s) 401 are configured to assist in execution of computer readable instructions. Computer system 400 may provide functionality for the components depicted in FIG. 4 as a result of the processor(s) 401 executing non-transitory, processor-executable instructions embodied in one or more tangible computer-readable storage media, such as memory 403, storage 408, storage devices 435, and/or storage medium 436. The computer-readable media may store software that implements particular aspects, and processor(s) 401 may execute the software. Memory 403 may read the software from one or more other computer-readable media (such as mass storage device(s) 435, 436) or from one or more other sources through a suitable interface, such as network interface 420. The software may cause processor(s) 401 to carry out one or more processes or one or more steps of one or more processes described or illustrated herein. Carrying out such processes or steps may include defining data structures stored in memory 403 and modifying the data structures as directed by the software.

The memory 403 may include various components (e.g., machine readable media) including, but not limited to, a random access memory component (e.g., RAM 404) (e.g., static RAM (SRAM), dynamic RAM (DRAM), ferroelectric random access memory (FRAM), phase-change random access memory (PRAM), etc.), a read-only memory component (e.g., ROM 405), and any combinations thereof. ROM 405 may act to communicate data and instructions unidirectionally to processor(s) 401, and RAM 404 may act to communicate data and instructions bidirectionally with processor(s) 401. ROM 405 and RAM 404 may include any suitable tangible computer-readable media described below. In one example, a basic input/output system 406 (BIOS), including basic routines that help to transfer information between elements within computer system 400, such as during start-up, may be stored in the memory 403.

Fixed storage 408 is connected bidirectionally to processor(s) 401, optionally through storage control unit 407. Fixed storage 408 provides additional data storage capacity and may also include any suitable tangible computer-readable media described herein. Storage 408 may be used to store operating system 409, executable(s) 410, data 411, applications 412 (application programs), and the like. Storage 408 can also include an optical disk drive, a solid-state memory device (e.g., flash-based systems), or a combination of any of the above. Information in storage 408 may, in appropriate cases, be incorporated as virtual memory in memory 403.

In one example, storage device(s) 435 may be removably interfaced with computer system 400 (e.g., via an external port connector (not shown)) via a storage device interface 425. Particularly, storage device(s) 435 and an associated machine-readable medium may provide non-volatile and/or volatile storage of machine-readable instructions, data structures, program modules, and/or other data for the computer system 400. In one example, software may reside, completely or partially, within a machine-readable medium on storage device(s) 435. In another example, software may reside, completely or partially, within processor(s) 401.

Bus 440 connects a wide variety of subsystems. Herein, reference to a bus may encompass one or more digital signal lines serving a common function, where appropriate. Bus 440 may be any of several types of bus structures including, but not limited to, a memory bus, a memory controller, a peripheral bus, a local bus, and any combinations thereof, using any of a variety of bus architectures. As an example and not by way of limitation, such architectures may include an Industry Standard Architecture (ISA) bus, an Enhanced ISA (EISA) bus, a Micro Channel Architecture (MCA) bus, a Video Electronics Standards Association local bus (VLB), a Peripheral Component Interconnect (PCI) bus, a PCI-Express (PCI-X) bus, an Accelerated Graphics Port (AGP) bus, HyperTransport (HTX) bus, serial advanced technology attachment (SATA) bus, or any combination thereof.

Computer system 400 may also include an input device 433. In one example, a user of computer system 400 may enter commands and/or other information into computer system 400 via input device(s) 433. Examples of an input device(s) 433 include, but are not limited to, an alphanumeric input device (e.g., a keyboard), a pointing device (e.g., a mouse or touchpad), a touchpad, a touch screen, a multi-touch screen, a joystick, a stylus, a gamepad, an audio input device (e.g., a microphone, a voice response system, etc.), an optical scanner, a video or still image capture device (e.g., a camera), or any combinations thereof. The input device may include a Kinect, Leap Motion, or the like. Input device(s) 433 may be interfaced to bus 440 via any of a variety of input interfaces 423 (e.g., input interface 423) including, but not limited to, serial, parallel, game port, USB, FIREWIRE, THUNDERBOLT, or any combination of the above.

When computer system 400 is connected to network 430, computer system 400 may communicate with other devices, specifically mobile devices and enterprise systems, distributed computing systems, cloud storage systems, cloud computing systems, and the like, connected to network 430. Communications to and from computer system 400 may be sent through network interface 420. For example, network interface 420 may receive incoming communications (such as requests or responses from other devices) in the form of one or more packets (such as Internet Protocol (IP) packets) from network 430, and computer system 400 may store the incoming communications in memory 403 for processing. Computer system 400 may similarly store outgoing communications (such as requests or responses to other devices) in the form of one or more packets in memory 403 and communicated to network 430 from network interface 420. Processor(s) 401 may access these communication packets stored in memory 403 for processing.

Examples of the network interface 420 include, but are not limited to, a network interface card, a modem, or any combination thereof. Examples of a network 430 or network segment 430 include, but are not limited to, a distributed computing system, a cloud computing system, a wide area network (WAN) (e.g., the Internet, an enterprise network), a local area network (LAN) (e.g., a network associated with an office, a building, a campus or other relatively small geographic space), a telephone network, a direct connection between two computing devices, a peer-to-peer network, or any combinations thereof. A network, such as network 430, may employ a wired and/or a wireless mode of communication. In general, any network topology may be used.

Information and data can be displayed through a display 432. Examples of a display 432 include, but are not limited to, a cathode ray tube (CRT), a liquid crystal display (LCD), a thin film transistor liquid crystal display (TFT-LCD), an organic liquid crystal display (OLED) such as a passive-matrix OLED (PMOLED) or active-matrix OLED (AMOLED) display, a plasma display, or any combinations thereof. The display 432 can interface to the processor(s) 401, memory 403, and fixed storage 408, as well as other devices, such as input device(s) 433, via the bus 440. The display 432 is linked to the bus 440 via a video interface 422, and transport of data between the display 432 and the bus 440 can be controlled via the graphics control 421. The display may be a video projector. The display may be a head-mounted display (HMD) such as a VR headset. Suitable VR headsets may include HTC Vive, Oculus Rift, Samsung Gear VR, Microsoft HoloLens, Razer OSVR, FOVE VR, Zeiss VR One, Avegant Glyph, Freefly VR headset, or the like. The display may include a combination of devices such as those disclosed herein.

In addition to a display 432, computer system 400 may include one or more other peripheral output devices 434 including, but not limited to, an audio speaker, a printer, a storage device, or any combinations thereof. Such peripheral output devices may be connected to the bus 440 via an output interface 424. Examples of an output interface 424 include, but are not limited to, a serial port, a parallel connection, a USB port, a FIREWIRE port, a THUNDERBOLT port, or any combinations thereof.

In addition or as an alternative, computer system 400 may provide functionality as a result of logic hardwired or otherwise embodied in a circuit, which may operate in place of or together with software to execute one or more processes or one or more steps of one or more processes described or illustrated herein. Reference to software in this disclosure may encompass logic, and reference to logic may encompass software. Moreover, reference to a computer-readable medium may encompass a circuit (such as an IC) storing software for execution, a circuit embodying logic for execution, or both, where appropriate. The present disclosure encompasses any suitable combination of hardware, software, or both.

Those of skill in the art will appreciate that the various illustrative logical blocks, modules, circuits, and algorithm steps described in connection with aspects disclosed herein may be implemented as electronic hardware, computer software, or combinations of both. To clearly illustrate this interchangeability of hardware and software, various illustrative components, blocks, modules, circuits, and steps have been described above generally in terms of their functionality.

The various illustrative logical blocks, modules, and circuits described in connection with aspects disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with aspects disclosed herein may be embodied directly in hardware, in a software module executed by one or more processor(s), or in a combination of the two. A software module may reside in RAM memory, flash memory, ROM memory, EPROM memory, EEPROM memory, registers, hard disk, a removable disk, a CD-ROM, or any other form of storage medium. An example storage medium is coupled to the processor such the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

In accordance with the description herein, suitable computing devices may include, by way of non-limiting examples, server computers, desktop computers, laptop computers, notebook computers, sub-notebook computers, netbook computers, netpad computers, set-top computers, media streaming devices, handheld computers, Internet appliances, mobile smartphones, tablet computers, personal digital assistants, video game consoles, and vehicles. Those of skill in the art will also recognize that select televisions, video players, and digital music players with optional computer network connectivity are suitable for use in the system described herein. Suitable tablet computers may include those with booklet, slate, or convertible configurations.

The computing device may include an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. The operating system may be provided by cloud computing. Those of skill in the art will also recognize that suitable mobile smartphone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®.

In some cases, the platforms, systems, media, or methods disclosed herein include one or more non-transitory computer readable storage media encoded with a program including instructions executable by an operating system of a computer system. The computer system may be networked. A computer readable storage medium may be a tangible component of a computing device. A computer readable storage medium may be removable from a computing device. A computer readable storage medium may include any of, by way of non-limiting examples, CD-ROMs, DVDs, flash memory devices, solid state memory, magnetic disk drives, magnetic tape drives, optical disk drives, distributed computing systems including cloud computing systems and services, or the like. In some cases, the program and instructions are permanently, substantially permanently, semi-permanently, or non-transitorily encoded on the media.

e. Data Integration and Analysis

Disclosed herein, are methods that include obtaining multiple sets of measurements. The multiple sets of measurements may include measurements of endogenous biomolecules adsorbed to particles and measurements of internal standard biomolecules combined with the biological sample, or combined with the endogenous biomolecules adsorbed to the particles. A method may include obtaining measurements of endogenous biomolecules adsorbed to particles from a biological sample of a subject. A method may include obtaining measurements of internal standard biomolecules combined with the biological sample, or combined with the endogenous biomolecules adsorbed to the particles. The internal standard biomolecules may be the same as the endogenous biomolecules but also comprise a label. A method may include normalizing or adjusting the measurements of the endogenous biomolecules based on the measurements of the internal standard biomolecules. A method may include applying a classifier to the normalized or adjusted measurements to assign a label corresponding to a biological state to the normalized or adjusted measurements.

Combining different data sets can lead to unprecedented results in terms of scale, diversity and richness. Each sample can be profiled to derive data sets using different methods, and the results can be combined with clinical information. Artificial intelligence may be used to discover patterns and interactions that drive clinical differences. Deep learning algorithms will be developed that may include aspects of computer vision, natural language processing, or unsupervised learning to discover patterns in the results and identify biomarkers which can help drive discrimination of disease states in subjects. The methods may be used widely across the process from processing raw results to developing robust classifiers.

Separate data sets may be integrated into an analysis for more accurate prediction or identification of a disease than individual data sets would provide for. For example, a method may include using more than one classifier to identify a disease state in a subject, where each classifier is used to analyze a separate data set and each classifier is independent of the other. If the classifiers err independently from each other, the combined analysis may be more accurate than an analysis using one classifier corresponding to only one data set. Alternatively, separate data sets may be combined into one data set or analyzed by a single classifier.

A method involving multiple classifiers may include using a first classifier to generate or assign a first label corresponding to a presence, absence, or likelihood of a disease state to a first data set. The method may further include using a second classifier to generate or assign a second label corresponding to a presence, absence, or likelihood of a disease state to a second data set. The method may further include using a third classifier to generate or assign a third label corresponding to a presence, absence, or likelihood of a disease state to a third data set. The method may further include using a fourth classifier to generate or assign a fourth label corresponding to a presence, absence, or likelihood of a disease state to a fourth data set. Additional classifiers may be used to generate or assign labels to further data sets. Each classifier may be trained using data or combined data from samples of diseased and control subjects. Further, each classifier may include a stand-alone machine learning model or an ensemble of machine-learning models trained on the same input features. Classifiers may be trained using computer vision, natural language processing, or unsupervised learning, or a combination thereof.

Classifiers may be trained using data sets from multiple samples, for example thousands of samples.

Some classifiers may analyze a combined data set, whereas other classifiers may analyze one data set. For example, an additional classifier may generate or assign a label corresponding to a presence, absence, or likelihood of a disease state to a combined data set. The combined data set may include any combination of two or more types data. For example, data types may include proteomic data, transcriptomic data, genomic data, or metabolomic data. The combined data set may include a combination of two or more different types of measurement of a biomolecule type. For example, the combined data may include protein measurements obtained using particles, as well as protein measurements obtained using internal standards.

The labels generated or assigned by each classifier may be used to identify the data set as indicative or as not indicative of the disease state. This may entail identifying the data set as indicative or as not indicative of the disease state based on a single label assigned by any one or more of the classifiers, or by generating or obtaining a majority voting score based on the first and second labels.

Identifying the data set as indicative or as not indicative of the disease state may include majority voting across of some or all of the classifier-generated labels. For example, the final determination of whether the subject is likely to have the disease state or not may be identified based on whether more classifiers assigned labels corresponding to the presence of the disease state or whether more classifiers assigned labels corresponding to the absence of the disease state. Identifying the data set as indicative or as not indicative of the disease state may include generating or using a weighted average of some or all of the classifier-generated labels.

Identifying the data set as indicative or as not indicative of the disease state may include obtaining or generating a weighted average of the labels generated or assigned by some or all of the classifiers. Weights of the weighted average may be based on one or more of: area under a ROC curve, area under a precision-recall curve, accuracy, precision, recall, sensitivity, F1-score, or specificity, or a combination thereof.

A method involving multiple classifiers may include identifying a data set as indicative or as not indicative of a disease state. This may be done based on choosing a label assigned by an individual classifier, or by combining the labels assigned by multiple classifiers. The method may include identifying a data set as indicative or as not indicative of the disease state based on a combination of a first label and a second label, each assigned by separate classifiers. The data set may be identified as indicative of the disease state based further on a third label, a fourth label, or one or more additional labels. The data set may be identified as indicative of the disease state based on a first and third label, or based on a first and fourth label, where, for example, one or more of the labels are not included in the final determination.

Figure 2:
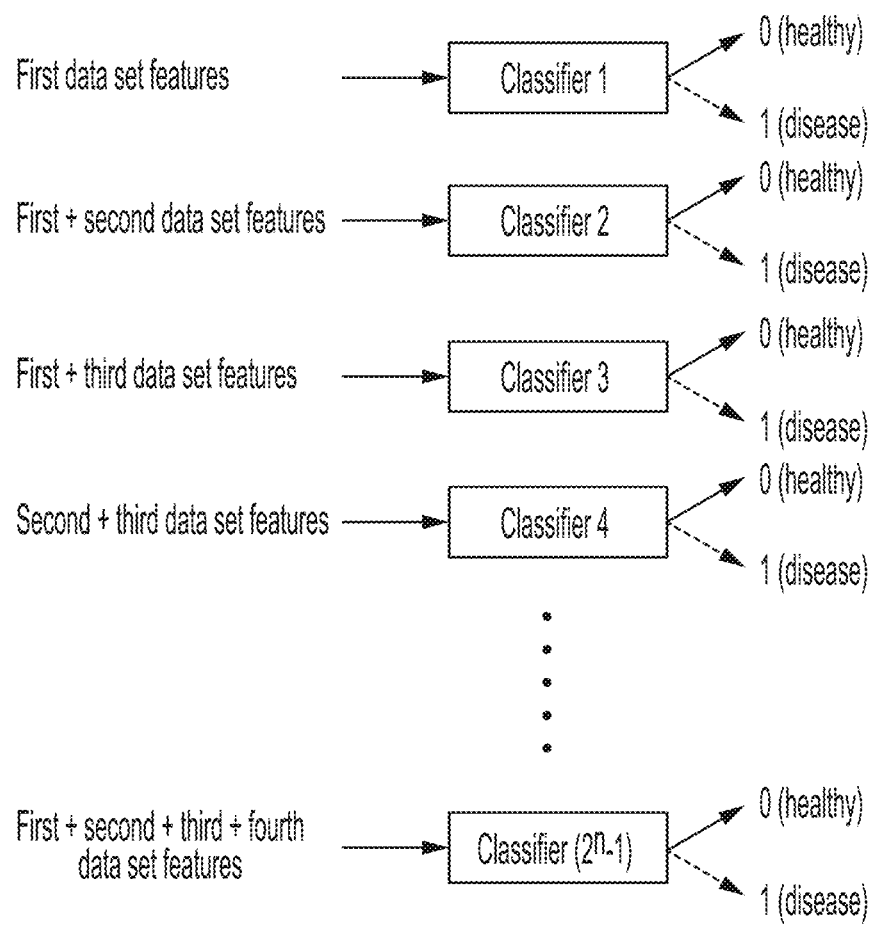
FIG. 2 is a diagram of examples of data processing.

An example of a method involving multiple classifiers is shown in FIG. 2. In the example, an ensemble of classifiers are trained to make a cancer/healthy call based on features from proteomic, metabolomic, genomic, and transcriptomic results. Each classifier takes a combination of features from the n data sets for a total of $(2n-1)$ different classifiers. Further, each classifier can be a stand-alone machine learning model or an ensemble of machine-learning models trained on the same input features. A final call may be made by any of the following methods: picking an output of any one of the classifiers; majority voting across all of the classifiers or across a subset of the classifiers; or obtaining a weighted average of outputs of all of the classifiers or a subset of the classifiers, where weights are assigned based on area under ROC curve, area under precision-recall curve, accuracy, precision, recall/sensitivity, F1-score, or specificity.

A method may include integrated models classification. A method using integrated models classification may include combining predicted probabilities or classifier calls of classifiers trained on each analyte or data type separately. Combination of probabilities can be via taking a weighted mean with weights assigned according to AUC. In some cases, a first classifier generates a prediction or label for a first data set, a second classifier generates a prediction or label for a second data set, optionally one or more additional classifiers each generate a prediction or label for one or more additional data sets, and the predictions or label are combined. The combined predictions or labels may be used in identifying a data set as indicative or as not indicative of a disease state. Some aspects relate to a combined classifier for use in a method described herein, such as a method that includes use of integrated models classification. Some aspects relate to a set of classifiers for use in a method described herein, such as a method that includes use of integrated models classification.

A method may include transformation-based classification. Transformation-based classification may include picking top features from each analyte or data type, pool the features, and train one classifier on the pooled features. Transformation-based classification may include any of the following 3 methods:

First method: top features can be picked by training a "pre" classifier first and looking at the top features.

Second Method: another way is to perform a univariate analysis and pick the differentially abundant features for each analyte or data type.

Third method: remove one feature at a time and look at drop in the "pre" classifier performance (AUC). Those which cause the highest drop in performance may be the top features for that particular analyte or data type.

Some aspects relate to a classifier generated using one of these methods, for use in a method described herein. For example, some aspects include a classifier trained by: identifying a subset of features from among a first data set; identifying a subset of features from among the second data set; pooling the subsets of features from among the first and second data sets to generate pooled features; and training the classifier with the pooled features to identify data sets comprising the first and second data sets as indicative or as not indicative of a disease state.

The classifier may include a subset of features identified and pooled from separate data sets. The features may be identified by obtaining univariate data for features of a data set, and identifying top features from among the univariate data. The subset of features may be identified from among features of classifiers for the separate data sets. The features may be identified by obtaining a classifier for a data set, and identifying top features of the classifier. The features may be identified by obtaining a classifier for a data set, removing one or more features at time from the classifier, and identifying which features reduce the classifier's performance the most when removed from the classifier. Artificial intelligence or machine learning methods may be useful to develop classifiers based on the data set described herein, particularly when using larger data sets or when using a combination of several different types of data sets.

Transformation-based classification may be useful in that it may reduce the number of features to be used in an analysis. For example, transformation-based classification may reduce the number of features to be used in an analysis from 1000's to less than 100 (e.g. 10 to 30, 10 to 50, or 10 to 75) or perhaps a few dozen. This may speed up computer processing in, for example, identifying data sets as indicative or as not indicative of a disease state, because it may reduce the amount of computations to be processed relative to a method using a non-reduced number of features.

The methods described herein, when analyzing data described herein such as proteomic data, transcriptomic data, genomic data, or metabolomic data, can include generating or using a classifier for indicating the subject of having or at risk of having a disease with a certain sensitivity or specificity. A method described herein may generate or use a classifier from the data for indicating the subject of having or at risk of having a disease with a sensitivity of at least about 50%, at least about 60%, at least about 70%, at least about 80%, or at least about 90%. A method described herein may generate or use a classifier from the data for indicating the subject of having or at risk of having a disease with a specificity of at least about 50%, at least about 60%, at least about 70%, at least about 80%, or at least about 90%. A method described herein may generate or use a classifier from the data for indicating the subject of having or at risk of having a disease with a sensitivity or specificity no greater than about 50%, no greater than about 60%, no greater than about 70%, no greater than about 80%, no greater than about 90%, or no greater than about 95%.

Some aspects include identifying a biological state of the subject based on the endogenous biomolecule measurements. Some aspects include outputting or transmitting a report comprising information on the identified biological state. Some aspects include transmitting or outputting a recommendation of a treatment of the subject based on the identified biological state.

f. Subjects and Treatment

The methods described herein may be used to identify a subject as likely to have a disease state or not. The subject may be an organism. The subject may be a vertebrate. The subject may be a mammal. The subject may be a human. The subject may be male or female. In some cases, the subject may be a plant, fungus, or other animal. The subject may be a microorganism. The microorganism may be a bacteria. The microorganism may include a virus. The subject may have a disease state. For example, the subject may have a disease or disorder, a comorbidity of a disease or disorder, or may be healthy.

A sample may be obtained from the subject for purposes of identifying a disease state in the subject. The subject may be suspected of having the disease state or as not having the disease state. The method may be used to confirm or refute the suspected disease state.

An example of a disease state is cancer. An example of cancer includes lung cancer. An example of lung cancer is non-small cell lung cancer (NSCLC). The cancer may be at an early stage or a late stage. The disease state may include a disease or disorder, or may include a comorbidity related to the disease or disorder.

In some cases the subject is monitored. For example, information about a likelihood of the subject having a disease state may be used to determine to monitor a subject without providing a treatment to the subject. In other circumstances, the subject may be monitored while receiving treatment to see if a disease state in the subject improves.

When the subject is identified as not having the disease state, the subject may avoid an otherwise unfavorable disease treatment (and associated side effects of the disease treatment), or is able to avoid having to be biopsied or tested invasively for the disease state. When the subject is identified as not having the disease state, the subject may be monitored without receiving a treatment. When the subject is identified as not having the disease state, the subject may be monitored without receiving a biopsy. In some cases, the subject identified as not having the disease state may be treated with palliative care such as a pharmaceutical composition for pain. In some cases, the subject is identified as having another disease different from the initially suspected disease state, and is provided treatment for the other disease.

When the subject is identified as having the disease state, the subject may be provided a treatment for the disease state. For example, if the disease state is cancer, the subject may be provided a cancer treatment. Examples of treatments include surgery, organ transplantation, administration of a pharmaceutical composition, radiation therapy, chemotherapy, immunotherapy, hormone therapy, monoclonal antibody treatment, stem cell transplantation, gene therapy, or chimeric antigen receptor (CAR)-T cell or transgenic T cell administration.

When the subject is identified as having the disease state, the subject may be further evaluated for the disease state. For example, a subject suspected of having the disease state may be subjected to a biopsy after a method disclosed herein indicates that he or she may have the disease state.

Some cases include recommending a treatment or monitoring of the subject. For example, a medical practitioner may receive a report generated by a method described herein. The report may indicate a likelihood of the subject having a disease state. The medical practitioner may then provide or recommend the treatment or monitoring to the subject or to another medical practitioner. Some cases include recommending a treatment for the subject. Some cases include recommending monitoring of the subject.

EXAMPLES

Example 1

Generation or Use of Disease State Classifiers with Multiple Data Sets

Proteomic and lipidomic measurements were obtained using liquid chromatography—mass spectrometry (LC-MS) in 83 plasma samples from human subjects with lung cancer (stage 1 NSCLC, n=17; and stage 2 NSCLC, n=7) or without lung cancer ("stage 0," n=59). Three separate classifiers were trained using proteomic or lipidomic measurements. Each separate classifier was used to output a predicted probability for cancer. In assessing combined classification data, the predicted probabilities outputted by each classifier were averaged.

The first classifier was trained using a first proteomic data set comprising measurements of proteins adsorbed from an aliquot of each plasma sample to nanoparticles. Features of the first classifier included measurements of proteins adsorbed separately to 10 separate commercially available nanoparticles (P-033, P-039, P-047, P-053, P-065, P-073, S-003, S-006, S-007, and S-010; Seer, Inc.). Separate measurements were obtained for each particle with each sample. Data from the first classifier are referred to as "Proteograph."

The second classifier was trained using a second proteomic data set comprising measurements of proteins from a separate aliquot of each plasma sample. Known amounts of commercially available, isotopically labeled, internal reference proteins were spiked into each plasma sample, were used to identify the mass spectra of individual endogenous proteins, and were used as standards for determining amounts of the individual endogenous proteins in the second proteomic data set. About 500 of the internal reference proteins were used to obtain measurements of about 500 individual endogenous proteins in each plasma sample. Data from the second classifier are referred to as "ProteinQuant" in this example.

The third classifier was trained using a lipidomic data set comprising measurements of lipids from another aliquot of each plasma sample. Data from the third classifier are referred to as "Lipid" in this example.

Figure 3A:
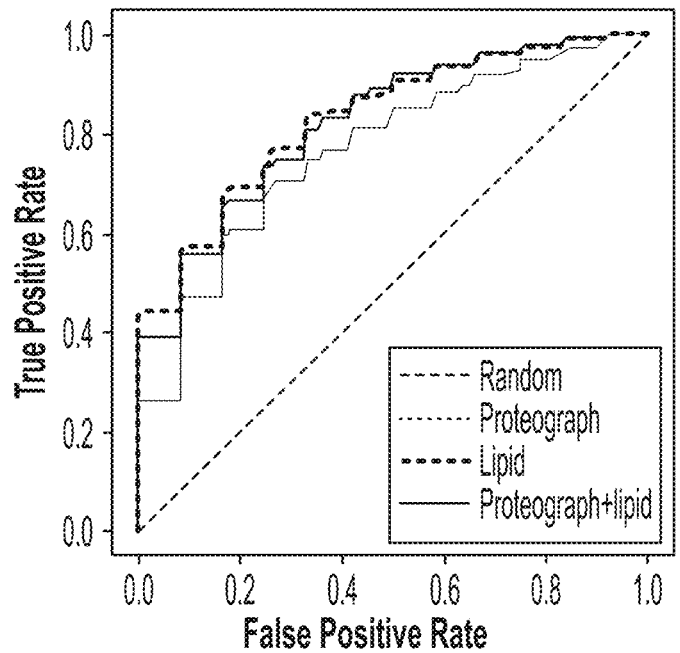
FIG. 3A includes plots depicting receiver operating characteristic curves (ROCs), in accordance with some aspects described herein.
Figure 3A:
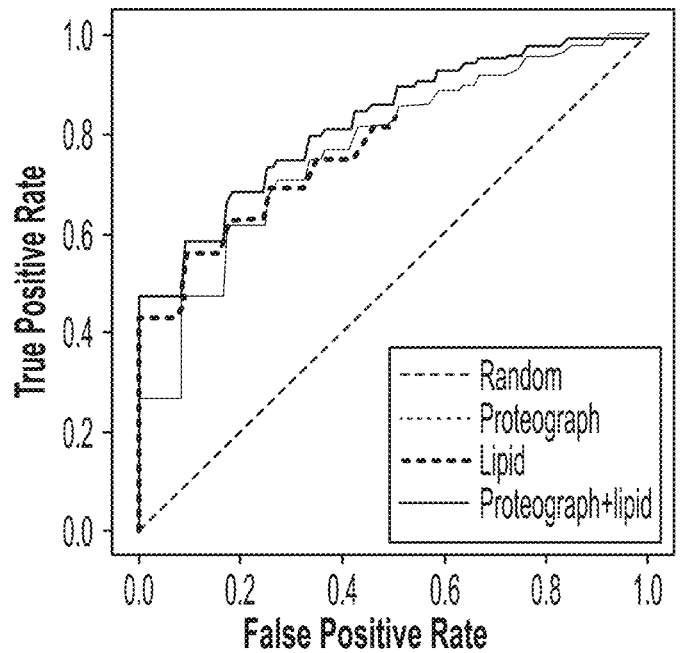
Figure 3A:
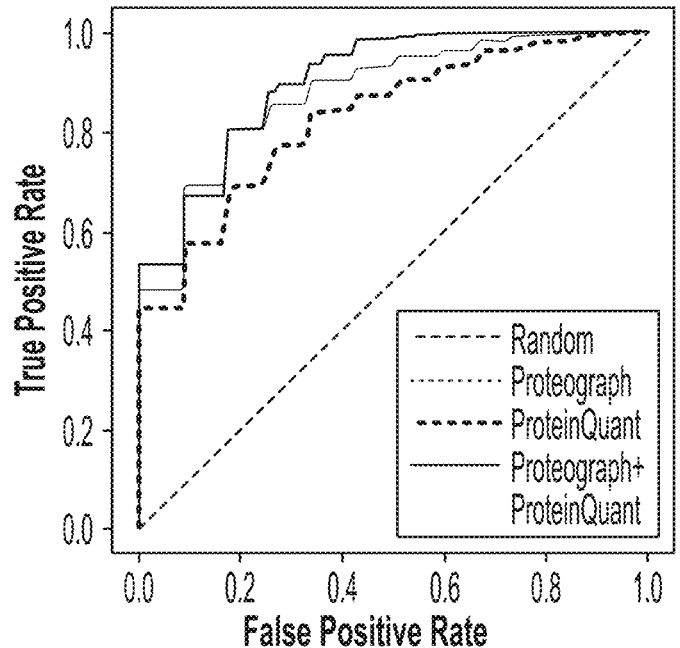
Figure 3A:
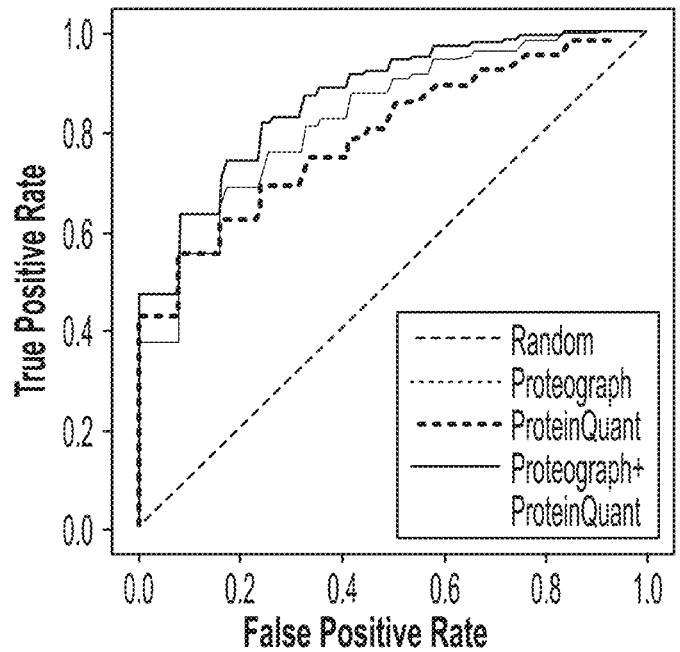
Figure 3A:
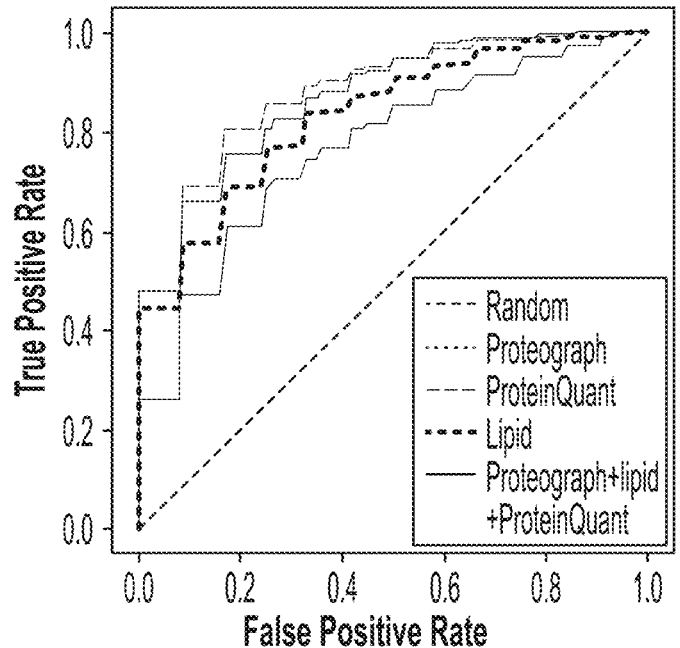
Figure 3A:
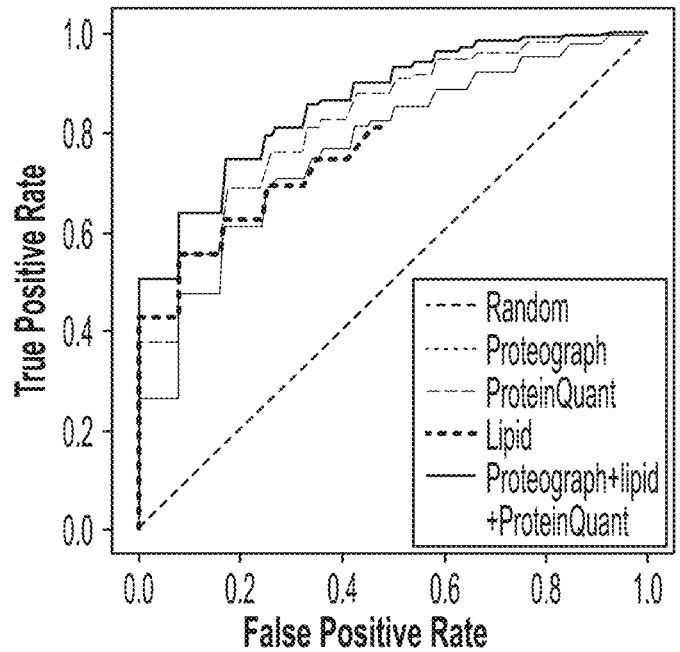
Figure 3B:
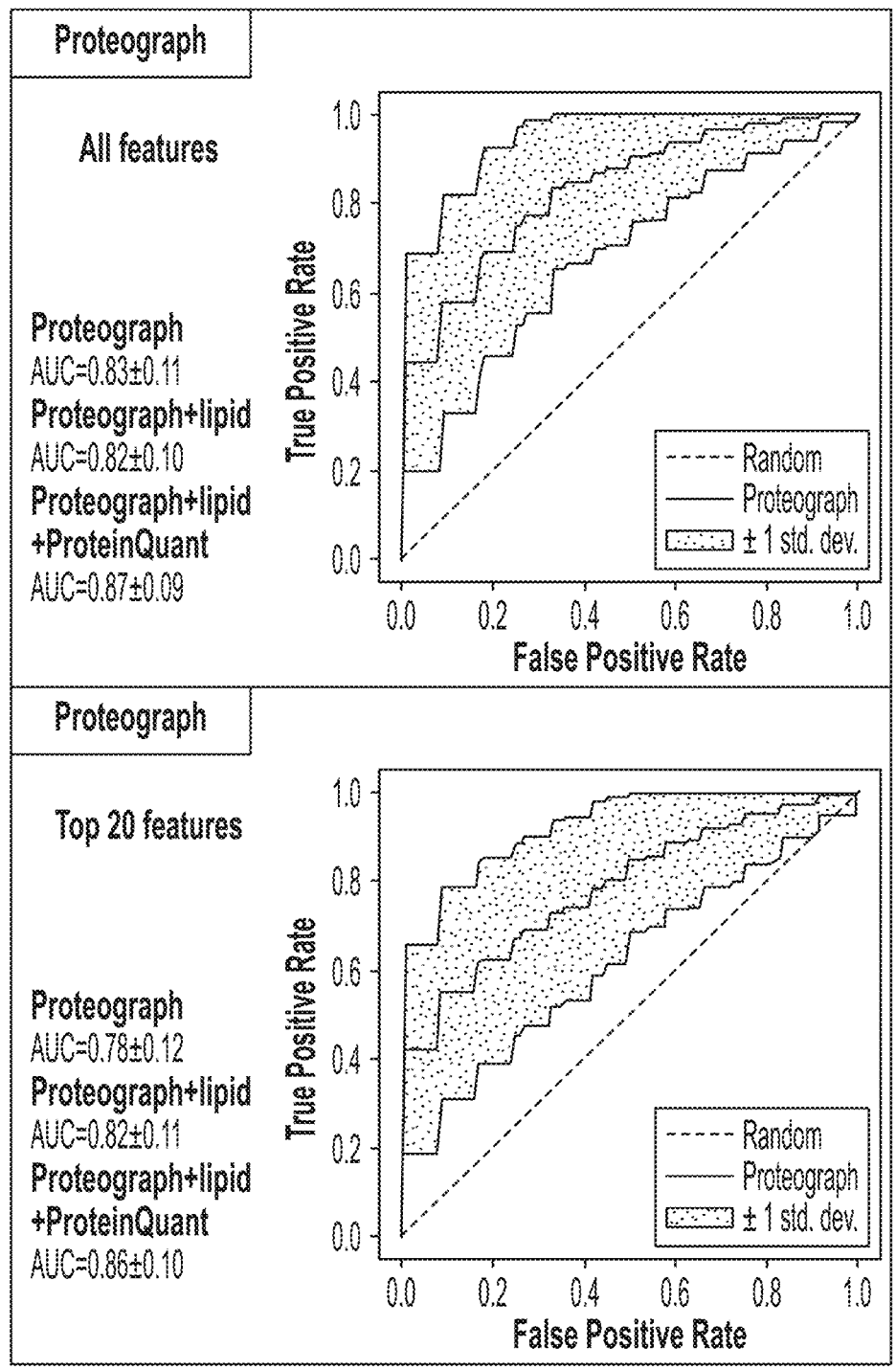
FIG. 3B includes plots depicting receiver operating characteristic curves (ROCs), in accordance with some aspects described herein.
Figure 3B:
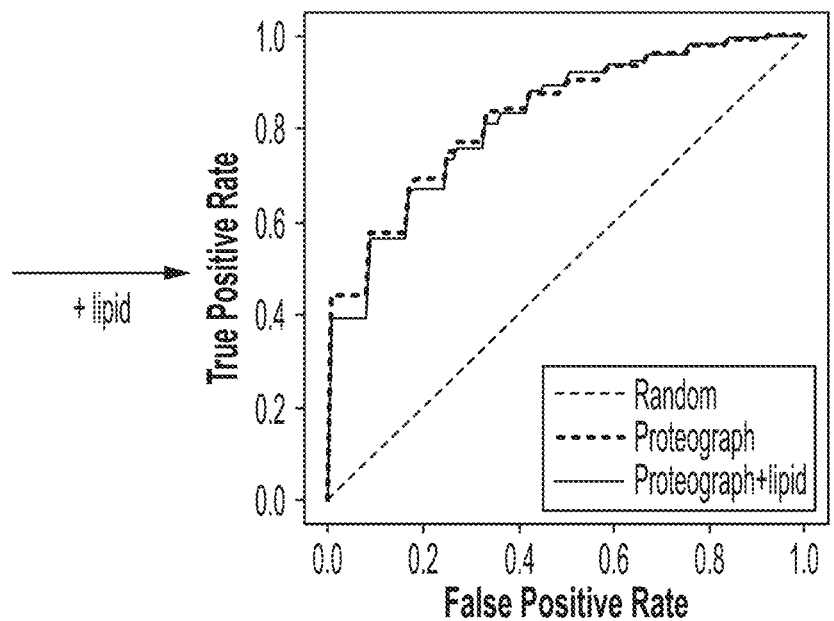
Figure 3B:
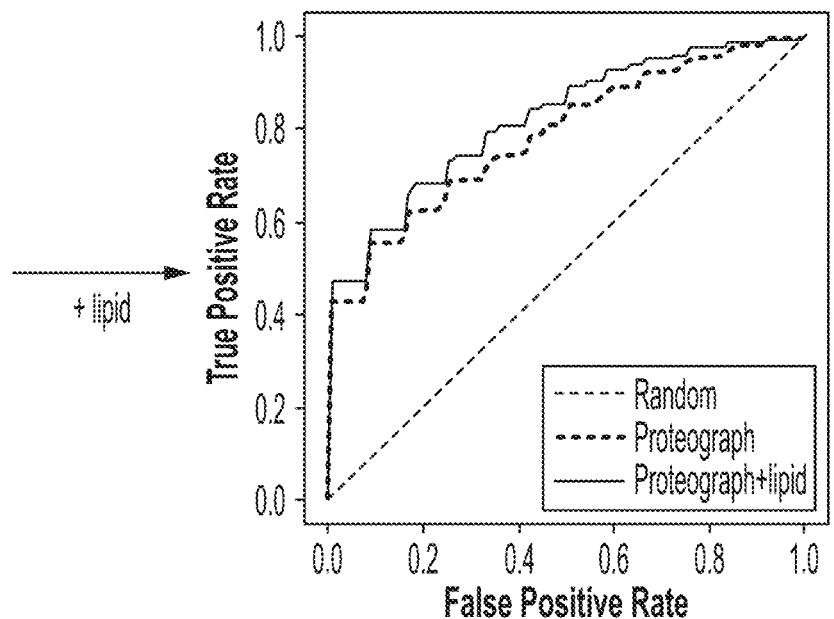
Figure 3B:
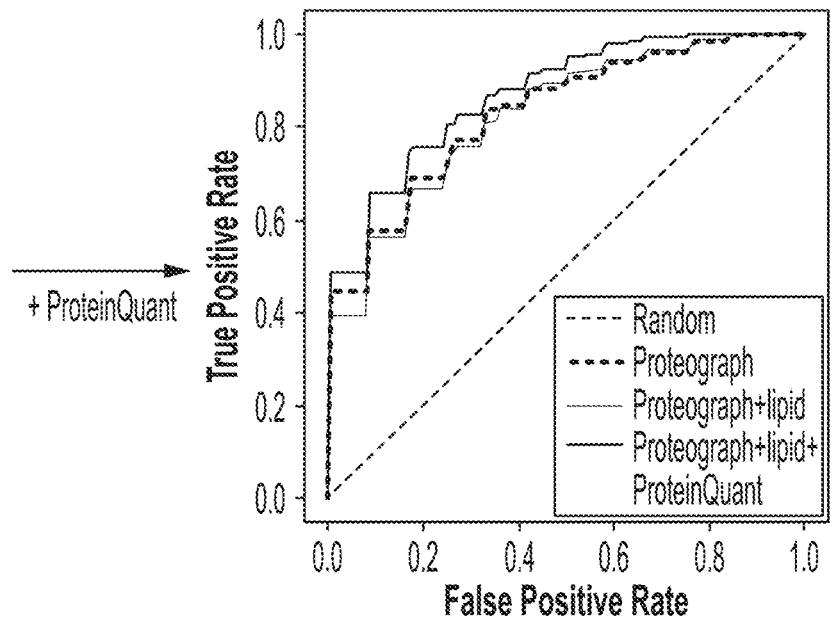
Figure 3B:
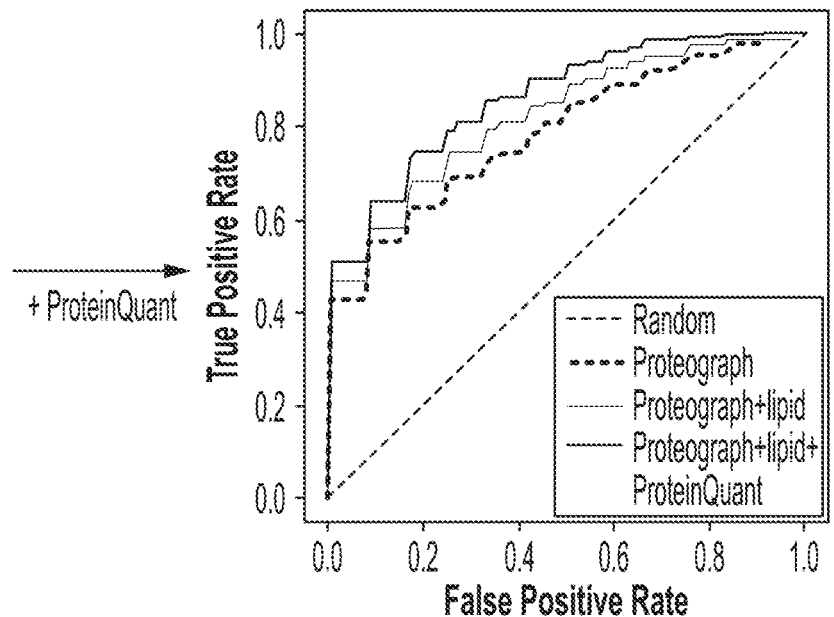

FIG. 3A-3B illustrate an approach in which multiple data sets were combined to improve classifier performance, as illustrated by increased area under the curve (AUC) of receiver operating characteristic (ROC) curves. In FIG. 3A, the left panels (top: all features; bottom: top 20 features) illustrate ROCs generated from the Proteograph classifier, the Lipid classifier, and a combination of the Proteograph and Lipid classifiers ("Proteograph+lipid") in the 83 biological samples. The middle panels (top: all features; bottom: top 20 features) illustrate ROCs generated from the Proteograph classifier, the ProteinQuant classifier, and a combination of the Proteograph and ProteinQuant classifiers ("Proteograph+ProteinQuant") in the 83 biological samples. The right panels (top: all features; bottom: top 20 features) illustrate ROCs generated from the Proteograph, ProteinQuant, and Lipid classifiers, and from the combination of the three ("Proteograph+lipid+ProteinQuant") in the 83 biological samples. In FIG. 3B, the data are presented for easy comparison, with Proteograph in left panels, Proteograph and Proteograph+lipid in the middle panels, and Proteograph+lipid and Proteograph+lipid+ProteinQuant in the right panels. The data in these figures indicate the usefulness and validity of using multiple data sets to improve data classification, even when the data sets comprise measurements of the same type of biomolecule. This combination approach using multiple data sets reduced the signal to noise, and thereby the overall quality, of the data and classification relative to the use of a single data set or a single classifier.

Example 2

Protein Identification Using Particle Enrichment and Heavy-Labeled (Isotope) Internal Standard (PiQ)

This example illustrates identification of proteins using heavy-labeled internal standards (referred here as "PiQ" or "PiQuant"), in combination with nanoparticle enrichment. Methods may include using PiQ may include introducing heavy-labeled internal standards into proteins mixes, before or after nanoparticle enrichment. Here, the method included nanoparticle enrichment before introducing internal standards. PiQ may be used for any of the following: assessing sample quality control (QC); allowing for the enhancement of the protein identification of low abundant protein analytes; or generate higher quality data (e.g. with lower coefficient of variation). Non-limiting example of the QC metrics that can be monitored include LC and MS performance, data analysis performance, or multiple sample preparation metrics.

Using heavy-labeled internal standards and nanoparticle enrichment, 123 additional unique proteins were identified compared to the use of nanoparticle enrichment without the use of heavy-labeled internal standards. Over 500 proteins were observed in the nanoparticle enriched samples, with low coefficient of variation (CV) values. Table 1 illustrates total numbers of proteins identified against the internal standard (IS) panel in either sparse profiles or in full profiles. Table 2 illustrates median CVs of the data generated from the nanoparticle enrichment utilizing various types of nanoparticles (NP1, NP2, NP3, NP4, or NP5, commercially available from Seer, Inc.). The assay included 803 heavy-labeled peptides (which equated to 566 proteins as some proteins had more than one peptide tracking each protein).

TABLE 1

Number of protein identified against the internal standard (IS) panel in either sparse profiles or in full profiles

|  | Proteins ID | IS Panel Size | % |
| --- | --- | --- | --- |
| Sparse Profiles | 508 | 566 | 90 |
| Full Profiles | 457 | 566 | 81 |

TABLE 2

Median CVs of the data generated from the nanoparticle enrichment utilizing various nanoparticles (NPs)

| Nanoparticle | Median CVs (%) |
| --- | --- |
| NP1 | 5.6 |
| NP2 | 8.4 |
| NP3 | 6.3 |
| NP4 | 7.5 |
| NP5 | 20.3 |

Figure 6:
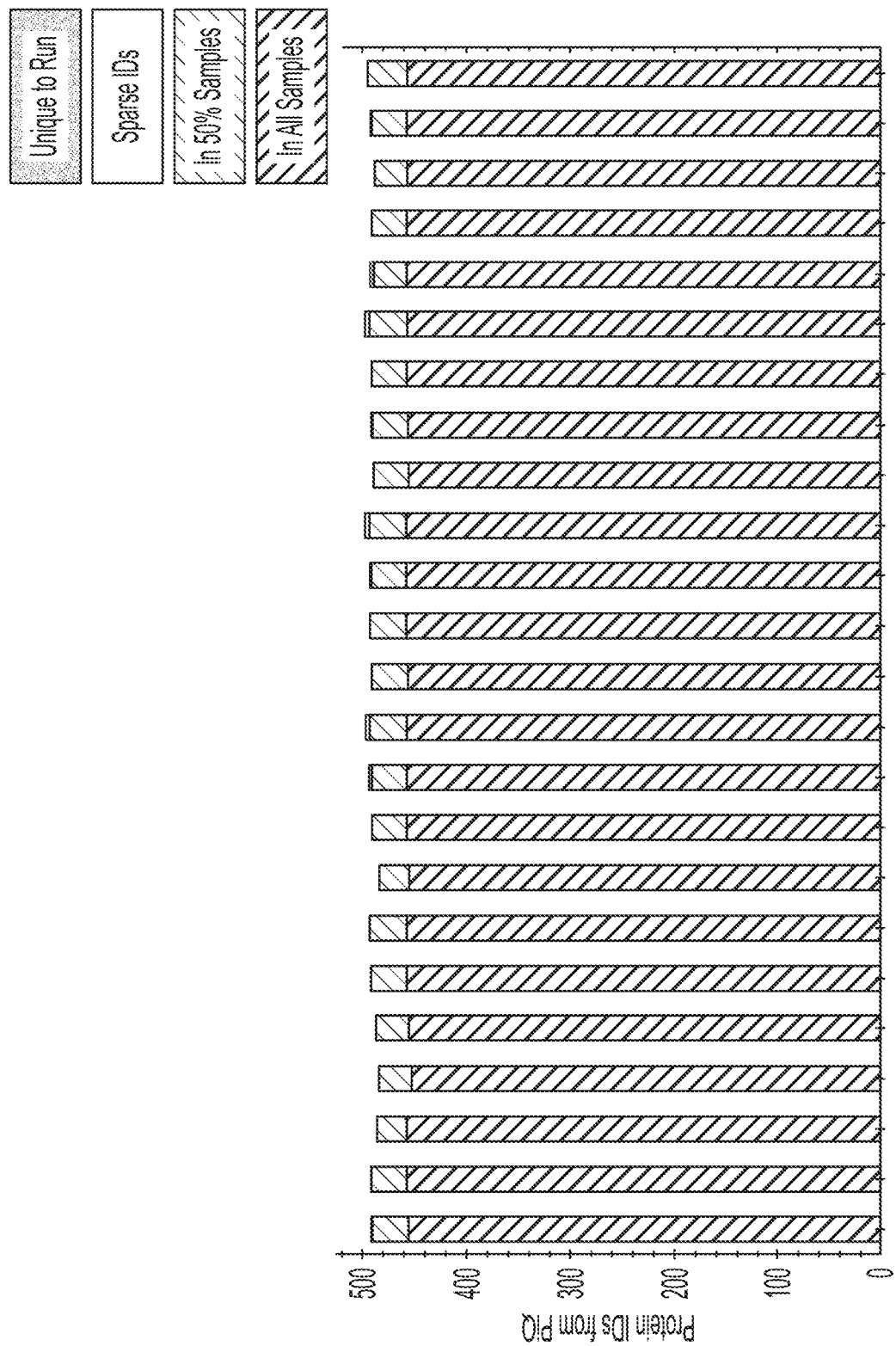
FIG. 6 illustrates non-limiting examples of protein identifications using a PiQ internal standard (IS) method following nanoparticle enrichment.
Figure 7:
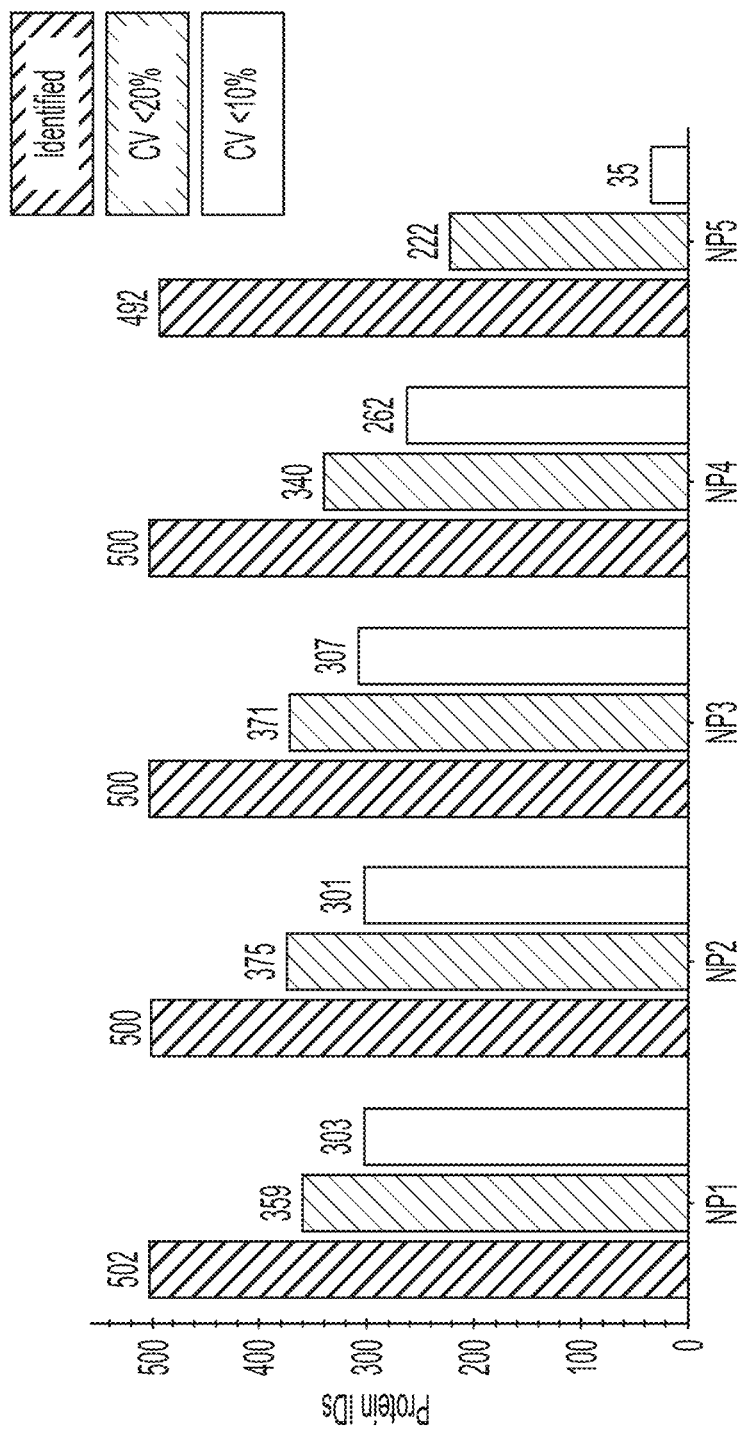
FIG. 7 illustrates non-limiting examples of protein identifications and coefficient of variation (CV) information using a PiQ IS method following nanoparticle enrichment.
Figure 8A:
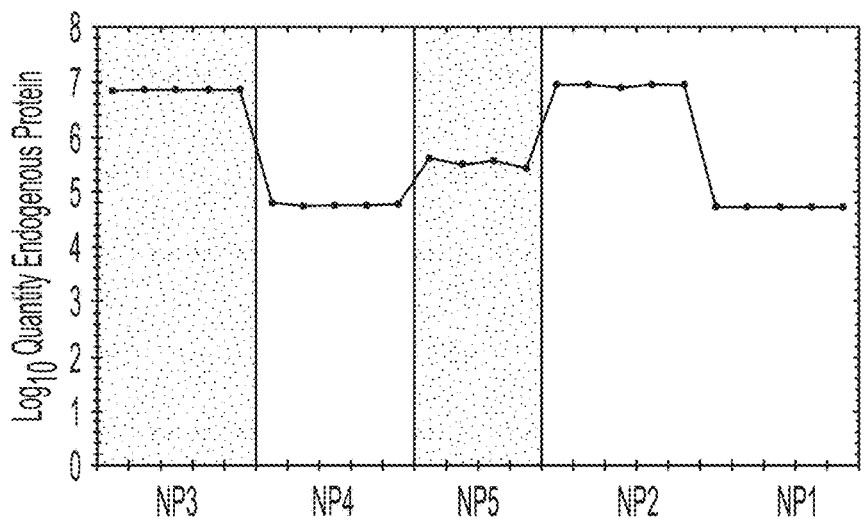
FIG. 8A illustrates a non-limiting example of identifying coagulation factor IX by a PiQ IS method, identified across five different particles.
Figure 8B:
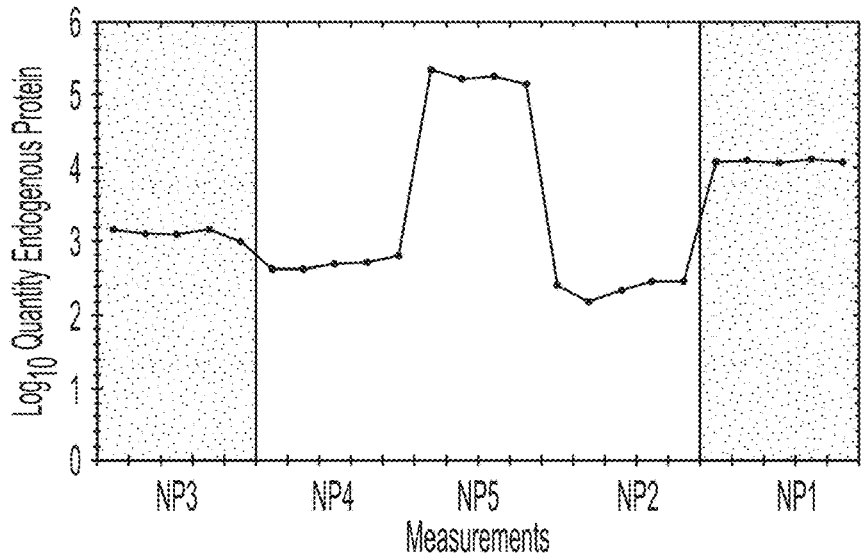
FIG. 8B illustrates a non-limiting example of identifying cathepsin S by a PiQ IS method, identified across five different particles.
Figure 8C:
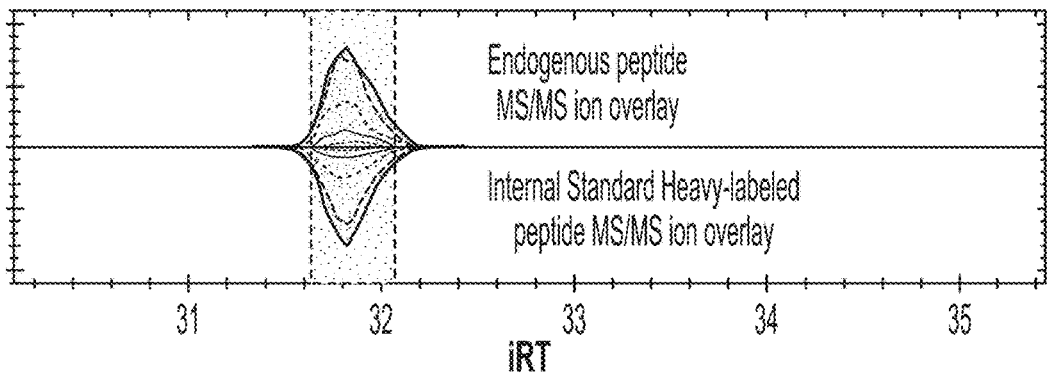
FIG. 8C illustrates a non-limiting example of signal enhancement of low abundance cathepsin S (as seen in FIG. 8B), which allows a user to obtain highly accurate and precise quantitative information.

FIG. 6 and FIG. 7 illustrate protein identifications using a PiQ Internal Standard (IS) method following nanoparticle enrichment. Some advantages of using of PiQ combined with nanoparticle enrichment compared to nanoparticle enrichment only are illustrated in Table 3. FIG. 8A illustrates a non-limiting example of identifying coagulation factor IX through the use of the PiQ internal standard method, identified across five different particles: NP1, NP2, NP3, NP4, and NP5. FIG. 8B illustrates a non-limiting example of identifying low abundance Cathepsin S, by using the PiQ internal standard method, was identified across the same five different particles. FIG. 8C illustrates a non-limiting example of signal enhancement of low abundance Cathepsin S (as seen in FIG. 8B), which allows user to get highly accurate and precise quantitative information.

TABLE 3

Protein identification and quantifications rescued with PiQ internal standard method over nanoparticle enrichment alone

| Protein | Gene | Uniprot | Detected without PiQ | Detected with PiQ |
| --- | --- | --- | --- | --- |
| Cancer antigen 125 (CA-125) | MUC16 | Q8WXI7 | X | ✓ |
| Carcinoembryonic antigen (CEA) | CEA | P06731 | X | ✓ |
| Cancer antigen 19-9 (CA19-9) | ST6GALNAC6 | Q969X2 | X | X |

TABLE 3-continued

Protein identification and quantifications rescued with PiQ internal standard method over nanoparticle enrichment alone

| Protein | Gene | Uniprot | Detected without PiQ | Detected with PiQ |
|---|---|---|---|---|
| Prolactin (PRL) | PRL | P01236 | X | X |
| Hepatocyte growth factor (HGF) | HGF | Q04756 | X | ✓ |
| Osteopontin (OPN) | OPN | P10451 | X | ✓ |
| Myeloperoxidase (MPO) | MPO | P05164 | X | ✓ |
| Tissue inhibitor of metalloproteinases 1 (TIMP-1) | TEMP1 | P01033 | X | ✓ |

The data in this example illustrate the utility and some surprising effects of combining the use of reference biomolecules with a biomolecule assay including the use of particles for measuring endogenous biomolecules.

Example 3

Recovery of False Negative Data and Affirmation of False Positive Data Using Particles with Internal Standards Plasma samples were obtained from healthy subjects. PiQuant internal standards were or were not combined with protein coronas extracted using nanoparticles. The methods here were similar to the methods in Example 2, but the data were generated from a different set of samples, and were collected on a different LCMS instrument, further demonstrating the generalizability of the technology.

FIG. 9A illustrates recovery of a false negative showing that an endogenous peptide comprising hemoglobin subunit delta (HBD, UniProt ID P02042) was present in a biofluid sample but was either not detected or filtered out by a search engine. Incorporation of an internal standard for HBD allowed both detection and confirmation that the peptide was present. The peptide was not detected without use of the internal standards, but both the standard peptide and endogenous peptides were identified using a PiQuant workflow as seen by the identified transitions in the figure. The recovery of a false negative using this technology is applicable to other proteins or peptides, and may be used in methods that involve other types of biomolecules, reference biomolecules, or particles.

FIG. 9B illustrates confirmation of a true negative showing that an endogenous peptide comprising tumor necrosis factor receptor superfamily member 11B (TR11B) was not present in a sample, as confirmed by no detection in the upper panel where there was noise but not a real peak indicating a peptide. An internal standard for TR11B was detected in the lower half of the panel as a chromatographic peak. The confirmation of a true negative using this technology is applicable to other proteins or peptides, and may be used in methods that involve other types of biomolecules, reference biomolecules, or particles.

The data in this example further illustrate the utility and some surprising effects of combining the use of reference biomolecules with a biomolecule assay including the use of particles for measuring endogenous biomolecules.

While the foregoing disclosure has been described in some detail for purposes of clarity and understanding, it will be clear to one skilled in the art from a reading of this disclosure that various changes in form and detail can be made without departing from the true scope of the disclosure. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually and separately indicated to be incorporated by reference for all purposes.

What is claimed is:

1. A method for measuring endogenous biomolecules in a biological sample, comprising:
   (a) contacting a first aliquot of the biological sample with nanoparticles, thereby forming biomolecule coronas comprising the endogenous biomolecules of the biological sample adsorbed directly to the nanoparticles;
   (b) measuring the contacted sample of (a) to obtain a first set of measurements;
   (c) contacting a second aliquot of the biological sample with a plurality of reference biomolecules;
   (d) measuring the contacted sample of (c) to obtain a second set of measurements; and
   (e) combining the first and second sets of measurements, wherein the plurality of reference biomolecules comprises an isotopic label, a mass tag, a barcode, a post-translation modification, or a biomolecule from a species different than a species of a subject from whom the biological sample was taken.

2. The method of claim 1, further comprising identifying concentrations of the endogenous biomolecules based on the combination of measurements from (e).

3. The method of claim 1, further comprising determining a quality control aspect of the endogenous biomolecule measurements based on the combination of measurements from (e).

4. The method of claim 3, wherein the biological sample comprises a group of biological samples, and wherein measuring the endogenous biomolecules comprises measuring the endogenous biomolecules of the group of biological samples and the quality control aspect is in relation to the endogenous biomolecules of the group of biological samples.

5. The method of claim 1, wherein obtaining the first set of measurements or the second set of measurements comprises using a mass spectrometer.

6. The method of claim 1, further comprising normalizing or adjusting the first set of measurements based on the plurality of reference biomolecules.

7. The method of claim 1, wherein the first set of measurements comprises an amount of the endogenous biomolecules in the biological sample.

8. The method of claim 7, further comprising determining an amount of the endogenous biomolecules adsorbed to the nanoparticles relative to the amount of the endogenous biomolecules in the biological sample.

9. The method of claim 1, further comprising identifying a source of variability in the first set of measurements based on the plurality of reference biomolecules.

10. The method of claim 1, further comprising using the plurality of reference biomolecules to identify or measure additional endogenous biomolecules.

11. The method of claim 1, further comprising evaluating a biological state of a subject from whom the biological sample was taken, based on the combination of measurements from (e).

12. The method of claim 1, wherein the endogenous biomolecules comprise proteins, lipids, metabolites, sugars, or nucleic acids.

13. The method of claim 1, wherein the nanoparticles comprise a metal, polymer, or lipid.

14. The method of claim 1, wherein the biological sample comprises a biofluid.

15. The method of claim 1, wherein the adsorbed endogenous biomolecules comprise at least 100 distinct biomolecules.

16. The method of claim 1, wherein the plurality of reference biomolecules is combined with the second aliquot of the biological sample before contacting the second aliquot with nanoparticles resulting in formation of biomolecule coronas.

17. The method of claim 1, wherein the plurality of the reference biomolecules is combined with the second aliquot of the biological sample after contacting the second aliquot with nanoparticles resulting in formation of biomolecule coronas.

18. The method of claim 1, further comprising identifying or measuring a plurality of low abundance biomolecules in the biological sample based on the combination of measurements from (e).

19. The method of claim 1, further comprising recovering a false negative or ruling out a false positive from among the endogenous biomolecules based on the combination of measurements from (e).

20. The method of claim 1, wherein the plurality of reference biomolecules comprises an isotopic label.

21. The method of claim 1, wherein the plurality of reference biomolecules comprises a mass tag.

22. The method of claim 1, wherein the plurality of reference biomolecules comprises a barcode.

23. The method of claim 1, wherein the plurality of reference biomolecules comprises a post-translation modification.

24. The method of claim 1, wherein the plurality of reference biomolecules comprises a biomolecule from a species different than a species of a subject from whom the biological sample was taken.

* * * * *